United States Patent
Weiner et al.

(10) Patent No.: US 9,732,123 B2
(45) Date of Patent: Aug. 15, 2017

(54) **MONO OR MULTIVALENT BOTULINUM NEUROTOXIN BASED VACCINE USING THE HEAVY CHAIN FROM SEROTYPES OF *CLOSTRIDIUM BOTULINUM***

(71) Applicants: David B. Weiner, Merion, PA (US); Veronica Scott, Philadelphia, PA (US); Natalie Hutnick, Malvern, PA (US)

(72) Inventors: David B. Weiner, Merion, PA (US); Veronica Scott, Philadelphia, PA (US); Natalie Hutnick, Malvern, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/774,376

(22) PCT Filed: Mar. 14, 2014

(86) PCT No.: PCT/US2014/026974
§ 371 (c)(1),
(2) Date: Sep. 10, 2015

(87) PCT Pub. No.: WO2014/152121
PCT Pub. Date: Sep. 25, 2014

(65) Prior Publication Data
US 2016/0039889 A1    Feb. 11, 2016

Related U.S. Application Data

(60) Provisional application No. 61/799,094, filed on Mar. 15, 2013.

(51) Int. Cl.
| | | |
|---|---|---|
| *A61K 39/02* | (2006.01) | |
| *A61K 39/08* | (2006.01) | |
| *C07K 14/33* | (2006.01) | |
| *A61M 37/00* | (2006.01) | |
| *A61K 39/00* | (2006.01) | |

(52) U.S. Cl.
CPC ............. *C07K 14/33* (2013.01); *A61K 39/08* (2013.01); *A61M 37/00* (2013.01); *A61K 2039/53* (2013.01); *A61K 2039/55516* (2013.01); *A61K 2039/55527* (2013.01); *A61K 2039/55538* (2013.01); *A61K 2039/575* (2013.01); *A61M 2037/0007* (2013.01)

(58) Field of Classification Search
CPC ....................................................... C07K 14/33
See application file for complete search history.

(56) References Cited

U.S. PATENT DOCUMENTS

| | | | | |
|---|---|---|---|---|
| 7,081,529 | B2 * | 7/2006 | Smith | ................... C07K 14/33 435/69.1 |
| 7,825,233 | B2 | 11/2010 | Steward | |
| 2010/0129371 | A1 | 5/2010 | Scherman | |
| 2010/0297180 | A1 * | 11/2010 | Shone | ................... A61K 39/08 424/239.1 |

FOREIGN PATENT DOCUMENTS

| | | |
|---|---|---|
| WO | 0002524 A2 | 1/2000 |
| WO | 2006017749 A2 | 2/2006 |
| WO | 2008118691 A2 | 10/2008 |
| WO | 2009023549 A2 | 2/2009 |

OTHER PUBLICATIONS

Wang et al., "Selection of Adjuvants for Enhanced Vaccine Potency". World Journal of Vaccines. May 2011, 1 (2):33-78.
Ebrahimi et al., "Production and Characterization of a Recombinant Chimeric Antigen Consisting Botlinum Neurotoxin Serotypes A, B and E Binding Subdomains". J Toxicol Sci. Feb. 2010, 35(1):9-19.
Li et al., "Enhancement of the immunogenicity of DNA replicon vaccine of clostridium botulinum Neurotoxin serotype A GM-CSF Gene adjuvant". Immunopharmacology and Immunotoxicology. Mar. 2011, 33(1):211-219.
Yu et al., "Enhanced Immune Responses Using Plasmid DNA Replicon Vaccine Encoding the Hc domain of Clostridium botulinum Neurotoxin Serotype A". Vaccine. Dec. 17, 2007, 25(52):8843-8850.
Yu et al., "Potent Tetravalent Replicon Vaccines Against Botulinum Neurotoxins Using DNA-based Semliki Forest Virus Replicon Vectors". Vaccine. May 7, 2013, 31(20):2427-2432.

* cited by examiner

*Primary Examiner* — Albert Navarro
(74) *Attorney, Agent, or Firm* — Riverside Law LLP

(57) ABSTRACT

Disclosed herein are compositions and methods for treating *Clostridium botulinum* neurotoxin intoxication and in particular, vaccines against the neurotoxin that provide protection again lethal challenge with neurotoxin from one or more serotypes of *Clostridium botulinum*.

30 Claims, 22 Drawing Sheets

FIG. 3 (con't)

A

BoNT/A Challenge

- Gel-NaH$_2$PO$_4$
- 10$^2$ LD$_{50}$ in Naive
- 10$^2$ LD$_{50}$ in BoNT/Hc/A

Time (h)

B

BoNT/B Challenge

- Gel-NaH$_2$PO$_4$
- 10$^2$ LD$_{50}$ in Naive
- 10$^2$ LD$_{50}$ in BoNT/HcB

Time (h)

FIG. 4

C  BoNT/AB Challenge

- Gel-NaH$_2$PO$_4$
- 10$^2$ LD$_{50}$ of BoNT/A in Naive
- 10$^2$ LD$_{50}$ of BoNT/B in Naive
- 10$^2$ LD$_{50}$ in BoNT/Hc/AB

FIG. 4 (con't)

| Week | 0 | 3 | 6 | 7 | 8 |
|---|---|---|---|---|---|
| DNA Vaccination | ↑ | ↑ | | | |
| Blood Collection | ↑ | ↑ | ↑ | | |
| *Tissue Harvest and Sacrifice | | | ↑ | | |
| Toxin Challenge | | | | ↑ | |
| *Toxin Challenge Endpoint and Sacrifice | | | | | ↑ |

FIG. 11 (con't)

FIG. 11 (con't)

- Gel-NaH$_2$PO$_4$
- $10^4$ LD$_{50}$ BoNT/B + Naive sera
- $10^2$ LD$_{50}$ BoNT/B + Immune sera Time post-inoculation of botulinum B toxin + sera (hours)

FIG. 12 (con't)

D

Percent survival (y-axis: 0, 25, 50, 75, 100)

● Gel-NaH$_2$PO$_4$
■ 10$^2$ LD$_{50}$ BoNT/E + Naive sera
★ 10$^2$ LD$_{50}$ BoNT/E + Immune sera Time post-inoculation of botulinum E toxin + sera (hours)

FIG. 12 (con't)

FIG. 12 (con't)

FIG. 12 (con't)

FIG. 12 (con't)

FIG. 13

SEQUENCE LISTING

<160> NUMBER OF SEQ ID NOS: 11

<210> SEQ ID NO 1
<211> LENGTH: 1328
<212> TYPE: DNA
<213> ORGANISM: Artificial Sequence
<220> FEATURE:
<223> OTHER INFORMATION: Neurotoxin A (BoNT/A)

<400> SEQUENCE: 1

```
ggatccgtcg acgccaccat ggactggacc tggattctgt tcctggtcgc cgccgcaaca    60
agagtgcatt cctcaaacca cctgattgac ctgtctagat acgcatcaaa gatcaatatt   120
ggcagcaaag tgaactttga cccaattgat aagaatcaga tccagctgtt caacctggag   180
agctccaaga tcgaagtgat tctgaaaaac gctatcgtct acaattctat gtatgagaac   240
ttttccacct ctttctggat caggattccc aagtacttta atagtatctc actgaacaac   300
gagtacacaa tcattaactg catggaaaac aactctggat ggaaagtgag tctgaactac   360
ggcgagatca tttggacact gcaggacact caggaaatca agcagcgggt ggtctttaaa   420
tactcccaga tgatcaacat ctctgattac atcaaccgct ggattttcgt gactatcacc   480
aacaatcgac tgaacaatag caagatctat attaacggca gactgattga ccagaaaccc   540
atcagcaacc tggggaatat tcacgcctcc aacaatatca tgtttaagct ggacggctgt   600
agggatcccc atcgctacat ctggattaag tatttcaatc tgttcgacaa ggagctgaac   660
gagaaggaga tcaaggacct gtacgataac agagcaatt ccggcatcct gaaggacttc   720
tggggcgact acctgcagta tgataaaccc tactatatgc tgaatctgta cgaccctaac   780
aagtatgtgg atgtcaacaa tgtgggcatt agagggtaca tgtatctgaa aggacctagg   840
ggcagcgtga tgaccacaaa catctacctg aattctagtc tgtataggg gactaagttc   900
atcattaaga aatacgcatc cggaaacaaa gacaatattg tgcgaaacaa tgatcgggtc   960
tacatcaatg tggtcgtgaa gaacaaagag tatcgcctgg ccaccaatgc ttctcaggca  1020
ggagtggaga agattctgag tgccctggaa atcccagacg tgggcaatct gagtcaggtc  1080
gtggtcatga agtcaaaaaa cgatcagggg atcacaaata agtgcaaaat gaacctgcag  1140
gacaacaatg gcaacgatat cgggttcatt ggatttcacc agttcaacaa tattgccaag  1200
ctggtggctt ccaactggta caatcggcag atcgaacggt caagcagaac actgggatgt  1260
agttgggagt tcattcctgt ggacgatgga tggggagaga gaccactgtg ataaacgcgt  1320
gcggccgc                                                            1328
```

<210> SEQ ID NO 2
<211> LENGTH: 430
<212> TYPE: PRT
<213> ORGANISM: Artificial Sequence
<220> FEATURE:
<223> OTHER INFORMATION: Neurotoxin A (BoNT/A)

<400> SEQUENCE: 2

```
Met Asp Trp Thr Trp Ile Leu Phe Leu Val Ala Ala Thr Arg Val
1               5                   10                  15

His Ser Ser Asn His Leu Ile Asp Leu Ser Arg Tyr Ala Ser Lys Ile
            20                  25                  30

Asn Ile Gly Ser Lys Val Asn Phe Asp Pro Ile Asp Lys Asn Gln Ile
        35                  40                  45

Gln Leu Phe Asn Leu Glu Ser Ser Lys Ile Glu Val Ile Leu Lys Asn
    50                  55                  60

Ala Ile Val Tyr Asn Ser Met Tyr Glu Asn Phe Ser Thr Ser Phe Trp
65                  70                  75                  80

Ile Arg Ile Pro Lys Tyr Phe Asn Ser Ile Ser Leu Asn Asn Glu Tyr
                85                  90                  95

Thr Ile Ile Asn Cys Met Glu Asn Asn Ser Gly Trp Lys Val Ser Leu
            100                 105                 110
```

Asn Tyr Gly Glu Ile Ile Trp Thr Leu Gln Asp Thr Gln Glu Ile Lys
            115                 120                 125

Gln Arg Val Val Phe Lys Tyr Ser Gln Met Ile Asn Ile Ser Asp Tyr
        130                 135                 140

Ile Asn Arg Trp Ile Phe Val Thr Ile Thr Asn Asn Arg Leu Asn Asn
145                 150                 155                 160

Ser Lys Ile Tyr Ile Asn Gly Arg Leu Ile Asp Gln Lys Pro Ile Ser
                165                 170                 175

Asn Leu Gly Asn Ile His Ala Ser Asn Asn Ile Met Phe Lys Leu Asp
            180                 185                 190

Gly Cys Arg Asp Thr His Arg Tyr Ile Trp Ile Lys Tyr Phe Asn Leu
        195                 200                 205

Phe Asp Lys Glu Leu Asn Glu Lys Glu Ile Lys Asp Leu Tyr Asp Asn
210                 215                 220

Gln Ser Asn Ser Gly Ile Leu Lys Asp Phe Trp Gly Asp Tyr Leu Gln
225                 230                 235                 240

Tyr Asp Lys Pro Tyr Tyr Met Leu Asn Leu Tyr Asp Pro Asn Lys Tyr
                245                 250                 255

Val Asp Val Asn Asn Val Gly Ile Arg Gly Tyr Met Tyr Leu Lys Gly
            260                 265                 270

Pro Arg Gly Ser Val Met Thr Thr Asn Ile Tyr Leu Asn Ser Ser Leu
        275                 280                 285

Tyr Arg Gly Thr Lys Phe Ile Ile Lys Lys Tyr Ala Ser Gly Asn Lys
        290                 295                 300

Asp Asn Ile Val Arg Asn Asn Asp Arg Val Tyr Ile Asn Val Val Val
305                 310                 315                 320

Lys Asn Lys Glu Tyr Arg Leu Ala Thr Asn Ala Ser Gln Ala Gly Val
                325                 330                 335

Glu Lys Ile Leu Ser Ala Leu Glu Ile Pro Asp Val Gly Asn Leu Ser
            340                 345                 350

Gln Val Val Val Met Lys Ser Lys Asn Asp Gln Gly Ile Thr Asn Lys
        355                 360                 365

Cys Lys Met Asn Leu Gln Asp Asn Asn Gly Asn Asp Ile Gly Phe Ile
370                 375                 380

Gly Phe His Gln Phe Asn Asn Ile Ala Lys Leu Val Ala Ser Asn Trp
385                 390                 395                 400

Tyr Asn Arg Gln Ile Glu Arg Ser Ser Arg Thr Leu Gly Cys Ser Trp
                405                 410                 415

Glu Phe Ile Pro Val Asp Asp Gly Trp Gly Glu Arg Pro Leu
            420                 425                 430

<210> SEQ ID NO 3
<211> LENGTH: 1346
<212> TYPE: DNA
<213> ORGANISM: Artificial Sequence
<220> FEATURE:
<223> OTHER INFORMATION: Neurotoxin B (BoNT/B)

<400> SEQUENCE: 3
ggatccgggc cgccaccat ggactggaca tggattctgt tcctggtcgc tgctgctaca      60
cgagtgcatt ctgacaacaa cctgattgac ctgagcggct acggcgccaa agtggaagtc     120
tatgatgggg tggagctgaa cgacaagaat cagtttaaac tgacaagctc cgctaacagt     180
aagatcaggg tcactcagaa ccagaatatc atcttcaaca gcgtgttcct ggattttct    240

```
gtcagtttct ggatcagaat ccccaagtac aaaaacgacg gcatccagaa ctacatccac    300
aacgagtaca ccatcattaa ttgcatgaag aacaatagtg gatggaaaat ctcaattagg    360
ggcaaccgca tcatttggac tctgatcgat attaatggga agaccaaatc cgtgttcttt    420
gaatataaca tccgagaaga catttctgag tacatcaatc ggtggttctt tgtgaccatc    480
acaaacaatc tgaacaatgc aaagatctac attaacggca aactggagag caatacagat    540
atcaaggaca ttcgggaagt gattgccaac ggggagatca tcttcaagct ggacggagat    600
attgacagaa ctcagttcat ctggatgaag tatttctcca tctttaacac cgagctgtca    660
cagagcaata ttgaggaaag atacaagatc cagtcctatt ctgaatacct gaaagatttt    720
tggggcaacc cactgatgta caataaggag tactacatgt caacgctgg gaacaagaat    780 tcttacatca agctgaagaa ggatagtccc gtgggagaaa tcctgaccag aagcaagtac    840
aaccagaact ccaagtacat caactacagg gacctgtaca tcggagagaa gttcatcatt    900
cggagaaaaa gtaactcaca gagcattaat gacgatatcg tgcgcaagga agattacatc    960
tatctggact tctttaacct gaatcaggag tggcgagtct acacatacaa gtactttaag   1020
aaggaggaag agaaactgtt cctggccccc atctccgatt ctgacgagtt ttacaacacc   1080
atccagatta aggaatatga tgagcagcct acatactcat gccagctgct gttcaagaaa   1140
gatgaagaga gcactgacga aatcggcctg atcgggattc atcgattcta tgagtccggc   1200
atcgtgttcg aagagtataa ggactacttc tgtatctcta gtggtacct gaaagaggtc   1260 aagcgcaaac cctataatct gaagctggga tgtaattggc agttcattcc taaagacgaa   1320
gggtggaccg aatgataagc ggccgc                                        1346
```

<210> SEQ ID NO 4
<211> LENGTH: 438
<212> TYPE: PRT
<213> ORGANISM: Artificial Sequence
<220> FEATURE:
<223> OTHER INFORMATION: Neurotoxin B (BoNT/B)

<400> SEQUENCE: 4

Met Asp Trp Thr Trp Ile Leu Phe Leu Val Ala Ala Thr Arg Val
1               5                   10                  15

His Ser Asp Asn Asn Leu Ile Asp Leu Ser Gly Tyr Gly Ala Lys Val
            20                  25                  30

Glu Val Tyr Asp Gly Val Glu Leu Asn Asp Lys Asn Gln Phe Lys Leu
        35                  40                  45

Thr Ser Ser Ala Asn Ser Lys Ile Arg Val Thr Gln Asn Gln Asn Ile
    50                  55                  60

Ile Phe Asn Ser Val Phe Leu Asp Phe Ser Val Ser Phe Trp Ile Arg
65                  70                  75                  80

Ile Pro Lys Tyr Lys Asn Asp Gly Ile Gln Asn Tyr Ile His Asn Glu
                85                  90                  95

Tyr Thr Ile Ile Asn Cys Met Lys Asn Asn Ser Gly Trp Lys Ile Ser
            100                 105                 110

Ile Arg Gly Asn Arg Ile Ile Trp Thr Leu Ile Asp Ile Asn Gly Lys
        115                 120                 125

Thr Lys Ser Val Phe Phe Glu Tyr Asn Ile Arg Glu Asp Ile Ser Glu
    130                 135                 140

Tyr Ile Asn Arg Trp Phe Phe Val Thr Ile Thr Asn Asn Leu Asn Asn
145                 150                 155                 160

Ala Lys Ile Tyr Ile Asn Gly Lys Leu Glu Ser Asn Thr Asp Ile Lys

```
                            165                 170                 175
Asp Ile Arg Glu Val Ile Ala Asn Gly Glu Ile Ile Phe Lys Leu Asp
                180                 185                 190

Gly Asp Ile Asp Arg Thr Gln Phe Ile Trp Met Lys Tyr Phe Ser Ile
            195                 200                 205

Phe Asn Thr Glu Leu Ser Gln Ser Asn Ile Glu Glu Arg Tyr Lys Ile
        210                 215                 220

Gln Ser Tyr Ser Glu Tyr Leu Lys Asp Phe Trp Gly Asn Pro Leu Met
225                 230                 235                 240

Tyr Asn Lys Glu Tyr Tyr Met Phe Asn Ala Gly Asn Lys Asn Ser Tyr
                245                 250                 255

Ile Lys Leu Lys Lys Asp Ser Pro Val Gly Glu Ile Leu Thr Arg Ser
            260                 265                 270

Lys Tyr Asn Gln Asn Ser Lys Tyr Ile Asn Tyr Arg Asp Leu Tyr Ile
        275                 280                 285

Gly Glu Lys Phe Ile Ile Arg Arg Lys Ser Asn Ser Gln Ser Ile Asn
    290                 295                 300

Asp Asp Ile Val Arg Lys Glu Asp Tyr Ile Tyr Leu Asp Phe Phe Asn
305                 310                 315                 320

Leu Asn Gln Glu Trp Arg Val Tyr Thr Tyr Lys Tyr Phe Lys Lys Glu
                325                 330                 335

Glu Glu Lys Leu Phe Leu Ala Pro Ile Ser Asp Ser Asp Glu Phe Tyr
            340                 345                 350

Asn Thr Ile Gln Ile Lys Glu Tyr Asp Glu Gln Pro Thr Tyr Ser Cys
        355                 360                 365

Gln Leu Leu Phe Lys Lys Asp Glu Glu Ser Thr Asp Glu Ile Gly Leu
    370                 375                 380

Ile Gly Ile His Arg Phe Tyr Glu Ser Gly Ile Val Phe Glu Glu Tyr
385                 390                 395                 400

Lys Asp Tyr Phe Cys Ile Ser Lys Trp Tyr Leu Lys Glu Val Lys Arg
                405                 410                 415

Lys Pro Tyr Asn Leu Lys Leu Gly Cys Asn Trp Gln Phe Ile Pro Lys
            420                 425                 430

Asp Glu Gly Trp Thr Glu
        435
```

<210> SEQ ID NO 5
<211> LENGTH: 1271
<212> TYPE: DNA
<213> ORGANISM: Artificial Sequence
<220> FEATURE:
<223> OTHER INFORMATION: Neurotoxin E (BoNT/E)

<400> SEQUENCE: 5

```
ggatccgtcg acgccaccat ggactggact tggattctgt tcctggtcgc cgccgcaacc    60
cgcgtgcatt ctgacaaata tgtggacacc tcaggctatg actctaatat caacattaat   120
ggcgacgtgt acaagtatcc aaccaacaaa atcagttcg gcatctacaa cgataagctg    180
tcagaggtga acatcagcca gaatgactac atcatctacg ataacaagta caagaatttc   240
agcatttcct tgggtccg catccccaac tacgacaaca gattgtcaa cgtgaacaac      300 gagtacacaa tcattaattg catgcgagat aacaattccg ggtggaaggt gtctctgaac   360
cacaatgaaa tcatttggac tctgcaggac aacgccggaa tcaatcagaa actggctttc   420
aactacggaa acgcaaatgg catctctgat tacatcaaca agtggatctt cgtgactatt   480
```

```
accaatgacc ggctggggga tagtaaactg tacatcaacg gaaatctgat tgaccagaag    540
agtatcctga acctgggcaa tatccatgtc tcagataaca tcctgtttaa aatcgtgaac    600
tgtagctaca ccaggtatat cgggattcgc tacttcaaca tttttgacaa ggagctggat    660
gagacagaaa tccagactct gtatagcaat gaacccaaca caaatatcct gaaggacttc    720
tggggaaact acctgctgta tgataaggag tactatctgc tgaatgtgct gaaacctaat    780
aacttcatcg accggagaaa ggattctaca ctgagtatca acaatattcg aagcactatc    840
ctgctggcca accggctgta ctccgggatc aaggtcaaaa ttcagagagt gaacaatagc    900
tccaccaacg acaatctggt gaggaaaaac gatcaggtct acatcaatttt cgtggctagc    960 aagacacacc tgtttcccct gtatgccgac actgctacca caaacaagga aaaaccatc   1020 aagatttcta gttcaggcaa caggttcaat caggtggtcg tgatgaactc cgtgggcaac   1080
aactgcacta tgaatttcaa aaacaacaac gggaacaaca tcggcctgct ggggtttaag   1140
gcagacaccg tcgtggcctc tacctggtac tatacacaca tgcgggatca tacaaattca   1200
aatggatgtt tctggaactt tattagtgag gagcatgggt ggcaggaaaa atgataaacg   1260
cgtgcggccg c                                                        1271
```

<210> SEQ ID NO 6
<211> LENGTH: 411
<212> TYPE: PRT
<213> ORGANISM: Artificial Sequence
<220> FEATURE:
<223> OTHER INFORMATION: Neurotoxin E (BoNT/E)

<400> SEQUENCE: 6

```
Met Asp Trp Thr Trp Ile Leu Phe Leu Val Ala Ala Thr Arg Val
1               5                   10                  15

His Ser Asp Lys Tyr Val Asp Thr Ser Gly Tyr Asp Ser Asn Ile Asn
            20                  25                  30

Ile Asn Gly Asp Val Tyr Lys Tyr Pro Thr Asn Lys Asn Gln Phe Gly
        35                  40                  45

Ile Tyr Asn Asp Lys Leu Ser Glu Val Asn Ile Ser Gln Asn Asp Tyr
    50                  55                  60

Ile Ile Tyr Asp Asn Lys Tyr Lys Asn Phe Ser Ile Ser Phe Trp Val
65                  70                  75                  80

Arg Ile Pro Asn Tyr Asp Asn Lys Ile Val Asn Val Asn Asn Glu Tyr
                85                  90                  95

Thr Ile Ile Asn Cys Met Arg Asp Asn Asn Ser Gly Trp Lys Val Ser
            100                 105                 110

Leu Asn His Asn Glu Ile Ile Trp Thr Leu Gln Asp Asn Ala Gly Ile
        115                 120                 125

Asn Gln Lys Leu Ala Phe Asn Tyr Gly Asn Ala Asn Gly Ile Ser Asp
    130                 135                 140

Tyr Ile Asn Lys Trp Ile Phe Val Thr Ile Thr Asn Asp Arg Leu Gly
145                 150                 155                 160

Asp Ser Lys Leu Tyr Ile Asn Gly Asn Leu Ile Asp Gln Lys Ser Ile
                165                 170                 175

Leu Asn Leu Gly Asn Ile His Val Ser Asp Asn Ile Leu Phe Lys Ile
            180                 185                 190

Val Asn Cys Ser Tyr Thr Arg Tyr Ile Gly Ile Arg Tyr Phe Asn Ile
        195                 200                 205

Phe Asp Lys Glu Leu Asp Glu Thr Glu Ile Gln Thr Leu Tyr Ser Asn
    210                 215                 220
```

```
Glu Pro Asn Thr Asn Ile Leu Lys Asp Phe Trp Gly Asn Tyr Leu Leu
225                 230                 235                 240

Tyr Asp Lys Glu Tyr Tyr Leu Leu Asn Val Leu Lys Pro Asn Asn Phe
            245                 250                 255

Ile Asp Arg Arg Lys Asp Ser Thr Leu Ser Ile Asn Asn Ile Arg Ser
        260                 265                 270

Thr Ile Leu Leu Ala Asn Arg Leu Tyr Ser Gly Ile Lys Val Lys Ile
    275                 280                 285

Gln Arg Val Asn Asn Ser Ser Thr Asn Asp Asn Leu Val Arg Lys Asn
290                 295                 300

Asp Gln Val Tyr Ile Asn Phe Val Ala Ser Lys Thr His Leu Phe Pro
305                 310                 315                 320

Leu Tyr Ala Asp Thr Ala Thr Thr Asn Lys Glu Lys Thr Ile Lys Ile
                325                 330                 335

Ser Ser Ser Gly Asn Arg Phe Asn Gln Val Val Met Asn Ser Val
            340                 345                 350

Gly Asn Asn Cys Thr Met Asn Phe Lys Asn Asn Gly Asn Asn Ile
        355                 360                 365

Gly Leu Leu Gly Phe Lys Ala Asp Thr Val Val Ala Ser Thr Trp Tyr
    370                 375                 380

Tyr Thr His Met Arg Asp His Thr Asn Ser Asn Gly Cys Phe Trp Asn
385                 390                 395                 400

Phe Ile Ser Glu Glu His Gly Trp Gln Glu Lys
                405                 410

<210> SEQ ID NO 7
<211> LENGTH: 1289
<212> TYPE: DNA
<213> ORGANISM: Artificial Sequence
<220> FEATURE:
<223> OTHER INFORMATION: Neurotoxin F (BoNT/F)

<400> SEQUENCE: 7
ggatccgggc cgccaccat ggactggaca tggattctgt tcctggtggc tgctgctaca      60
agagtgcatt caaataacaa attcattgac atctcaggct acggctctaa catcagtatt    120
aatggcgacg tgtacatcta cagcaccaac cgaaatcagt tcgggatcta cagctccaag    180
ccatccgagg tgaacattgc acagaacaat gatatcatct acaacggccg gtatcagaat    240
ttctcaatta gcttttgggt gagaatcccc aagtacttta caaggtcaa tctgaacaac    300 gaatacacaa tcatcgactg catccgcaac aataactccg gatggaagat ctctctgaac    360
tacaataaga tcatctggac tctgcaggac accgccggca ataaccagaa actggtgttc    420
aattacactc agatgatctc catctctgat tacatcaaca gtggatcttc gtcaccatc    480 acaaataacc ggctggggaa ctctagaatc tatatcaacg gaaatctgat cgatgagaag    540
agtatctcaa acctgggcga catccacgtg agcgataata ttctgttcaa gatcgtcggc    600
tgtaacgaca ccagatacgt gggcatccgg tatttcaaag tctttgatac agagctgggg    660
aagacagaga tcgaaactct gtacagcgac gaacccgatc cttccattct gaaagacttt    720
tggggaaact acctgctgta taataagaga tactatctgc tgaatctgct gaggactgat    780
aagagtatca cccagaactc aaatttcctg aacatcaatc agcagagagg ggtgtaccag    840
aagcctaaca tctttagcaa tacccgcctg tatacaggag tggaagtcat cattcgaaaa    900
aacggctcaa cagacatcag caacactgat aatttcgtga ggaagaacga cctggcttac    960
```

```
attaatgtgg tcgaccgaga tgtcgagtac cggctgtatg ccgatatctc cattgctaag    1020
cccgaaaaaa tcattaagct gatccgcact agcaattcca ataactctct ggggcagatc    1080
attgtgatgg acagtatcgg aaataactgc accatgaact tccagaataa caatggcgga    1140
aatatcggac tgctgggctt tcattctaac aatctggtgg cctctagttg gtactataac    1200
aatatccgga agaacacttc atccaatggg tgtttctggt ccttcatctc caaagagcat    1260
gggtggcagg aaaattgata agcggccgc                                      1289
```

<210> SEQ ID NO 8
<211> LENGTH: 419
<212> TYPE: PRT
<213> ORGANISM: Artificial Sequence
<220> FEATURE:
<223> OTHER INFORMATION: Neurotoxin F (BoNT/F)

<400> SEQUENCE: 8

```
Met Asp Trp Thr Trp Ile Leu Phe Leu Val Ala Ala Thr Arg Val
1               5                   10                  15

His Ser Asn Asn Lys Phe Ile Asp Ile Ser Gly Tyr Gly Ser Asn Ile
            20                  25                  30

Ser Ile Asn Gly Asp Val Tyr Ile Tyr Ser Thr Asn Arg Asn Gln Phe
        35                  40                  45

Gly Ile Tyr Ser Ser Lys Pro Ser Glu Val Asn Ile Ala Gln Asn Asn
    50                  55                  60

Asp Ile Ile Tyr Asn Gly Arg Tyr Gln Asn Phe Ser Ile Ser Phe Trp
65                  70                  75                  80

Val Arg Ile Pro Lys Tyr Phe Asn Lys Val Asn Leu Asn Asn Glu Tyr
                85                  90                  95

Thr Ile Ile Asp Cys Ile Arg Asn Asn Asn Ser Gly Trp Lys Ile Ser
            100                 105                 110

Leu Asn Tyr Asn Lys Ile Ile Trp Thr Leu Gln Asp Thr Ala Gly Asn
        115                 120                 125

Asn Gln Lys Leu Val Phe Asn Tyr Thr Gln Met Ile Ser Ile Ser Asp
    130                 135                 140

Tyr Ile Asn Lys Trp Ile Phe Val Thr Ile Thr Asn Asn Arg Leu Gly
145                 150                 155                 160

Asn Ser Arg Ile Tyr Ile Asn Gly Asn Leu Ile Asp Glu Lys Ser Ile
                165                 170                 175

Ser Asn Leu Gly Asp Ile His Val Ser Asp Asn Ile Leu Phe Lys Ile
            180                 185                 190

Val Gly Cys Asn Asp Thr Arg Tyr Val Gly Ile Arg Tyr Phe Lys Val
        195                 200                 205

Phe Asp Thr Glu Leu Gly Lys Thr Glu Ile Glu Thr Leu Tyr Ser Asp
    210                 215                 220

Glu Pro Asp Pro Ser Ile Leu Lys Asp Phe Trp Gly Asn Tyr Leu Leu
225                 230                 235                 240

Tyr Asn Lys Arg Tyr Tyr Leu Leu Asn Leu Leu Arg Thr Asp Lys Ser
                245                 250                 255

Ile Thr Gln Asn Ser Asn Phe Leu Asn Ile Asn Gln Gln Arg Gly Val
            260                 265                 270

Tyr Gln Lys Pro Asn Ile Phe Ser Asn Thr Arg Leu Tyr Thr Gly Val
        275                 280                 285

Glu Val Ile Ile Arg Lys Asn Gly Ser Thr Asp Ile Ser Asn Thr Asp
    290                 295                 300
```

```
Asn Phe Val Arg Lys Asn Asp Leu Ala Tyr Ile Asn Val Val Asp Arg
305                 310                 315                 320

Asp Val Glu Tyr Arg Leu Tyr Ala Asp Ile Ser Ile Ala Lys Pro Glu
            325                 330                 335

Lys Ile Ile Lys Leu Ile Arg Thr Ser Asn Ser Asn Asn Ser Leu Gly
            340                 345                 350

Gln Ile Ile Val Met Asp Ser Ile Gly Asn Asn Cys Thr Met Asn Phe
            355                 360                 365

Gln Asn Asn Gly Gly Asn Ile Gly Leu Leu Gly Phe His Ser Asn
    370                 375                 380

Asn Leu Val Ala Ser Ser Trp Tyr Tyr Asn Asn Ile Arg Lys Asn Thr
385                 390                 395                 400

Ser Ser Asn Gly Cys Phe Trp Ser Phe Ile Ser Lys Glu His Gly Trp
                405                 410                 415

Gln Glu Asn

<210> SEQ ID NO 9
<211> LENGTH: 857
<212> TYPE: PRT
<213> ORGANISM: Artificial Sequence
<220> FEATURE:
<223> OTHER INFORMATION: Neurotoxin A + B (BoNT/A + BoNT/B)

<400> SEQUENCE: 9

Met Asp Trp Thr Trp Ile Leu Phe Leu Val Ala Ala Thr Arg Val
1               5                   10                  15

His Ser Ser Asn His Leu Ile Asp Leu Ser Arg Tyr Ala Ser Lys Ile
            20                  25                  30

Asn Ile Gly Ser Lys Val Asn Phe Asp Pro Ile Asp Lys Asn Gln Ile
            35                  40                  45

Gln Leu Phe Asn Leu Glu Ser Ser Lys Ile Glu Val Ile Leu Lys Asn
        50                  55                  60

Ala Ile Val Tyr Asn Ser Met Tyr Glu Asn Phe Ser Thr Ser Phe Trp
65                  70                  75                  80

Ile Arg Ile Pro Lys Tyr Phe Asn Ser Ile Ser Leu Asn Asn Glu Tyr
                85                  90                  95

Thr Ile Ile Asn Cys Met Glu Asn Asn Ser Gly Trp Lys Val Ser Leu
            100                 105                 110

Asn Tyr Gly Glu Ile Ile Trp Thr Leu Gln Asp Thr Gln Glu Ile Lys
        115                 120                 125

Gln Arg Val Val Phe Lys Tyr Ser Gln Met Ile Asn Ile Ser Asp Tyr
    130                 135                 140

Ile Asn Arg Trp Ile Phe Val Thr Ile Thr Asn Asn Arg Leu Asn Asn
145                 150                 155                 160

Ser Lys Ile Tyr Ile Asn Gly Arg Leu Ile Asp Gln Lys Pro Ile Ser
                165                 170                 175

Asn Leu Gly Asn Ile His Ala Ser Asn Asn Ile Met Phe Lys Leu Asp
            180                 185                 190

Gly Cys Arg Asp Thr His Arg Tyr Ile Trp Ile Lys Tyr Phe Asn Leu
        195                 200                 205

Phe Asp Lys Glu Leu Asn Glu Lys Glu Ile Lys Asp Leu Tyr Asp Asn
    210                 215                 220

Gln Ser Asn Ser Gly Ile Leu Lys Asp Phe Trp Gly Asp Tyr Leu Gln
225                 230                 235                 240

Tyr Asp Lys Pro Tyr Tyr Met Leu Asn Leu Tyr Asp Pro Asn Lys Tyr
```

-continued

```
            245                 250                 255
Val Asp Val Asn Asn Val Gly Ile Arg Gly Tyr Met Tyr Leu Lys Gly
            260                 265                 270

Pro Arg Gly Ser Val Met Thr Thr Asn Ile Tyr Leu Asn Ser Ser Leu
        275                 280                 285

Tyr Arg Gly Thr Lys Phe Ile Ile Lys Lys Tyr Ala Ser Gly Asn Lys
    290                 295                 300

Asp Asn Ile Val Arg Asn Asn Asp Arg Val Tyr Ile Asn Val Val Val
305                 310                 315                 320

Lys Asn Lys Glu Tyr Arg Leu Ala Thr Asn Ala Ser Gln Ala Gly Val
                325                 330                 335

Glu Lys Ile Leu Ser Ala Leu Glu Ile Pro Asp Val Gly Asn Leu Ser
            340                 345                 350

Gln Val Val Val Met Lys Ser Lys Asn Asp Gln Gly Ile Thr Asn Lys
        355                 360                 365

Cys Lys Met Asn Leu Gln Asp Asn Asn Gly Asn Asp Ile Gly Phe Ile
    370                 375                 380

Gly Phe His Gln Phe Asn Asn Ile Ala Lys Leu Val Ala Ser Asn Trp
385                 390                 395                 400

Tyr Asn Arg Gln Ile Glu Arg Ser Ser Arg Thr Leu Gly Cys Ser Trp
                405                 410                 415

Glu Phe Ile Pro Val Asp Asp Gly Trp Gly Glu Arg Pro Leu Arg Gly
            420                 425                 430

Arg Lys Arg Arg Ser Asp Asn Asn Leu Ile Asp Leu Ser Gly Tyr Gly
        435                 440                 445

Ala Lys Val Glu Val Tyr Asp Gly Val Glu Leu Asn Asp Lys Asn Gln
    450                 455                 460

Phe Lys Leu Thr Ser Ser Ala Asn Ser Lys Ile Arg Val Thr Gln Asn
465                 470                 475                 480

Gln Asn Ile Ile Phe Asn Ser Val Phe Leu Asp Phe Ser Val Ser Phe
                485                 490                 495

Trp Ile Arg Ile Pro Lys Tyr Lys Asn Asp Gly Ile Gln Asn Tyr Ile
            500                 505                 510

His Asn Glu Tyr Thr Ile Ile Asn Cys Met Lys Asn Asn Ser Gly Trp
        515                 520                 525

Lys Ile Ser Ile Arg Gly Asn Arg Ile Ile Trp Thr Leu Ile Asp Ile
    530                 535                 540

Asn Gly Lys Thr Lys Ser Val Phe Phe Glu Tyr Asn Ile Arg Glu Asp
545                 550                 555                 560

Ile Ser Glu Tyr Ile Asn Arg Trp Phe Phe Val Thr Ile Thr Asn Asn
                565                 570                 575

Leu Asn Asn Ala Lys Ile Tyr Ile Asn Gly Lys Leu Glu Ser Asn Thr
            580                 585                 590

Asp Ile Lys Asp Ile Arg Glu Val Ile Ala Asn Gly Glu Ile Ile Phe
        595                 600                 605

Lys Leu Asp Gly Asp Ile Asp Arg Thr Gln Phe Ile Trp Met Lys Tyr
    610                 615                 620

Phe Ser Ile Phe Asn Thr Glu Leu Ser Gln Ser Asn Ile Glu Glu Arg
625                 630                 635                 640

Tyr Lys Ile Gln Ser Tyr Ser Glu Tyr Leu Lys Asp Phe Trp Gly Asn
                645                 650                 655

Pro Leu Met Tyr Asn Lys Glu Tyr Tyr Met Phe Asn Ala Gly Asn Lys
            660                 665                 670
```

```
Asn Ser Tyr Ile Lys Leu Lys Asp Ser Pro Val Gly Glu Ile Leu
            675                 680                 685

Thr Arg Ser Lys Tyr Asn Gln Asn Ser Lys Tyr Ile Asn Tyr Arg Asp
690                 695                 700

Leu Tyr Ile Gly Glu Lys Phe Ile Ile Arg Arg Lys Ser Asn Ser Gln
705                 710                 715                 720

Ser Ile Asn Asp Asp Ile Val Arg Lys Glu Asp Tyr Ile Tyr Leu Asp
                725                 730                 735

Phe Phe Asn Leu Asn Gln Glu Trp Arg Val Tyr Thr Tyr Lys Tyr Phe
            740                 745                 750

Lys Lys Glu Glu Glu Lys Leu Phe Leu Ala Pro Ile Ser Asp Ser Asp
            755                 760                 765

Glu Phe Tyr Asn Thr Ile Gln Ile Lys Glu Tyr Asp Glu Gln Pro Thr
770                 775                 780

Tyr Ser Cys Gln Leu Leu Phe Lys Lys Asp Glu Glu Ser Thr Asp Glu
785                 790                 795                 800

Ile Gly Leu Ile Gly Ile His Arg Phe Tyr Glu Ser Gly Ile Val Phe
                805                 810                 815

Glu Glu Tyr Lys Asp Tyr Phe Cys Ile Ser Lys Trp Tyr Leu Lys Glu
            820                 825                 830

Val Lys Arg Lys Pro Tyr Asn Leu Lys Leu Gly Cys Asn Trp Gln Phe
            835                 840                 845

Ile Pro Lys Asp Glu Gly Trp Thr Glu
        850                 855

<210> SEQ ID NO 10
<211> LENGTH: 819
<212> TYPE: PRT
<213> ORGANISM: Artificial Sequence
<220> FEATURE:
<223> OTHER INFORMATION: Neurotoxin E + F (BoNT/E + BoNT/F)

<400> SEQUENCE: 10

Met Asp Trp Thr Trp Ile Leu Phe Leu Val Ala Ala Ala Thr Arg Val
1               5                   10                  15

His Ser Asp Lys Tyr Val Asp Thr Ser Gly Tyr Asp Ser Asn Ile Asn
                20                  25                  30

Ile Asn Gly Asp Val Tyr Lys Tyr Pro Thr Asn Lys Asn Gln Phe Gly
            35                  40                  45

Ile Tyr Asn Asp Lys Leu Ser Glu Val Asn Ile Ser Gln Asn Asp Tyr
        50                  55                  60

Ile Ile Tyr Asp Asn Lys Tyr Lys Asn Phe Ser Ile Ser Phe Trp Val
65                  70                  75                  80

Arg Ile Pro Asn Tyr Asp Asn Lys Ile Val Asn Val Asn Asn Glu Tyr
                85                  90                  95

Thr Ile Ile Asn Cys Met Arg Asp Asn Asn Ser Gly Trp Lys Val Ser
            100                 105                 110

Leu Asn His Asn Glu Ile Ile Trp Thr Leu Gln Asp Asn Ala Gly Ile
        115                 120                 125

Asn Gln Lys Leu Ala Phe Asn Tyr Gly Asn Ala Asn Gly Ile Ser Asp
    130                 135                 140

Tyr Ile Asn Lys Trp Ile Phe Val Thr Ile Thr Asn Asp Arg Leu Gly
145                 150                 155                 160

Asp Ser Lys Leu Tyr Ile Asn Gly Asn Leu Ile Asp Gln Lys Ser Ile
                165                 170                 175
```

```
Leu Asn Leu Gly Asn Ile His Val Ser Asp Asn Ile Leu Phe Lys Ile
            180                 185                 190

Val Asn Cys Ser Tyr Thr Arg Tyr Ile Gly Ile Arg Tyr Phe Asn Ile
            195                 200                 205

Phe Asp Lys Glu Leu Asp Glu Thr Glu Ile Gln Thr Leu Tyr Ser Asn
210                 215                 220

Glu Pro Asn Thr Asn Ile Leu Lys Asp Phe Trp Gly Asn Tyr Leu Leu
225                 230                 235                 240

Tyr Asp Lys Glu Tyr Tyr Leu Leu Asn Val Leu Lys Pro Asn Asn Phe
            245                 250                 255

Ile Asp Arg Arg Lys Asp Ser Thr Leu Ser Ile Asn Asn Ile Arg Ser
            260                 265                 270

Thr Ile Leu Leu Ala Asn Arg Leu Tyr Ser Gly Ile Lys Val Lys Ile
            275                 280                 285

Gln Arg Val Asn Asn Ser Ser Thr Asn Asp Asn Leu Val Arg Lys Asn
            290                 295                 300

Asp Gln Val Tyr Ile Asn Phe Val Ala Ser Lys Thr His Leu Phe Pro
305                 310                 315                 320

Leu Tyr Ala Asp Thr Ala Thr Thr Asn Lys Glu Lys Thr Ile Lys Ile
            325                 330                 335

Ser Ser Ser Gly Asn Arg Phe Asn Gln Val Val Val Met Asn Ser Val
            340                 345                 350

Gly Asn Asn Cys Thr Met Asn Phe Lys Asn Asn Asn Gly Asn Asn Ile
            355                 360                 365

Gly Leu Leu Gly Phe Lys Ala Asp Thr Val Val Ala Ser Thr Trp Tyr
            370                 375                 380

Tyr Thr His Met Arg Asp His Thr Asn Ser Asn Gly Cys Phe Trp Asn
385                 390                 395                 400

Phe Ile Ser Glu Glu His Gly Trp Gln Glu Lys Arg Gly Arg Lys Arg
            405                 410                 415

Arg Ser Asn Asn Lys Phe Ile Asp Ile Ser Gly Tyr Gly Ser Asn Ile
            420                 425                 430

Ser Ile Asn Gly Asp Val Tyr Ile Tyr Ser Thr Asn Arg Asn Gln Phe
            435                 440                 445

Gly Ile Tyr Ser Ser Lys Pro Ser Glu Val Asn Ile Ala Gln Asn Asn
450                 455                 460

Asp Ile Ile Tyr Asn Gly Arg Tyr Gln Asn Phe Ser Ile Ser Phe Trp
465                 470                 475                 480

Val Arg Ile Pro Lys Tyr Phe Asn Lys Val Asn Leu Asn Asn Glu Tyr
            485                 490                 495

Thr Ile Ile Asp Cys Ile Arg Asn Asn Asn Ser Gly Trp Lys Ile Ser
            500                 505                 510

Leu Asn Tyr Asn Lys Ile Ile Trp Thr Leu Gln Asp Thr Ala Gly Asn
            515                 520                 525

Asn Gln Lys Leu Val Phe Asn Tyr Thr Gln Met Ile Ser Ile Ser Asp
            530                 535                 540

Tyr Ile Asn Lys Trp Ile Phe Val Thr Ile Thr Asn Asn Arg Leu Gly
545                 550                 555                 560

Asn Ser Arg Ile Tyr Ile Asn Gly Asn Leu Ile Asp Glu Lys Ser Ile
            565                 570                 575

Ser Asn Leu Gly Asp Ile His Val Ser Asp Asn Ile Leu Phe Lys Ile
            580                 585                 590
```

```
Val Gly Cys Asn Asp Thr Arg Tyr Val Gly Ile Arg Tyr Phe Lys Val
            595                 600                 605

Phe Asp Thr Glu Leu Gly Lys Thr Glu Ile Glu Thr Leu Tyr Ser Asp
610                 615                 620

Glu Pro Asp Pro Ser Ile Leu Lys Asp Phe Trp Gly Asn Tyr Leu Leu
625                 630                 635                 640

Tyr Asn Lys Arg Tyr Tyr Leu Leu Asn Leu Leu Arg Thr Asp Lys Ser
                645                 650                 655

Ile Thr Gln Asn Ser Asn Phe Leu Asn Ile Asn Gln Gln Arg Gly Val
            660                 665                 670

Tyr Gln Lys Pro Asn Ile Phe Ser Asn Thr Arg Leu Tyr Thr Gly Val
        675                 680                 685

Glu Val Ile Ile Arg Lys Asn Gly Ser Thr Asp Ile Ser Asn Thr Asp
690                 695                 700

Asn Phe Val Arg Lys Asn Asp Leu Ala Tyr Ile Asn Val Val Asp Arg
705                 710                 715                 720

Asp Val Glu Tyr Arg Leu Tyr Ala Asp Ile Ser Ile Ala Lys Pro Glu
                725                 730                 735

Lys Ile Ile Lys Leu Ile Arg Thr Ser Asn Ser Asn Asn Ser Leu Gly
            740                 745                 750

Gln Ile Ile Val Met Asp Ser Ile Gly Asn Asn Cys Thr Met Asn Phe
        755                 760                 765

Gln Asn Asn Asn Gly Gly Asn Ile Gly Leu Leu Gly Phe His Ser Asn
770                 775                 780

Asn Leu Val Ala Ser Ser Trp Tyr Tyr Asn Asn Ile Arg Lys Asn Thr
785                 790                 795                 800

Ser Ser Asn Gly Cys Phe Trp Ser Phe Ile Ser Lys Glu His Gly Trp
                805                 810                 815

Gln Glu Asn

<210> SEQ ID NO 11
<211> LENGTH: 1665
<212> TYPE: PRT
<213> ORGANISM: Artificial Sequence
<220> FEATURE:
<223> OTHER INFORMATION: Neurotoxin A + B + E + F (BoNT/A + BoNT/B +
      BoNT/E + BoNT/F)

<400> SEQUENCE: 11

Met Asp Trp Thr Trp Ile Leu Phe Leu Val Ala Ala Thr Arg Val
1               5                   10                  15

His Ser Ser Asn His Leu Ile Asp Leu Ser Arg Tyr Ala Ser Lys Ile
                20                  25                  30

Asn Ile Gly Ser Lys Val Asn Phe Asp Pro Ile Asp Lys Asn Gln Ile
            35                  40                  45

Gln Leu Phe Asn Leu Glu Ser Ser Lys Ile Glu Val Ile Leu Lys Asn
        50                  55                  60

Ala Ile Val Tyr Asn Ser Met Tyr Glu Asn Phe Ser Thr Ser Phe Trp
65                  70                  75                  80

Ile Arg Ile Pro Lys Tyr Phe Asn Ser Ile Ser Leu Asn Asn Glu Tyr
                85                  90                  95

Thr Ile Ile Asn Cys Met Glu Asn Asn Ser Gly Trp Lys Val Ser Leu
            100                 105                 110

Asn Tyr Gly Glu Ile Ile Trp Thr Leu Gln Asp Thr Gln Glu Ile Lys
        115                 120                 125
```

```
Gln Arg Val Val Phe Lys Tyr Ser Gln Met Ile Asn Ile Ser Asp Tyr
130                 135                 140

Ile Asn Arg Trp Ile Phe Val Thr Ile Thr Asn Asn Arg Leu Asn Asn
145                 150                 155                 160

Ser Lys Ile Tyr Ile Asn Gly Arg Leu Ile Asp Gln Lys Pro Ile Ser
                165                 170                 175

Asn Leu Gly Asn Ile His Ala Ser Asn Asn Ile Met Phe Lys Leu Asp
                180                 185                 190

Gly Cys Arg Asp Thr His Arg Tyr Ile Trp Ile Lys Tyr Phe Asn Leu
                195                 200                 205

Phe Asp Lys Glu Leu Asn Glu Lys Glu Ile Lys Asp Leu Tyr Asp Asn
210                 215                 220

Gln Ser Asn Ser Gly Ile Leu Lys Asp Phe Trp Gly Asp Tyr Leu Gln
225                 230                 235                 240

Tyr Asp Lys Pro Tyr Tyr Met Leu Asn Leu Tyr Asp Pro Asn Lys Tyr
                245                 250                 255

Val Asp Val Asn Asn Val Gly Ile Arg Gly Tyr Met Tyr Leu Lys Gly
                260                 265                 270

Pro Arg Gly Ser Val Met Thr Thr Asn Ile Tyr Leu Asn Ser Ser Leu
                275                 280                 285

Tyr Arg Gly Thr Lys Phe Ile Ile Lys Lys Tyr Ala Ser Gly Asn Lys
290                 295                 300

Asp Asn Ile Val Arg Asn Asn Asp Arg Val Tyr Ile Asn Val Val Val
305                 310                 315                 320

Lys Asn Lys Glu Tyr Arg Leu Ala Thr Asn Ala Ser Gln Ala Gly Val
                325                 330                 335

Glu Lys Ile Leu Ser Ala Leu Glu Ile Pro Asp Val Gly Asn Leu Ser
                340                 345                 350

Gln Val Val Val Met Lys Ser Lys Asn Asp Gln Gly Ile Thr Asn Lys
                355                 360                 365

Cys Lys Met Asn Leu Gln Asp Asn Asn Gly Asn Asp Ile Gly Phe Ile
                370                 375                 380

Gly Phe His Gln Phe Asn Asn Ile Ala Lys Leu Val Ala Ser Asn Trp
385                 390                 395                 400

Tyr Asn Arg Gln Ile Glu Arg Ser Ser Arg Thr Leu Gly Cys Ser Trp
                405                 410                 415

Glu Phe Ile Pro Val Asp Asp Gly Trp Gly Glu Arg Pro Leu Arg Gly
                420                 425                 430

Arg Lys Arg Arg Ser Asp Asn Asn Leu Ile Asp Leu Ser Gly Tyr Gly
                435                 440                 445

Ala Lys Val Glu Val Tyr Asp Gly Val Glu Leu Asn Asp Lys Asn Gln
450                 455                 460

Phe Lys Leu Thr Ser Ser Ala Asn Ser Lys Ile Arg Val Thr Gln Asn
465                 470                 475                 480

Gln Asn Ile Ile Phe Asn Ser Val Phe Leu Asp Phe Ser Val Ser Phe
                485                 490                 495

Trp Ile Arg Ile Pro Lys Tyr Lys Asn Asp Gly Ile Gln Asn Tyr Ile
                500                 505                 510

His Asn Glu Tyr Thr Ile Ile Asn Cys Met Lys Asn Asn Ser Gly Trp
                515                 520                 525

Lys Ile Ser Ile Arg Gly Asn Arg Ile Ile Trp Thr Leu Ile Asp Ile
                530                 535                 540

Asn Gly Lys Thr Lys Ser Val Phe Phe Glu Tyr Asn Ile Arg Glu Asp
```

-continued

```
545                 550                 555                 560
Ile Ser Glu Tyr Ile Asn Arg Trp Phe Phe Val Thr Ile Thr Asn Asn
                565                 570                 575
Leu Asn Asn Ala Lys Ile Tyr Ile Asn Gly Lys Leu Glu Ser Asn Thr
                580                 585                 590
Asp Ile Lys Asp Ile Arg Glu Val Ile Ala Asn Gly Glu Ile Ile Phe
                595                 600                 605
Lys Leu Asp Gly Asp Ile Asp Arg Thr Gln Phe Ile Trp Met Lys Tyr
            610                 615                 620
Phe Ser Ile Phe Asn Thr Glu Leu Ser Gln Ser Asn Ile Glu Glu Arg
625                 630                 635                 640
Tyr Lys Ile Gln Ser Tyr Ser Glu Tyr Leu Lys Asp Phe Trp Gly Asn
                645                 650                 655
Pro Leu Met Tyr Asn Lys Glu Tyr Tyr Met Phe Asn Ala Gly Asn Lys
                660                 665                 670
Asn Ser Tyr Ile Lys Leu Lys Lys Asp Ser Pro Val Gly Glu Ile Leu
                675                 680                 685
Thr Arg Ser Lys Tyr Asn Gln Asn Ser Lys Tyr Ile Asn Tyr Arg Asp
            690                 695                 700
Leu Tyr Ile Gly Glu Lys Phe Ile Ile Arg Arg Lys Ser Asn Ser Gln
705                 710                 715                 720
Ser Ile Asn Asp Asp Ile Val Arg Lys Glu Asp Tyr Ile Tyr Leu Asp
                725                 730                 735
Phe Phe Asn Leu Asn Gln Glu Trp Arg Val Tyr Thr Tyr Lys Tyr Phe
                740                 745                 750
Lys Lys Glu Glu Glu Lys Leu Phe Leu Ala Pro Ile Ser Asp Ser Asp
            755                 760                 765
Glu Phe Tyr Asn Thr Ile Gln Ile Lys Glu Tyr Asp Glu Gln Pro Thr
            770                 775                 780
Tyr Ser Cys Gln Leu Leu Phe Lys Lys Asp Glu Glu Ser Thr Asp Glu
785                 790                 795                 800
Ile Gly Leu Ile Gly Ile His Arg Phe Tyr Glu Ser Gly Ile Val Phe
                805                 810                 815
Glu Glu Tyr Lys Asp Tyr Phe Cys Ile Ser Lys Trp Tyr Leu Lys Glu
                820                 825                 830
Val Lys Arg Lys Pro Tyr Asn Leu Lys Leu Gly Cys Asn Trp Gln Phe
            835                 840                 845
Ile Pro Lys Asp Glu Gly Trp Thr Glu Arg Gly Arg Lys Arg Arg Ser
850                 855                 860
Asp Lys Tyr Val Asp Thr Ser Gly Tyr Asp Ser Asn Ile Asn Ile Asn
865                 870                 875                 880
Gly Asp Val Tyr Lys Tyr Pro Thr Asn Lys Asn Gln Phe Gly Ile Tyr
                885                 890                 895
Asn Asp Lys Leu Ser Glu Val Asn Ile Ser Gln Asn Asp Tyr Ile Ile
                900                 905                 910
Tyr Asp Asn Lys Tyr Lys Asn Phe Ser Ile Ser Phe Trp Val Arg Ile
            915                 920                 925
Pro Asn Tyr Asp Asn Lys Ile Val Asn Val Asn Asn Glu Tyr Thr Ile
            930                 935                 940
Ile Asn Cys Met Arg Asp Asn Asn Ser Gly Trp Lys Val Ser Leu Asn
945                 950                 955                 960
His Asn Glu Ile Ile Trp Thr Leu Gln Asp Asn Ala Gly Ile Asn Gln
                965                 970                 975
```

```
Lys Leu Ala Phe Asn Tyr Gly Asn Ala Asn Gly Ile Ser Asp Tyr Ile
                980             985                 990

Asn Lys Trp Ile Phe Val Thr Ile  Thr Asn Asp Arg Leu  Gly Asp Ser
        995             1000                 1005

Lys Leu  Tyr Ile Asn Gly Asn  Leu Ile Asp Gln Lys  Ser Ile Leu
    1010             1015                 1020

Asn Leu  Gly Asn Ile His Val  Ser Asp Asn Ile Leu  Phe Lys Ile
    1025             1030                 1035

Val Asn  Cys Ser Tyr Thr Arg  Tyr Ile Gly Ile Arg  Tyr Phe Asn
    1040             1045                 1050

Ile Phe  Asp Lys Glu Leu Asp  Glu Thr Glu Ile Gln  Thr Leu Tyr
    1055             1060                 1065

Ser Asn  Glu Pro Asn Thr Asn  Ile Leu Lys Asp Phe  Trp Gly Asn
    1070             1075                 1080

Tyr Leu  Leu Tyr Asp Lys Glu  Tyr Tyr Leu Leu Asn  Val Leu Lys
    1085             1090                 1095

Pro Asn  Asn Phe Ile Asp Arg  Arg Lys Asp Ser Thr  Leu Ser Ile
    1100             1105                 1110

Asn Asn  Ile Arg Ser Thr Ile  Leu Leu Ala Asn Arg  Leu Tyr Ser
    1115             1120                 1125

Gly Ile  Lys Val Lys Ile Gln  Arg Val Asn Asn Ser  Ser Thr Asn
    1130             1135                 1140

Asp Asn  Leu Val Arg Lys Asn  Asp Gln Val Tyr Ile  Asn Phe Val
    1145             1150                 1155

Ala Ser  Lys Thr His Leu Phe  Pro Leu Tyr Ala Asp  Thr Ala Thr
    1160             1165                 1170

Thr Asn  Lys Glu Lys Thr Ile  Lys Ile Ser Ser Ser  Gly Asn Arg
    1175             1180                 1185

Phe Asn  Gln Val Val Val Met  Asn Ser Val Gly Asn  Asn Cys Thr
    1190             1195                 1200

Met Asn  Phe Lys Asn Asn Asn  Gly Asn Asn Ile Gly  Leu Leu Gly
    1205             1210                 1215

Phe Lys  Ala Asp Thr Val Val  Ala Ser Thr Trp Tyr  Tyr Thr His
    1220             1225                 1230

Met Arg  Asp His Thr Asn Ser  Asn Gly Cys Phe Trp  Asn Phe Ile
    1235             1240                 1245

Ser Glu  Glu His Gly Trp Gln  Glu Lys Arg Gly Arg  Lys Arg Arg
    1250             1255                 1260

Ser Asn  Asn Lys Phe Ile Asp  Ile Ser Gly Tyr Gly  Ser Asn Ile
    1265             1270                 1275

Ser Ile  Asn Gly Asp Val Tyr  Ile Tyr Ser Thr Asn  Arg Asn Gln
    1280             1285                 1290

Phe Gly  Ile Tyr Ser Ser Lys  Pro Ser Glu Val Asn  Ile Ala Gln
    1295             1300                 1305

Asn Asn  Asp Ile Ile Tyr Asn  Gly Arg Tyr Gln Asn  Phe Ser Ile
    1310             1315                 1320

Ser Phe  Trp Val Arg Ile Pro  Lys Tyr Phe Asn Lys  Val Asn Leu
    1325             1330                 1335

Asn Asn  Glu Tyr Thr Ile Ile  Asp Cys Ile Arg Asn  Asn Asn Ser
    1340             1345                 1350

Gly Trp  Lys Ile Ser Leu Asn  Tyr Asn Lys Ile Ile  Trp Thr Leu
    1355             1360                 1365
```

```
Gln Asp Thr Ala Gly Asn Asn Gln Lys Leu Val Phe Asn Tyr Thr
    1370            1375            1380

Gln Met Ile Ser Ile Ser Asp Tyr Ile Asn Lys Trp Ile Phe Val
    1385            1390            1395

Thr Ile Thr Asn Asn Arg Leu Gly Asn Ser Arg Ile Tyr Ile Asn
    1400            1405            1410

Gly Asn Leu Ile Asp Glu Lys Ser Ile Ser Asn Leu Gly Asp Ile
    1415            1420            1425

His Val Ser Asp Asn Ile Leu Phe Lys Ile Val Gly Cys Asn Asp
    1430            1435            1440

Thr Arg Tyr Val Gly Ile Arg Tyr Phe Lys Val Phe Asp Thr Glu
    1445            1450            1455

Leu Gly Lys Thr Glu Ile Glu Thr Leu Tyr Ser Asp Glu Pro Asp
    1460            1465            1470

Pro Ser Ile Leu Lys Asp Phe Trp Gly Asn Tyr Leu Leu Tyr Asn
    1475            1480            1485

Lys Arg Tyr Tyr Leu Leu Asn Leu Leu Arg Thr Asp Lys Ser Ile
    1490            1495            1500

Thr Gln Asn Ser Asn Phe Leu Asn Ile Asn Gln Gln Arg Gly Val
    1505            1510            1515

Tyr Gln Lys Pro Asn Ile Phe Ser Asn Thr Arg Leu Tyr Thr Gly
    1520            1525            1530

Val Glu Val Ile Ile Arg Lys Asn Gly Ser Thr Asp Ile Ser Asn
    1535            1540            1545

Thr Asp Asn Phe Val Arg Lys Asn Asp Leu Ala Tyr Ile Asn Val
    1550            1555            1560

Val Asp Arg Asp Val Glu Tyr Arg Leu Tyr Ala Asp Ile Ser Ile
    1565            1570            1575

Ala Lys Pro Glu Lys Ile Ile Lys Leu Ile Arg Thr Ser Asn Ser
    1580            1585            1590

Asn Asn Ser Leu Gly Gln Ile Ile Val Met Asp Ser Ile Gly Asn
    1595            1600            1605

Asn Cys Thr Met Asn Phe Gln Asn Asn Asn Gly Gly Asn Ile Gly
    1610            1615            1620

Leu Leu Gly Phe His Ser Asn Asn Leu Val Ala Ser Ser Trp Tyr
    1625            1630            1635

Tyr Asn Asn Ile Arg Lys Asn Thr Ser Ser Asn Gly Cys Phe Trp
    1640            1645            1650

Ser Phe Ile Ser Lys Glu His Gly Trp Gln Glu Asn
    1655            1660            1665
```

MONO OR MULTIVALENT BOTULINUM NEUROTOXIN BASED VACCINE USING THE HEAVY CHAIN FROM SEROTYPES OF *CLOSTRIDIUM BOTULINUM*

CROSS-REFERENCE TO RELATED APPLICATIONS

This application is the U.S. national stage application filed under 35U.S.C. §371 claiming benefit to International Patent Application No. PCT/US14/026974, filed Mar. 14, 2014, which is entitled to priority under 35 U.S.C. §119(e) to U.S. Provisional Application No. 61/799,094, filed Mar. 15, 2013, each of which is hereby incorporated by reference in its entirety.

TECHNICAL FIELD

Disclosed herein are compositions and methods for treating *Clostridium botulinum* neurotoxin intoxication and in particular, vaccines that provide protection against lethal challenge with one or more serotypes of *Clostridium botulinum*.

BACKGROUND

Botulism toxins are produced by the bacteria *Clostridium botulinum*, *C. butyricum*, *C. baratii* and *C. argentinense*. Foodborne botulism can be transmitted through food that has not been heated correctly prior to being canned or food that was not cooked correctly from a can. Most infant botulism cases cannot be prevented because the bacteria that cause this disease are in soil and dust. The bacteria can be found inside homes on floors, carpet, and countertops even after cleaning. Food-borne botulism usually results from ingestion of food that has become contaminated with spores (such as a perforated can) in an anaerobic environment, allowing the spores to germinate and grow. The growing (vegetative) bacteria produce toxin. It is the ingestion of toxin that causes botulism, not the ingestion of the spores or the vegetative bacteria. Infant and wound botulism both result from infection with spores, which subsequently germinate, resulting in production of toxin and the symptoms of botulism.

Botulinum toxin is a protein and neurotoxin produced by the bacterium *Clostridium botulinum*. Botulinum toxin can be absorbed from eyes, mucous membranes, respiratory tract or non-intact skin. It is the most acutely toxic substance known, with an estimated human median lethal dose of 1.3-2.1 ng/kg intravenously or intramuscularly and 10-13 ng/kg when inhaled. Botulinum neurotoxin (BoNT) intoxication results in a severe and potentially fatal neurological disease characterized by acute flaccid paralysis of motor and autonomic nerves. Human disease results from toxins produced by four serotypes of *Clostridium botulinum*: A, B, E, and F. Though botulinum poisoning is rare, the Center for Disease Control (CDC) has identified botulinum toxin as one of the six biggest threats for a bioterrorist attack on the United States of America. Currently, the only treatment for BoNT poisoning is delivery of an anti-serum, however, this requires rapid identification of BoNT poisoning as well as weeks to months of supportive care. The effectiveness of BoNT antiserum demonstrates that a BoNT vaccine inducing neutralizing antibodies can prevent disease upon exposure. An experimental pentavalent toxoid (A, B, C, D, E) vaccine previously available to military personnel and individuals employed in laboratory and manufacturing settings, who work with neurotoxin-producing species of *Clostridium*, has been discontinued by the CDC due to limited effectiveness and tolerability issues. In addition, a bivalent (A, B) recombinant toxoid vaccine is under investigation.

Accordingly, there remains a need for effective BoNT vaccines that produce broad immunity against one or more serotypes of *Clostridium botulinum*, including in particular, serotypes A, B, E, and/or F, and preferably, a universal vaccine that would be globally effective.

SUMMARY OF INVENTION

The present invention is directed to a vaccine comprising a nucleic acid encoding one or more amino acid sequence(s) selected from the group consisting of: heavy chain amino acid sequence of Botulinum A serotype neurotoxin (SEQ ID NO: 2); heavy chain amino acid sequence of Botulinum B serotype neurotoxin (SEQ ID NO: 4); heavy chain amino acid sequence of Botulinum E serotype neurotoxin (SEQ ID NO: 6); heavy chain amino acid sequence of Botulinum F serotype neurotoxin (SEQ ID NO: 8); an amino acid sequence that is 95% identical or greater to the heavy chain amino acid sequence of Botulinum A serotype neurotoxin (SEQ ID NO: 2); an amino acid sequence that is 95% identical or greater to the heavy chain amino acid sequence of Botulinum B serotype neurotoxin (SEQ ID NO: 4); an amino acid sequence that is 95% identical or greater to the heavy chain amino acid sequence of Botulinum E serotype neurotoxin (SEQ ID NO: 6); an amino acid sequence that is 95% identical or greater to the heavy chain amino acid sequence of Botulinum F serotype neurotoxin (SEQ ID NO: 8); an amino acid sequence that is 98% identical or greater to the heavy chain amino acid sequence of Botulinum A serotype neurotoxin (SEQ ID NO: 2); an amino acid sequence that is 98% identical or greater to the heavy chain amino acid sequence of Botulinum B serotype neurotoxin (SEQ ID NO: 4); an amino acid sequence that is 98% identical or greater to the heavy chain amino acid sequence of Botulinum E serotype neurotoxin (SEQ ID NO: 6); and an amino acid sequence that is 98% identical or greater to the heavy chain amino acid sequence of Botulinum F serotype neurotoxin (SEQ ID NO: 8).

The nucleic acid molecule may comprise one or more nucleotide sequences selected from the group consisting of: SEQ ID NO:1, SEQ ID NO:3, SEQ ID NO:5, and SEQ ID NO:7. The nucleic acid molecule may be a plasmid. The nucleic acid may be one or more plasmids. The vaccine may further comprise an adjuvant molecule. The adjuvant can be IL-1, IL-2, IL-4, IL-5, IL-6, IL-8, IL-10, IL-12, IL-15, IL-18, IL-28, RANTES, TNF-α, TNF-β, GM-CSF, MCP-1, MIP-1a, MIP-1p, CD34, TRAIL, RANK, Ox40, TAP-1, or TAP-2. In particular, the adjuvant can be IL-12, IL-15, IL-28, or RANTES.

The present invention is also directed to a monovalent vaccine or a multivalent vaccine, for example, but not limited to, a bivalent vaccine, a trivalent vaccine, a quadravalent or tetravalent vaccine, and a pentavalent vaccine. The vaccine can include a single plasmid or multiple plasmids that encode for 1, 2, 3, 4 or more neurotoxins or fragments thereof from one or more serotypes of *Clostridium botulinum*. Fragments can include for example, but are not limited to, a light chain and/or a heavy chain of one or more neurotoxins from one or more serotypes of *Clostridium botulinum*. The multiple plasmids can be for example, but are not limited to, 1, 2, 3, 4, or more plasmids.

The present invention is also directed to a method of inducing an immune response against a Botulinum neurotoxin comprising administering any of the above described vaccines to a subject. Administration may include electroporation.

The present invention is further directed to method of protecting a subject from botulinum poisoning comprising administering any of the above described vaccines to a subject. Administration may include electroporation.

The present invention is directed to a nucleic acid molecule comprising, one or more nucleotide sequences selected from the group consisting of: SEQ ID NO:1, SEQ ID NO:3, SEQ ID NO:5, SEQ ID NO:7, a nucleotide sequence that is 95% identical or greater to SEQ ID NO:1, a nucleotide sequence that is 95% identical or greater to SEQ ID NO:3, a nucleotide sequence that is 95% identical or greater to SEQ ID NO:5, a nucleotide sequence that is 95% identical or greater to SEQ ID NO:7, a nucleotide sequence that is 98% identical or greater to SEQ ID NO:1, a nucleotide sequence that is 98% identical or greater to SEQ ID NO:3, a nucleotide sequence that is 98% identical or greater to SEQ ID NO:5, and a nucleotide sequence that is 98% identical or greater to SEQ ID NO:7.

The nucleotide sequence may be a plasmid. The one or more nucleotide sequences may be one or more plasmids. The one or more nucleotide sequences may encode for one or more amino acid sequences selected from the group consisting of: SEQ ID NO:2, SEQ ID NO:4, SEQ ID NO:6, SEQ ID NO:8, SEQ ID NO:9, SEQ ID NO:10, SEQ ID NO:11, an amino acid sequence 95% identical or greater to SEQ ID NO:2, an amino acid sequence 95% identical or greater to SEQ ID NO:4, an amino acid sequence 95% identical or greater to SEQ ID NO:6, an amino acid sequence 95% identical or greater to SEQ ID NO:8, an amino acid sequence 95% identical or greater to SEQ ID NO:9, an amino acid sequence 95% identical or greater to SEQ ID NO:10, an amino acid sequence 95% identical or greater to SEQ ID NO:11, an amino acid sequence 98% identical or greater to SEQ ID NO:4, an amino acid sequence 98% identical or greater to SEQ ID NO:6, an amino acid sequence 98% identical or greater to SEQ ID NO:8, an amino acid sequence 98% identical or greater to SEQ ID NO:9, an amino acid sequence 98% identical or greater to SEQ ID NO:10, and an amino acid sequence 98% identical or greater to SEQ ID NO:11.

BRIEF DESCRIPTION OF THE DRAWINGS

FIGS. 1A-C illustrate construction of monovalent, bivalent, and quadravalent or tetravalent botulinum neurotoxin (BoNT) heavy chain (Hc) plasmids or expression vectors, respectively.

FIG. 2 shows representative in vitro expression of botulinum neurotoxin heavy chain from the monovalent expression vectors BoNT/Hc/A, BoNT/Hc/B, BoNT/Hc/E, and BoNT/Hc/F and the vector pVAX, which was used as a negative control.

FIGS. 3A-C show humoral responses to BoNT Hc vaccines.

FIGS. 4A-C show BoNT Hc vaccines protecting against lethal challenge with *Clostridium botulinum* neurotoxin.

FIG. 5 shows a schematic illustrating a schedule for vaccination, blood and tissue collection, and challenge with neurotoxin.

FIG. 6 shows immunoglobulin G (IgG) titer in collected sera that was reactive to (A) neurotoxin from *Clostridium botulinum* serotype A; (B) neurotoxin from *Clostridium botulinum* serotype B; and (c) neurotoxin from *Clostridium botulinum* serotype E.

FIG. 7 shows (A) a graph plotting time (hours) post-inoculation with neurotoxin from *Clostridium botulinum* serotype A against percent survival; and (B) a graph plotting mouse against clinical score for symptoms of intoxication. In FIG. 7A, triangle, square, and circle represented mice immunized with BoNT/Hc/A, naïve mice, and mice receiving the diluent Gel-Na$_2$PO$_4$, respectively. In FIG. 7A, the immunized and naïve mice were challenged with the neurotoxin, but mice receiving the diluent served as a negative control and were not challenged with the neurotoxin.

FIG. 8 shows (A) a graph plotting time (hours) post-inoculation with neurotoxin from *Clostridium botulinum* serotype B against percent survival; and (B) a graph plotting mouse against clinical score for symptoms of intoxication. In FIG. 8A, triangle, square, and circle represented mice immunized with BoNT/Hc/B, naïve mice, and mice receiving the diluent Gel-Na$_2$PO$_4$, respectively. In FIG. 8A, the immunized and naïve mice were challenged with the neurotoxin, but mice receiving the diluent served as a negative control and were not challenged with the neurotoxin.

FIG. 9 shows (A) a graph plotting time (hours) post-inoculation with neurotoxin from *Clostridium botulinum* serotype E against percent survival; and (B) a graph plotting mouse against clinical score for symptoms of intoxication. In FIG. 9A, triangle, square, and circle represented mice immunized with BoNT/Hc/E, naïve mice, and mice receiving the diluent Gel-Na$_2$PO$_4$, respectively. In FIG. 9A, the immunized and naïve mice were challenged with the neurotoxin, but mice receiving the diluent served as a negative control and were not challenged with the neurotoxin.

FIG. 10 shows (A) a schematic illustrating a trivalent vaccine that was a mixture of the BoNT/Hc/A, BoNT/Hc/B, and BoNT/Hc/E constructs; (B) IgG titer in collected sera that was reactive to neurotoxin from *Clostridium botulinum* serotype A; (C) IgG titer in collected sera that was reactive to neurotoxin from *Clostridium botulinum* serotype B; and (D) IgG titer in collected sera that was reactive to neurotoxin from *Clostridium botulinum* serotype E.

FIG. 11 shows (A) a graph plotting time (hours) post-inoculation with neurotoxin from *Clostridium botulinum* serotype A against percent survival; (B) a graph plotting mouse against clinical score for symptoms of intoxication; (C) a graph plotting time (hours) post-inoculation with neurotoxin from *Clostridium botulinum* serotype B against percent survival; (D) a graph plotting mouse against clinical score for symptoms of intoxication; (E) a graph plotting time (hours) post-inoculation with neurotoxin from *Clostridium botulinum* serotype E against percent survival; and (F) a graph plotting mouse against clinical score for symptoms of intoxication. In FIGS. 11A, 11C, and 11E, triangle represented mice immunized with BoNT/Hc/A, BoNT/Hc/B, and BoNT/Hc/E, respectively. Also in FIGS. 11A, 11C, and 11E, square and circle represented naïve mice and mice receiving the diluent Gel-Na$_2$PO$_4$, respectively. In FIGS. 11A, 11C, and 11E, the immunized and naïve mice were challenged with the neurotoxin, but mice receiving the diluent served as a negative control and were not challenged with the neurotoxin.

FIG. 12 shows (A) a schematic illustrating formation of the sera:toxin mixture; (B) a graph plotting time (hours) post-inoculation with sera:neurotoxin from *Clostridium botulinum* serotype A against percent survival; (C) a graph plotting time (hours) post-inoculation with sera:neurotoxin from *Clostridium botulinum* serotype B against percent survival; (D) a graph plotting time (hours) post-inoculation with sera:neurotoxin from *Clostridium botulinum* serotype E against percent survival; (E-G) graphs plotting mouse against clinical score for symptoms of intoxication. In FIGS. 12B, 12C, and 12D, triangle represented mice receiving the following mixtures: sera from BoNT/Hc/A immunized mice:neurotoxin from serotype A, sera from BoNT/Hc/B immunized mice:neurotoxin from serotype B, and sera from BoNT/Hc/E immunized mice:neurotoxin from serotype E, respectively. In FIGS. 12B, 12C, and 12D, square and circle represented naïve mice and mice receiving the diluent Gel-Na$_2$PO$_4$, respectively. In FIGS. 12B, 12C, and 12D, mice receiving the diluent did not receive a sera:toxin mixture.

FIG. 13 shows a schematic illustrating construction of a quadravalent or tetravalent botulinum neurotoxin (BoNT) heavy chain (Hc) plasmids or expression vector containing BoNT-A, BoNT-B, BoNT-E, and BoNT-F.

DETAILED DESCRIPTION

The present invention is directed to the use of neurotoxin proteins from *Clostridium botulinum*. The neurotoxin proteins can be from one or more serotypes of *Clostridium botulinum*. The one or more serotypes of *Clostridium botulinum* can be A, B, C$_1$, C$_2$, D, E, F, and/or G. In some embodiments, the one or more serotypes of *Clostridium botulinum* can be A, B, E and/or F.

The present invention is also directed to the use of heavy chain neurotoxin proteins from *Clostridium botulinum*, for example, those from serotypes A, B, C$_1$, C$_2$, D, E, F, and/or G. In some embodiments, the heavy chain neurotoxin proteins can be from serotypes A, B, E, and/or F of *Clostridium botulinum*. These botulinum neurotoxin (BoNT) heavy chain (Hc) DNA vaccines induce humoral immunogenicity and provide protection against lethal challenge with *Clostridium botulinum* neurotoxin, demonstrating at least a 50% protection, and preferably 60%, 65%, 75%, 80%, 85%, 90%, 95%, or 100% protection, and more preferably 75% or 100% protection against lethal challenge after vaccination with our monovalent or trivalent and bivalent BoNT Hc vaccine constructs, respectively. The induced humoral immunogenicity includes induction of neutralizing antibodies that are reactive to the neurotoxin from *Clostridium botulinum* serotypes. In addition, by targeting the botulinum toxin serotypes A, B, E, and/or F, which are largely responsible for human disease, the present invention vaccines of monovalent, bivalent, trivalent and quadravalent constructs offer enhanced protection over the current experimental DNA vaccines, which only demonstrate efficacy against serotypes A and B.

1. Definitions

The terminology used herein is for the purpose of describing particular embodiments only and is not intended to be limiting. Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments or derivatives thereof, including Fab, F(ab')2, Fd, and single chain antibodies, diabodies, bispecific antibodies, bifunctional antibodies and derivatives thereof. The antibody can be an antibody isolated from the serum sample of a mammal, a polyclonal antibody, an affinity purified antibody, or mixtures thereof, which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple subtypes of a particular BoNT Hc antigen(s). Nucleic acid sequences that encode a consensus polypeptide sequence can be prepared. Vaccines comprising proteins that comprise consensus sequences and/or nucleic acid molecules that encode such proteins can be used to induce broad immunity against multiple subtypes or serotypes of a particular antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof that encodes a polypeptide capable of eliciting an immune response in a mammal that cross reacts with a full length wild type strain antigen. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with a full length wild type strain antigen. Fragments of proteins or consensus proteins can comprise at least 10%, at least 20%, at least 30%, at least 40%, at least 50%, at least 60%, at least 70%, at least 80%, at least 90% or at least 95% of a protein or consensus protein. In some embodiments, fragments of proteins or consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein or consensus protein set forth below.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

The term "homology" as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

"Optimized" as used herein with respect to nucleic acid sequences means a nucleic acid sequence is modified with regards to codon usage and corresponding RNA transcripts for improved expression of the encoded protein as compared to the unmodified nucleic acid sequence. Additional modifications of the nucleic acid sequence can include addition of a Kozak sequence (e.g., GCC ACC) to increase the efficiency of translation and multiple stop codons (e.g., TGA TGA) to increase the efficiency of translation termination.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to the cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of an antigenic protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Subject" as used herein can mean a mammal that wants to or is in need of being immunized with the herein described vaccines. The mammal can be a human, chimpanzee, dog, cat, horse, cow, mouse, or rat.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

2. Vaccine

The present invention is directed to a *Clostridium botulinum* neurotoxin (BoNT) vaccine. BoNT can cause botulism in mammals and is a two-chain polypeptide with a 100-kDa heavy chain joined by a disulfide bond to a 50-kDa light chain. The heavy chain provides cholinergic specificity (i.e., targeting of specific axons or nerve endings), binding of the toxin to presynaptic membranes, and promotes translocation of the light chain across the endosomal membrane. Upon endocytosis of the neurotoxin, the disulfide bond linking the heavy and light chains is cleaved, thereby releasing the light chain into the cytoplasm. The light chain is an enzyme (a protease) that attacks or cleaves one of the fusion proteins found at a neuromuscular junction (e.g., SNAP-25, syntaxin, or synaptobrevin), preventing vesicles from anchoring to the membrane to release acetylcholine. Acetylcholine is the principal neurotransmitter found at neuromuscular junctions, but is also found at autonomic ganglia, postganglionic parasympathetic nerve endings, and postganglionic sympathetic nerve endings, and thus, BoNT also targets these types of neurons. By preventing acetylcholine release, BoNT causes flaccid paralysis of muscles in the mammal exposed to BoNT. The BoNT from serotypes A, B, E, and F of *Clostridium botulinum* can affect acetylcholine release and thus, cause intoxication or disease (i.e., botulism), symptoms of which include flaccid paralysis, respiratory distress, respiratory failure, and impaired motor function. Serotypes $C_1$, $C_2$, D, and G of *Clostridium botulinum* also produce toxin.

Accordingly, the BoNT vaccine comprises one or more neurotoxin antigens from *Clostridium botulinum*. The neurotoxin antigens can be from one or more serotypes of *Clostridium botulinum*. The one or more serotypes of *Clostridium botulinum* can be A, B, $C_1$, $C_2$, D, E, F, and/or G. In some embodiments, the one or more serotypes of *Clostridium botulinum* can be A, B, E and/or F.

In some embodiments, the neurotoxin antigens can be heavy chain neurotoxin proteins from *Clostridium botulinum*, for example, those from serotypes A, B, $C_1$, $C_2$, D, E, F, and/or G. In some embodiments, the heavy chain neurotoxin proteins can be from serotypes A, B, E, and/or F of *Clostridium botulinum*. The BoNT vaccine can be directed to the heavy chain polypeptide sequence for *Clostridium botulinum* serotypes A, B, E, and/or F.

The BoNT vaccine can comprise a nucleic acid encoding one or more of a BoNT antigen from *Clostridium botulinum* serotype A (BoNT-A), a BoNT antigen from *Clostridium botulinum* serotype B (BoNT-B), a BoNT antigen from *Clostridium botulinum* serotype $C_1$ (BoNT-$C_1$), a BoNT antigen from *Clostridium botulinum* serotype $C_2$ (BoNT-$C_2$), a BoNT antigen from *Clostridium botulinum* serotype D (BoNT-D), a BoNT antigen from *Clostridium botulinum* serotype E (BoNT-E), a BoNT antigen from *Clostridium botulinum* serotype F (BoNT-F), a BoNT antigen from *Clostridium botulinum* serotype G (BoNT-G), or combinations thereof. The nucleic acid can be a heterologous nucleic acid and/or include one or more heterologous nucleic acid sequences.

In some embodiments, the vaccine can comprise a nucleic acid encoding one or more of a BoNT antigen from *Clostridium botulinum* serotype A (BoNT-A), a BoNT antigen from *Clostridium botulinum* serotype B (BoNT-B), a BoNT antigen from *Clostridium botulinum* serotype E (BoNT-E), a BoNT antigen from *Clostridium botulinum* serotype F (BoNT-F), or combinations thereof. The nucleic acid can be a heterologous nucleic acid and/or include one or more heterologous nucleic acid sequences.

In other embodiments, the BoNT vaccine can comprise an optimized nucleic acid encoding one or more of a BoNT antigen from *Clostridium botulinum* serotype A (BoNT-A), a BoNT antigen from *Clostridium botulinum* serotype B (BoNT-B), a BoNT antigen from *Clostridium botulinum* serotype $C_1$ (BoNT-$C_1$), a BoNT antigen from *Clostridium botulinum* serotype $C_2$ (BoNT-$C_2$), a BoNT antigen from *Clostridium botulinum* serotype D (BoNT-D), a BoNT antigen from *Clostridium botulinum* serotype E (BoNT-E), a BoNT antigen from *Clostridium botulinum* serotype F (BoNT-F), a BoNT antigen from *Clostridium botulinum* serotype G (BoNT-G), or combinations thereof. The optimized nucleic acid can be a heterologous nucleic acid and/or include one or more heterologous nucleic acid sequences.

In some embodiments, the BoNT vaccine can comprise an optimized nucleic acid encoding one or more of a BoNT antigen from *Clostridium botulinum* serotype A (BoNT-A), a BoNT antigen from *Clostridium botulinum* serotype B (BoNT-B), a BoNT antigen from *Clostridium botulinum* serotype E (BoNT-E), a BoNT antigen from *Clostridium botulinum* serotype F (BoNT-F) or combinations thereof. The optimized nucleic acid can be a heterologous nucleic acid and/or include one or more heterologous nucleic acid sequences.

In other embodiments, the BoNT vaccine can comprise one or more heterologous nucleic acids encoding one or more of a BoNT antigen from *Clostridium botulinum* serotype A (BoNT-A), a BoNT antigen from *Clostridium botulinum* serotype B (BoNT-B), a BoNT antigen from Clostridium botulinum serotype $C_1$ (BoNT-$C_1$), a BoNT antigen from Clostridium botulinum serotype $C_2$ (BoNT-$C_2$), a BoNT antigen from Clostridium botulinum serotype D (BoNT-D), a BoNT antigen from Clostridium botulinum serotype E (BoNT-E), a BoNT antigen from Clostridium botulinum serotype F (BoNT-F), a BoNT antigen from Clostridium botulinum serotype G (BoNT-G), or combinations thereof.

In some embodiments, the BoNT vaccine can comprise one or more heterologous nucleic acids encoding one or more of a BoNT antigen from Clostridium botulinum serotype A (BoNT-A), a BoNT antigen from Clostridium botulinum serotype B (BoNT-B), a BoNT antigen from Clostridium botulinum serotype E (BoNT-E), a BoNT antigen from Clostridium botulinum serotype F (BoNT-F) or combinations thereof.

The BoNT-A antigen can comprise a consensus protein derived from the amino acid sequences of the heavy chains of BoNT from multiple C. botulinum A serotypes. The BoNT-B antigen can comprise a consensus protein derived from the amino acid sequences of the heavy chains of BoNT from multiple C. botulinum B serotypes. The BoNT-$C_1$ antigen can comprise a consensus protein derived from the amino acid sequences of the heavy chains of BoNT from multiple C. botulinum $C_1$ serotypes. The BoNT-$C_2$ antigen can comprise a consensus protein derived from the amino acid sequences of the heavy chains of BoNT from multiple C. botulinum $C_2$ serotypes. The BoNT-D antigen can comprise a consensus protein derived from the amino acid sequences of the heavy chains of BoNT from multiple C. botulinum D serotypes. The BoNT-E antigen can comprise a consensus protein derived from the amino acid sequences of the heavy chains of BoNT from multiple C. botulinum E serotypes. The BoNT-F antigen can comprise a consensus protein derived from the amino acid sequences of the heavy chains of BoNT from multiple C. botulinum F serotypes. The BoNT-G antigen can comprise a consensus protein derived from the amino acid sequences of the heavy chains from multiple C. botulinum G serotypes.

As such, the vaccine of the present invention can generate immune response that is cross-reactive to multiple serotypes of Clostridium botulinum and is useful for widespread populations against numerous insults to a subject such as nature based infections, food-borne illnesses and bioterrorism attacks. Additionally, the vaccine of the present invention can be tailored to particular nucleic acids encoding one or more amino acids sequences for BoNT-A, BoNT-B, BoNT-$C_1$, BoNT-$C_2$, BoNT-D, BoNT-E, BoNT-F, BoNT-G, or a combination thereof, in particular, BoNT-A, BoNT-B, BoNT-E, BoNT-F, or a combination thereof. In other embodiments, the vaccine of the present invention can be tailored to particular nucleic acids encoding one or more consensus based amino acid sequences for BoNT-A, BoNT-B, BoNT-$C_1$, BoNT-$C_2$, BoNT-D, BoNT-E, BoNT-F, BoNT-G, or a combination thereof, in particular, BoNT-A, BoNT-B, BoNT-E, BoNT-F, or a combination thereof. In other words, the vaccine of the present invention is designed to provide a nucleic acid or DNA or an optimized nucleic acid or DNA platform to produce broad immunity against neurotoxin from one or more serotypes of Clostridium botulinum.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the BoNT-A, BoNT-B, BoNT-$C_1$, BoNT-$C_2$, BoNT-D, BoNT-E, BoNT-F, BoNT-G, or a combination thereof, in particular, an RNA of the BoNT-A, BoNT-B, BoNT-E, BoNT-F, or a combination thereof. The RNA vaccine can be introduced into the cell.

The vaccine induces humoral immunogenicity and provides protection against lethal challenge with Clostridium botulinum neurotoxin, providing 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% protection against lethal challenge after vaccination with monovalent construct or multivalent construct, for example, but not limited to, bivalent, trivalent, or tetravalent BoNT vaccine constructs, as described below. The monovalent or trivalent BoNT vaccine constructs can provide 100% protection against lethal challenge after vaccination as described below. The humoral immunogenicity induced by the vaccine of the present invention includes induction of neutralizing antibodies that mediate the protection against lethal challenge with Clostridium botulinum neurotoxin.

a. BoNT-A

The vaccine of the present invention can comprise an antigen from Clostridium botulinum of serotype A (BoNT-A). The BoNT-A is an important target for immune mediated response by inducing (1) humoral immunity via B cell responses; (2) cytotoxic T lymphocyte (CTL) responses, and (3) T helper cell responses, or preferably all of the aforementioned, for cross presentation. The BoNT-A antigen induces antigen-specific T-cell and high titer antibody responses both systemically and in the neurological system. The BoNT-A antigen induces neutralizing antibodies that protect against lethal doses of Clostridium botulinum neurotoxin. These neutralizing antibodies protect against lethal doses of the neurotoxin from Clostridium botulinum serotype A.

The BoNT-A antigen can comprise protein epitopes that make them particularly effective as immunogens against which anti-BoNT-A immune responses can be induced. The BoNT-A antigen can comprise the full length translation product, a variant thereof, a fragment thereof, or a combination thereof. The BoNT-A antigen can comprise the heavy chain of BoNT-A, the light chain of BoNT-A, a variant thereof, a fragment thereof, or a combination thereof. The BoNT-A antigen can be encoded by an optimized nucleic acid and/or can comprise a consensus protein as described below in more detail. Accordingly, any user can design a vaccine of the present invention to include a BoNT-A antigen or BoNT-A consensus antigen (either or both of which may be encoded by a nucleic acid in the vaccine) to provide broad immunity against Clostridium botulinum neurotoxin A serotypes. As such, a protective immune response is provided to the neurological system by vaccines comprising a nucleic acid encoding the BoNT-A antigen, a nucleic acid encoding the BoNT-A consensus antigen, the BoNT-A antigen, BoNT-A consensus antigen, or a combination thereof.

(1) Optimized BoNT-A

The BoNT-A antigen can be encoded by an optimized nucleic acid sequence. This optimized nucleic acid sequence can be a heterologous nucleic acid sequence and/or include one or more heterologous nucleic acid sequences. An immunoglobulin E (IgE) leader sequence can be located at the N-terminus of or linked to the BoNT-A antigen, and thus, the optimized nucleic acid can also encode the IgE leader sequence. In other embodiments, IgE leader sequence may not be located at the N-terminus of or linked to the BoNT-A antigen, and thus, the optimized nucleic acid does not contain or is free of a nucleotide sequence encoding the IgE leader sequence. In still other embodiments, the BoNT-A amino acid sequence may be linked to the IgE leader sequence and an HA tag, and thus, the optimized nucleic acid can also encode the IgE leader sequence and HA tag.

The optimized nucleic acid SEQ ID NO:1 encodes the BoNT-A antigen (SEQ ID NO:2). In particular, SEQ ID NO:1 encodes the BoNT-A antigen linked to an IgE leader sequence (SEQ ID NO:2). Furthermore, the amino acid sequence of the BoNT-A protein is SEQ ID NO:2. The amino acid sequence of the BoNT-A protein linked to an IgE leader is SEQ ID NO:2. The amino acid sequence of the BoNT-A protein linked to the IgE leader may also be linked to an HA tag.

In some embodiments, the nucleic acid encoding BoNT-A can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:1. In some embodiments, the nucleic acid encoding BoNT-A can be the nucleic acid sequence set forth in SEQ ID NO:1. In other embodiments, the nucleic acid encoding the BoNT-A antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. In still other embodiments, the BoNT-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. In other embodiments, the BoNT-A antigen can be the amino acid sequence set forth in SEQ ID NO:2.

Some embodiments relate to fragments of SEQ ID NO:1. Fragments can be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% of SEQ ID NO:1. Fragments can be at least 95%, at least 96%, at least 97%, at least 98%, or at least 99% homologous to fragments of SEQ ID NO:1. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:1. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein.

Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a protein disclosed herein include sequences encoding an IgE leader sequence linked to the 5' end of the coding sequence encoding the homologous protein sequences disclosed herein.

Some embodiments relate to nucleic acid sequences encoding proteins homologous to the BoNT-A protein, immunogenic fragment of the BoNT-A protein, and immunogenic fragments of homologous proteins. Such nucleic acid molecules that encode immunogenic proteins that have up to 95% homology to a BoNT-A amino acid sequence, up to 96% homology to a BoNT-A amino acid sequence, up to 96% homology to a BoNT-A amino acid sequence, up to 97% homology to a BoNT-A amino acid sequence, up to 98% homology to a BoNT-A amino acid sequence and up to 99% homology to a BoNT-A amino acid sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-A protein, immunogenic fragment of the BoNT-A protein, and immunogenic fragments of proteins having identity to the BoNT-A protein. Such nucleic acid molecules that encode immunogenic proteins that have up to 80% identity to a full length BoNT-A amino acid sequence, up to 85% identity to a full length BoNT-A amino acid sequence, up to 90% identity to a full length BoNT-A amino acid sequence, up to 91% identity to a full length BoNT-A amino acid sequence, up to 92% identity to a full length BoNT-A amino acid sequence, up to 93% identity to a full length BoNT-A amino acid sequence, up to 94% identity to a full length BoNT-A amino acid sequence, up to 95% identity to a full length BoNT-A amino acid sequence, up to 96% identity to a full length BoNT-A amino acid sequence, up to 97% identity to a full length BoNT-A amino acid sequence, up to 98% identity to a full length BoNT-A amino acid sequence, and up to 99% identity to a full length BoNT-A amino acid sequence can be provided. Likewise, nucleic acid sequences encoding the immunogenic fragments set forth herein and the immunogenic fragments of proteins with similar percent identities as indicated above to the BoNT-A proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to proteins that are homologous to SEQ ID NO:2. Some embodiments relate to immunogenic proteins that have 95% homology to the protein sequences as set forth in SEQ ID NO:2. Some embodiments relate to immunogenic proteins that have 96% homology to the protein sequences as set forth in SEQ ID NO:2. Some embodiments relate to immunogenic proteins that have 97% homology to the protein sequences as set forth in SEQ ID NO:2. Some embodiments relate to immunogenic proteins that have 98% homology to the protein sequences as set forth in SEQ ID NO:2. Some embodiments relate to immunogenic proteins that have 99% homology to the protein sequences as set forth in SEQ ID NO:2.

Some embodiments relate to proteins that are identical to SEQ ID NO:2. Some embodiments relate to immunogenic proteins that have an amino acid sequence that is 80% identical to the full length amino acid sequences as set forth in SEQ ID NO:2. Some embodiments relate to immunogenic proteins that have an amino acid sequence that is 85% identical to the full length amino acid sequences as set forth in SEQ ID NO:2. Some embodiments relate to immunogenic proteins that have an amino acid sequence that is 90% identical to the full length amino acid sequences as set forth in SEQ ID NO:2. Some embodiments relate to immunogenic proteins that have an amino acid sequence that is 91% identical to the full length amino acid sequences as set forth in SEQ ID NO:2. Some embodiments relate to immunogenic proteins that have an amino acid sequence that is 92% identical to the full length amino acid sequences as set forth in SEQ ID NO:2. Some embodiments relate to immunogenic proteins that have an amino acid sequence that is 93% identical to the full length amino acid sequences as set forth in SEQ ID NO:2. Some embodiments relate to immunogenic proteins that have an amino acid sequence that is 94% identical to the full length amino acid sequences as set forth in SEQ ID NO:2. Some embodiments relate to immunogenic proteins that have an amino acid sequence that is 95% identical to the full length amino acid sequences as set forth in SEQ ID NO:2. Some embodiments relate to immunogenic proteins that have an amino acid sequence that is 96% identical to the full length amino acid sequences as set forth in SEQ ID NO:2. Some embodiments relate to immunogenic proteins that have an amino acid sequence that is 97% identical to the full length amino acid sequences as set forth in SEQ ID NO:2. Some embodiments relate to immunogenic proteins that have an amino acid sequence that is 98% identical to the full length amino acid sequences as set forth in SEQ ID NO:2. Some embodiments relate to immunogenic proteins that have an amino acid sequence that is 99% identical to the full length amino acid sequences as set forth in SEQ ID NO:2.

In some embodiments, the protein is free of a leader sequence. In some embodiments, the protein is free of the IgE leader. Fragments of BoNT-A proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-A protein. Immunogenic fragments of SEQ ID NO:2 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:2. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein, which is encoded by the start codon of the nucleic acid sequence that encodes the protein without a signal peptide coding sequence(s).

(2) Consensus BoNT-A

The BoNT-A antigen can include a consensus protein derived from the amino acid sequences of the heavy chains of neurotoxin from multiple *Clostridium botulinum* A serotypes. Some embodiments relate to nucleic acid sequences encoding proteins homologous to the BoNT-A consensus protein, immunogenic fragment of the BoNT-A consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% homology to a consensus sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-A consensus protein, immunogenic fragment of the BoNT-A consensus protein, and immunogenic fragments of proteins having identity to the BoNT-A consensus protein. Such nucleic acid molecules that encode immunogenic proteins that have up to 80% identity to a full length BoNT-A consensus sequence, up to 85% identity to a full length BoNT-A consensus sequence, up to 90% identity to a full length BoNT-A consensus sequence, up to 91% identity to a full length BoNT-A consensus sequence, up to 92% identity to a full length BoNT-A consensus sequence, up to 93% identity to a full length BoNT-A consensus sequence, up to 94% identity to a full length BoNT-A consensus sequence, up to 95% identity to a full length BoNT-A consensus sequence, up to 96% identity to a full length BoNT-A consensus sequence, up to 97% identity to a full length BoNT-A consensus sequence, up to 98% identity to a full length BoNT-A consensus sequence, and up to 99% identity to a full length BoNT-A consensus sequence can be provided. Likewise, nucleic acid sequences encoding the immunogenic fragments set forth herein and the immunogenic fragments of proteins with similar percent identities as indicated above to the BoNT-A proteins set forth herein are also provided.

In some embodiments, the nucleic acid sequence is free of coding sequence that encodes a leader sequence. In some embodiments, the nucleic acid sequence is free of coding sequence that encodes the IgE leader.

In some embodiments, the BoNT-A consensus protein is free of a leader sequence. In some embodiments, the BoNT-A consensus protein is free of the IgE leader. In other embodiments, the BoNT-A consensus protein can include a leader sequence, for example, but not limited to, an IgE leader sequence. Proteins having at least about 80%, 81%, 82%, 83%, 84%, 85%, 86%, 87%, 88%, 89%, 90%, 91%, 92%, 93%, 94%, 95%, 96%, 97%, 98%, or 99% identity to the BoNT-A consensus protein are also provided.

Fragments of BoNT-A consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-A consensus protein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% identity to the immunogenic fragments of consensus protein sequences herein. Some embodiments relate to immunogenic fragments that have 97% identity to the immunogenic fragments of consensus protein sequences herein. Some embodiments relate to immunogenic fragments that have 98% identity to the immunogenic fragments of consensus protein sequences herein. Some embodiments relate to immunogenic fragments that have 99% identity to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

b. BoNT-B

The vaccine of the present invention can comprise an antigen from *Clostridium botulinum* of serotype B (BoNT-B). The BoNT-B is an important target for immune mediated response by inducing (1) humoral immunity via B cell responses; (2) cytotoxic T lymphocyte (CTL) responses, and (3) T helper cell responses, or preferably all of the aforementioned, for cross presentation. The BoNT-B antigen induces antigen-specific T-cell and high titer antibody responses both systemically and in the neurological system. The BoNT-B antigen induces neutralizing antibodies that protect against lethal doses of *Clostridium botulinum* neurotoxin. These neutralizing antibodies protect against lethal doses of the neurotoxin from *Clostridium botulinum* serotype B.

The BoNT-B antigen can comprise protein epitopes that make them particularly effective as immunogens against which anti-BoNT-B immune responses can be induced. The BoNT-B antigen can comprise the full length translation product, a variant thereof, a fragment thereof, or a combination thereof. The BoNT-B antigen can comprise the heavy chain of BoNT-B, the light chain of BoNT-B, a variant thereof, a fragment thereof, or a combination thereof. The BoNT-B antigen can be encoded by an optimized nucleic acid and/or can comprise a consensus protein as described below in more detail. Accordingly, any user can design a vaccine of the present invention to include a BoNT-B antigen or BoNT-B consensus antigen (either or both of which may be encoded by a nucleic acid in the vaccine) to provide broad immunity against *Clostridium botulinum* neurotoxin B serotypes. As such, a protective immune response is provided to the neurological system by vaccines comprising a nucleic acid encoding the BoNT-B antigen, a nucleic acid encoding the BoNT-B consensus antigen, the BoNT-B antigen, BoNT-B consensus antigen, or a combination thereof.

(1) Optimized BoNT-B

The BoNT-B antigen can be encoded by an optimized nucleic acid sequence. This optimized nucleic acid sequence can be a heterologous nucleic acid sequence and/or include one or more heterologous nucleic acid sequences. An immunoglobulin E (IgE) leader sequence can be located at the N-terminus of or linked to the BoNT-B antigen, and thus, the optimized nucleic acid can also encode the IgE leader sequence. In other embodiments, the IgE leader sequence may not be located at the N-terminus of or linked to the BoNT-B antigen, and thus, the optimized nucleic acid does not contain or is free of a nucleotide sequence encoding the IgE leader sequence. In still other embodiments, the BoNT-B amino acid sequence may be linked to the IgE leader sequence and an HA tag, and thus, the optimized nucleic acid can also encode the IgE leader sequence and HA tag.

The optimized nucleic acid SEQ ID NO:3 encodes the BoNT-B antigen (SEQ ID NO:4). In particular, SEQ ID NO:3 encodes the BoNT-B antigen linked to an IgE leader sequence (SEQ ID NO:4). Furthermore, the amino acid sequence of the BoNT-B protein is SEQ ID NO:4. The amino acid sequence of the BoNT-B protein linked to an IgE leader is SEQ ID NO:4. The amino acid sequence of the BoNT-B protein linked to the IgE leader may also be linked to HA tag.

In some embodiments, the nucleic acid encoding BoNT-B can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:3. In some embodiments, the nucleic acid encoding BoNT-B can be the nucleic acid sequence set forth in SEQ ID NO:3. In other embodiments, the nucleic acid encoding the BoNT-B antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. In still other embodiments, the BoNT-B antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. In other embodiments, the BoNT-B antigen can be the amino acid sequence set forth in SEQ ID NO:4.

Some embodiments relate to fragments of SEQ ID NO:3. Fragments can be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% of SEQ ID NO:3. Fragments can be at least 95%, at least 96%, at least 97%, at least 98%, or at least 99% homologous to fragments of SEQ ID NO:3. Fragments can be at least 80%, at least 85%, at least 90%, at least 91%, at least 92%, at least 93%, at least 94%, at least 95%, at least 96%, at least 97%, at least 98%, or at least 99% identical to fragments of SEQ ID NO:3. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a protein disclosed herein include sequences encoding an IgE leader sequence linked to the 5' end of the coding sequence encoding the homologous protein sequences disclosed herein.

Some embodiments relate to nucleic acid sequences encoding proteins homologous to the BoNT-B protein, immunogenic fragment of the BoNT-B protein, and immunogenic fragments of homologous proteins. Such nucleic acid molecules that encode immunogenic proteins that have up to 95% homology to a BoNT-B amino acid sequence, up to 96% homology to a BoNT-B amino acid sequence, up to 96% homology to a BoNT-B amino acid sequence, up to 97% homology to a BoNT-B amino acid sequence, up to 98% homology to a BoNT-B amino acid sequence and up to 99% homology to a BoNT-B amino acid sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-B protein, immunogenic fragment of the BoNT-B protein, and immunogenic fragments of proteins having identity to the BoNT-B protein. Such nucleic acid molecules that encode immunogenic proteins that have up to 80% identity to a full length BoNT-B amino acid sequence, up to 85% identity to a full length BoNT-B amino acid sequence, up to 90% identity to a full length BoNT-B amino acid sequence, up to 91% identity to a full length BoNT-B amino acid sequence, up to 92% identity to a full length BoNT-B amino acid sequence, up to 93% identity to a full length BoNT-B amino acid sequence, up to 94% identity to a full length BoNT-B amino acid sequence, up to 95% identity to a full length BoNT-B amino acid sequence, up to 96% identity to a full length BoNT-B amino acid sequence, up to 97% identity to a full length BoNT-B amino acid sequence, up to 98% identity to a full length BoNT-B amino acid sequence, and up to 99% identity to a full length BoNT-B amino acid sequence can be provided. Likewise, nucleic acid sequences encoding the immunogenic fragments set forth herein and the immunogenic fragments of proteins with similar percent identities as indicated above to the BoNT-B proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to proteins that are homologous to SEQ ID NO:4. Some embodiments relate to immunogenic proteins that have 95% homology to the protein sequences as set forth in SEQ ID NO:4. Some embodiments relate to immunogenic proteins that have 96% homology to the protein sequences as set forth in SEQ ID NO:4. Some embodiments relate to immunogenic proteins that have 97% homology to the protein sequences as set forth in SEQ ID NO:4. Some embodiments relate to immunogenic proteins that have 98% homology to the protein sequences as set forth in SEQ ID NO:4. Some embodiments relate to immunogenic proteins that have 99% homology to the protein sequences as set forth in SEQ ID NO:4.

Some embodiments relate to proteins that are identical to SEQ ID NO:4. Some embodiments relate to immunogenic proteins that have an amino acid sequence that is 80% identical to the full length amino acid sequences as set forth in SEQ ID NO:4. Some embodiments relate to immunogenic proteins that have an amino acid sequence that is 85% identical to the full length amino acid sequences as set forth in SEQ ID NO:4. Some embodiments relate to immunogenic proteins that have an amino acid sequence that is 90% identical to the full length amino acid sequences as set forth in SEQ ID NO:4. Some embodiments relate to immunogenic proteins that have an amino acid sequence that is 91% identical to the full length amino acid sequences as set forth in SEQ ID NO:4. Some embodiments relate to immunogenic proteins that have an amino acid sequence that is 92% identical to the full length amino acid sequences as set forth in SEQ ID NO:4. Some embodiments relate to immunogenic proteins that have an amino acid sequence that is 93% identical to the full length amino acid sequences as set forth in SEQ ID NO:4. Some embodiments relate to immunogenic proteins that have an amino acid sequence that is 94% identical to the full length amino acid sequences as set forth in SEQ ID NO:4. Some embodiments relate to immunogenic proteins that have an amino acid sequence that is 95% identical to the full length amino acid sequences as set forth in SEQ ID NO:4. Some embodiments relate to immunogenic proteins that have an amino acid sequence that is 96% identical to the full length amino acid sequences as set forth in SEQ ID NO:4. Some embodiments relate to immunogenic proteins that have an amino acid sequence that is 97% identical to the full length amino acid sequences as set forth in SEQ ID NO:4. Some embodiments relate to immunogenic proteins that have an amino acid sequence that is 98% identical to the full length amino acid sequences as set forth in SEQ ID NO:4. Some embodiments relate to immunogenic proteins that have an amino acid sequence that is 99% identical to the full length amino acid sequences as set forth in SEQ ID NO:4.

In some embodiments, the protein is free of a leader sequence. In some embodiments, the protein is free of the IgE leader. Fragments of BoNT-B proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-B protein. Immunogenic fragments of SEQ ID NO:4 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:4. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein, which is encoded by the start codon of the nucleic acid sequence that encodes the protein without a signal peptide coding sequence(s).

(2) Consensus BoNT-B

The BoNT-B antigen can include a consensus protein derived from the amino acids sequences of the heavy chains of neurotoxin from multiple *Clostridium botulinum* B serotypes. Some embodiments relate to nucleic acid sequences encoding proteins homologous to the BoNT-B consensus protein, immunogenic fragment of the BoNT-B consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% homology to a consensus sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-B consensus protein, immunogenic fragment of the BoNT-B consensus protein, and immunogenic fragments of proteins having identity to the BoNT-B consensus protein. Such nucleic acid molecules that encode immunogenic proteins that have up to 80% identity to a full length BoNT-B consensus sequence, up to 85% identity to a full length consensus sequence, up to 90% identity to a full length BoNT-B consensus sequence, up to 91% identity to a full length BoNT-B consensus sequence, up to 92% identity to a full length BoNT-B consensus sequence, up to 93% identity to a full length BoNT-B consensus sequence, up to 94% identity to a full length BoNT-B consensus sequence, up to 95% identity to a full length BoNT-B consensus sequence, up to 96% identity to a full length BoNT-B consensus sequence, up to 97% identity to a full length BoNT-B consensus sequence, up to 98% identity to a full length BoNT-B consensus sequence, and up to 99% identity to a full length BoNT-B consensus sequence can be provided. Likewise, nucleic acid sequences encoding the immunogenic fragments set forth herein and the immunogenic fragments of proteins with similar percent identities as indicated above to the BoNT-B proteins set forth herein are also provided.

In some embodiments, the nucleic acid sequence is free of coding sequence that encodes a leader sequence. In some embodiments, the nucleic acid sequence is free of coding sequence that encodes the IgE leader.

In some embodiments, the BoNT-B consensus protein is free of a leader sequence. In some embodiments, the BoNT-B consensus protein is free of the IgE leader. In other embodiments, the BoNT-B consensus protein can include a leader sequence, for example, but not limited to, an IgE leader sequence. Proteins having at least about 80%, 81%, 82%, 83%, 84%, 85%, 86%, 87%, 88%, 89%, 90%, 91%, 92%, 93%, 94%, 95%, 96%, 97%, 98%, or 99% identity to the BoNT-B consensus protein are also provided.

Fragments of BoNT-B consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-B consensus protein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% identity to the immunogenic fragments of consensus protein sequences herein. Some embodiments relate to immunogenic fragments that have 97% identity to the immunogenic fragments of consensus protein sequences herein. Some embodiments relate to immunogenic fragments that have 98% identity to the immunogenic fragments of consensus protein sequences herein. Some embodiments relate to immunogenic fragments that have 99% identity to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

c. BoNT-E

The vaccine of the present invention can comprise an antigen from *Clostridium botulinum* of serotype E (BoNT-E). The BoNT-E is an important target for immune mediated response by inducing (1) humoral immunity via B cell responses; (2) cytotoxic T lymphocyte (CTL) responses, and (3) T helper cell responses, or preferably all of the aforementioned, for cross presentation. The BoNT-E antigen induces antigen-specific T-cell and high titer antibody responses both systemically and in the neurological system. The BoNT-E antigen induces neutralizing antibodies that protect against lethal doses of *Clostridium botulinum* neurotoxin. These neutralizing antibodies protect against lethal doses of the neurotoxin from *Clostridium botulinum* serotype E.

The BoNT-E antigen can comprise protein epitopes that make them particularly effective as immunogens against which anti-BoNT-E immune responses can be induced. The BoNT-E antigen can comprise the full length translation product, a variant thereof, a fragment thereof, or a combination thereof. The BoNT-E antigen can comprise the heavy chain of BoNT-E, the light chain of BoNT-E, a variant thereof, a fragment thereof, or a combination thereof. The BoNT-E antigen can be encoded by an optimized nucleic acid and/or can comprise a consensus protein as described below in more detail. Accordingly, any user can design a vaccine of the present invention to include a BoNT-E antigen or BoNT-E consensus antigen (either or both of which may be encoded by a nucleic acid in the vaccine) to provide broad immunity against *Clostridium botulinum* neurotoxin E serotypes. As such, a protective immune response is provided to the neurological system by vaccines comprising a nucleic acid encoding the BoNT-E antigen, a nucleic acid encoding the BoNT-E consensus antigen, the BoNT-E antigen, BoNT-E consensus antigen, or a combination thereof.

(1) Optimized BoNT-E

The BoNT-E antigen can be encoded by an optimized nucleic acid sequence. This optimized nucleic acid sequence can be a heterologous nucleic acid sequence and/or include one or more heterologous nucleic acid sequences. An immunoglobulin E (IgE) leader sequence can be located at the N-terminus of or linked to the BoNT-E antigen, and thus, the optimized nucleic acid can also encode the IgE leader sequence. In other embodiments, IgE leader sequence may not be located at the N-terminus of or linked to the BoNT-E antigen, and thus, the optimized nucleic acid does not contain or is free of a nucleotide sequence encoding the IgE leader sequence. In still other embodiments, the BoNT-E amino acid sequence may be linked to the IgE leader sequence and an HA tag, and thus, the optimized nucleic acid can also encode the IgE leader sequence and HA tag.

The optimized nucleic acid SEQ ID NO:5 encodes the BoNT-E antigen (SEQ ID NO:6). In particular, SEQ ID NO:5 encodes the BoNT-E antigen linked to an IgE leader sequence (SEQ ID NO:6). Furthermore, the amino acid sequence of the BoNT-E protein is SEQ ID NO:6. The amino acid sequence of the BoNT-E protein linked to an IgE leader is SEQ ID NO:6. The amino acid sequence of the BoNT-E protein linked to the IgE leader may also be linked to HA tag.

In some embodiments, the nucleic acid encoding BoNT-E can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:5. In some embodiments, the nucleic acid encoding BoNT-E can be the nucleic acid sequence set forth in SEQ ID NO:5. In other embodiments, the nucleic acid encoding the BoNT-E antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. In still other embodiments, the BoNT-E antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. In other embodiments, the BoNT-E antigen can be the amino acid sequence set forth in SEQ ID NO:6.

Some embodiments relate to fragments of SEQ ID NO:5. Fragments can be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% of SEQ ID NO:5. Fragments can be at least 95%, at least 96%, at least 97%, at least 98%, or at least 99% homologous to fragments of SEQ ID NO:5. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:5. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a protein disclosed herein include sequences encoding an IgE leader sequence linked to the 5' end of the coding sequence encoding the homologous protein sequences disclosed herein.

Some embodiments relate to nucleic acid sequences encoding proteins homologous to the BoNT-E protein, immunogenic fragment of the BoNT-E protein, and immunogenic fragments of homologous proteins. Such nucleic acid molecules that encode immunogenic proteins that have up to 95% homology to a BoNT-E amino acid sequence, up to 96% homology to a BoNT-E amino acid sequence, up to 96% homology to a BoNT-E amino acid sequence, up to 97% homology to a BoNT-E amino acid sequence, up to 98% homology to a BoNT-E amino acid sequence and up to 99% homology to a BoNT-E amino acid sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-E protein, immunogenic fragment of the BoNT-E protein, and immunogenic fragments of proteins having identity to the BoNT-E protein. Such nucleic acid molecules that encode immunogenic proteins that have up to 80% identity to a full length BoNT-E amino acid sequence, up to 85% identity to a full length BoNT-E amino acid sequence, up to 90% identity to a full length BoNT-E amino acid sequence, up to 91% identity to a full length BoNT-E amino acid sequence, up to 92% identity to a full length BoNT-E amino acid sequence, up to 93% identity to a full length BoNT-E amino acid sequence, up to 94% identity to a full length BoNT-E amino acid sequence, up to 95% identity to a full length BoNT-E amino acid sequence, up to 96% identity to a full length BoNT-E amino acid sequence, up to 97% identity to a full length BoNT-E amino acid sequence, up to 98% identity to a full length BoNT-E amino acid sequence, and up to 99% identity to a full length BoNT-E amino acid sequence can be provided. Likewise, nucleic acid sequences encoding the immunogenic fragments set forth herein and the immunogenic fragments of proteins with similar percent identities as indicated above to the BoNT-E proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to proteins that are homologous to SEQ ID NO:6. Some embodiments relate to immunogenic proteins that have 95% homology to the protein sequences as set forth in SEQ ID NO:6. Some embodiments relate to immunogenic proteins that have 96% homology to the protein sequences as set forth in SEQ ID NO:6. Some embodiments relate to immunogenic proteins that have 97% homology to the protein sequences as set forth in SEQ ID NO:6. Some embodiments relate to immunogenic proteins that have 98% homology to the protein sequences as set forth in SEQ ID NO:6. Some embodiments relate to immunogenic proteins that have 99% homology to the protein sequences as set forth in SEQ ID NO:6.

Some embodiments relate to proteins that are identical to SEQ ID NO:6. Some embodiments relate to immunogenic proteins that have an amino acid sequence that is 80% identical to the full length amino acid sequences as set forth in SEQ ID NO:6. Some embodiments relate to immunogenic proteins that have an amino acid sequence that is 85% identical to the full length amino acid sequences as set forth in SEQ ID NO:6. Some embodiments relate to immunogenic proteins that have an amino acid sequence that is 90% identical to the full length amino acid sequences as set forth in SEQ ID NO:6. Some embodiments relate to immunogenic proteins that have an amino acid sequence that is 91% identical to the full length amino acid sequences as set forth in SEQ ID NO:6. Some embodiments relate to immunogenic proteins that have an amino acid sequence that is 92% identical to the full length amino acid sequences as set forth in SEQ ID NO:6. Some embodiments relate to immunogenic proteins that have an amino acid sequence that is 93% identical to the full length amino acid sequences as set forth in SEQ ID NO:6. Some embodiments relate to immunogenic proteins that have an amino acid sequence that is 94% identical to the full length amino acid sequences as set forth in SEQ ID NO:6. Some embodiments relate to immunogenic proteins that have an amino acid sequence that is 95% identical to the full length amino acid sequences as set forth in SEQ ID NO:6. Some embodiments relate to immunogenic proteins that have an amino acid sequence that is 96% identical to the full length amino acid sequences as set forth in SEQ ID NO:6. Some embodiments relate to immunogenic proteins that have an amino acid sequence that is 97% identical to the full length amino acid sequences as set forth in SEQ ID NO:6. Some embodiments relate to immunogenic proteins that have an amino acid sequence that is 98% identical to the full length amino acid sequences as set forth in SEQ ID NO:6. Some embodiments relate to immunogenic proteins that have an amino acid sequence that is 99% identical to the full length amino acid sequences as set forth in SEQ ID NO:6.

In some embodiments, the protein is free of a leader sequence. In some embodiments, the protein is free of the IgE leader. Fragments of BoNT-E proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-E protein. Immunogenic fragments of SEQ ID NO:6 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:6. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein, which is encoded by the start codon of the nucleic acid sequence that encodes the protein without a signal peptide coding sequence(s).

(2) Consensus BoNT-E

The BoNT-E antigen can include a consensus protein derived from the amino acids sequences of the heavy chains of neurotoxin from multiple *Clostridium botulinum* E serotypes. Some embodiments relate to nucleic acid sequences encoding proteins homologous to the BoNT-E consensus protein, immunogenic fragment of the BoNT-E consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% homology to a consensus sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-E consensus protein, immunogenic fragment of the BoNT-E consensus protein, and immunogenic fragments of proteins having identity to the BoNT-E consensus protein. Such nucleic acid molecules that encode immunogenic proteins that have up to 80% identity to a full length BoNT-E consensus sequence, up to 85% identity to a full length BoNT-E consensus sequence, up to 90% identity to a full length BoNT-E consensus sequence, up to 91% identity to a full length BoNT-E consensus sequence, up to 92% identity to a full length BoNT-E consensus sequence, up to 93% identity to a full length BoNT-E consensus sequence, up to 94% identity to a full length BoNT-E consensus sequence, up to 95% identity to a full length BoNT-E consensus sequence, up to 96% identity to a full length BoNT-E consensus sequence, up to 97% identity to a full length BoNT-E consensus sequence, up to 98% identity to a full length BoNT-E consensus sequence, and up to 99% identity to a full length BoNT-E consensus sequence can be provided. Likewise, nucleic acid sequences encoding the immunogenic fragments set forth herein and the immunogenic fragments of proteins with similar percent identities as indicated above to the BoNT-E proteins set forth herein are also provided.

In some embodiments, the nucleic acid sequence is free of coding sequence that encodes a leader sequence. In some embodiments, the nucleic acid sequence is free of coding sequence that encodes the IgE leader.

In some embodiments, the BoNT-E consensus protein is free of a leader sequence. In some embodiments, the BoNT-E consensus protein is free of the IgE leader. In other embodiments, the BoNT-E consensus protein can include a leader sequence, for example, but not limited to, an IgE leader sequence. Proteins having at least about 80%, 81%, 82%, 83%, 84%, 85%, 86%, 87%, 88%, 89%, 90%, 91%, 92%, 93%, 94%, 95%, 96%, 97%, 98%, or 99% identity to the BoNT-E consensus protein are also provided.

Fragments of BoNT-E consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-E consensus protein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% identity to the immunogenic fragments of consensus protein sequences herein. Some embodiments relate to immunogenic fragments that have 97% identity to the immunogenic fragments of consensus protein sequences herein. Some embodiments relate to immunogenic fragments that have 98% identity to the immunogenic fragments of consensus protein sequences herein. Some embodiments relate to immunogenic fragments that have 99% identity to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

d. BoNT-F

The vaccine of the present invention can comprise an antigen from *Clostridium botulinum* of serotype F (BoNT-F). The BoNT-F is an important target for immune mediated response by inducing (1) humoral immunity via B cell responses; (2) cytotoxic T lymphocyte (CTL) responses, and (3) T helper cell responses, or preferably all of the aforementioned, for cross presentation. The BoNT-F antigen induces antigen-specific T-cell and high titer antibody responses both systemically and in the neurological system. The BoNT-F antigen induces neutralizing antibodies that protect against lethal doses of *Clostridium botulinum* neurotoxin. These neutralizing antibodies protect against lethal doses of the neurotoxin from *Clostridium botulinum* serotype F.

The BoNT-F antigen can comprise protein epitopes that make them particularly effective as immunogens against which anti-BoNT-F immune responses can be induced. The BoNT-F antigen can comprise the full length translation product, a variant thereof, a fragment thereof, or a combination thereof. The BoNT-F antigen can comprise the heavy chain of BoNT-F, the light chain of BoNT-F, a variant thereof, a fragment thereof, or a combination thereof. The BoNT-F antigen can be encoded by an optimized nucleic acid and/or can comprise a consensus protein as described below in more detail. Accordingly, any user can design a vaccine of the present invention to include a BoNT-F antigen or BoNT-F consensus antigen (either or both of which may be encoded by a nucleic acid in the vaccine) to provide broad immunity against *Clostridium botulinum* neurotoxin F serotypes. As such, a protective immune response is provided to the neurological system by vaccines comprising a nucleic acid encoding the BoNT-F antigen, a nucleic acid encoding the BoNT-F consensus antigen, the BoNT-F antigen, BoNT-F consensus antigen, or a combination thereof.

(1) Optimized BoNT-F

The BoNT-F antigen can be encoded by an optimized nucleic acid sequence. This optimized nucleic acid sequence can be a heterologous nucleic acid sequence and/or include one or more heterologous nucleic acid sequences. An immunoglobulin E (IgE) leader sequence can be located at the N-terminus of or linked to the BoNT-F antigen, and thus, the optimized nucleic acid can also encode the IgE leader sequence. In other embodiments, IgE leader sequence may not be located at the N-terminus of or linked to the BoNT-F antigen, and thus, the optimized nucleic acid does not contain or is free of a nucleotide sequence encoding the IgE leader sequence. In still other embodiments, the BoNT-F amino acid sequence may be linked to the IgE leader sequence and an HA tag, and thus, the optimized nucleic acid can also encode the IgE leader sequence and HA tag.

The optimized nucleic acid SEQ ID NO:7 encodes the BoNT-F antigen (SEQ ID NO:8). In particular, SEQ ID NO:7 encodes the BoNT-F antigen linked to an IgE leader sequence (SEQ ID NO:8). Furthermore, the amino acid sequence of the BoNT-F protein is SEQ ID NO:8. The amino acid sequence of the BoNT-F protein linked to an IgE leader is SEQ ID NO:8. The amino acid sequence of the BoNT-F protein linked to the IgE leader may also be linked to an HA tag.

In some embodiments, the nucleic acid encoding BoNT-F can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:7. In some embodiments, the nucleic acid encoding BoNT-F can be the nucleic acid sequence set forth in SEQ ID NO:7. In other embodiments, the nucleic acid encoding the BoNT-F antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. In still other embodiments, the BoNT-F antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. In other embodiments, the BoNT-F antigen can be the amino acid sequence set forth in SEQ ID NO:8.

Some embodiments relate to fragments of SEQ ID NO:7. Fragments can be at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% of SEQ ID NO:7. Fragments can be at least 95%, at least 96%, at least 97%, at least 98%, or at least 99% homologous to fragments of SEQ ID NO:7. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:7. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a protein disclosed herein include sequences encoding an IgE leader sequence linked to the 5' end of the coding sequence encoding the homologous protein sequences disclosed herein.

Some embodiments relate to nucleic acid sequences encoding proteins homologous to the BoNT-F protein, immunogenic fragment of the BoNT-F protein, and immunogenic fragments of homologous proteins. Such nucleic acid molecules that encode immunogenic proteins that have up to 95% homology to a BoNT-F amino acid sequence, up to 96% homology to a BoNT-F amino acid sequence, up to 96% homology to a BoNT-F amino acid sequence, up to 97% homology to a BoNT-F amino acid sequence, up to 98% homology to a BoNT-F amino acid sequence and up to 99% homology to a BoNT-F amino acid sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-F protein, immunogenic fragment of the BoNT-F protein, and immunogenic fragments of proteins having identity to the BoNT-F protein. Such nucleic acid molecules that encode immunogenic proteins that have up to 80% identity to a full length BoNT-F amino acid sequence, up to 85% identity to a full length BoNT-F amino acid sequence, up to 90% identity to a full length BoNT-F amino acid sequence, up to 91% identity to a full length BoNT-F amino acid sequence, up to 92% identity to a full length BoNT-F amino acid sequence, up to 93% identity to a full length BoNT-F amino acid sequence, up to 94% identity to a full length BoNT-F amino acid sequence, up to 95% identity to a full length BoNT-F amino acid sequence, up to 96% identity to a full length BoNT-F amino acid sequence, up to 97% identity to a full length BoNT-F amino acid sequence, up to 98% identity to a full length BoNT-F amino acid sequence, and up to 99% identity to a full length BoNT-F amino acid sequence can be provided. Likewise, nucleic acid sequences encoding the immunogenic fragments set forth herein and the immunogenic fragments of proteins with similar percent identities as indicated above to the BoNT-F proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to proteins that are homologous to SEQ ID NO:8. Some embodiments relate to immunogenic proteins that have 95% homology to the protein sequences as set forth in SEQ ID NO:8. Some embodiments relate to immunogenic proteins that have 96% homology to the protein sequences as set forth in SEQ ID NO:8. Some embodiments relate to immunogenic proteins that have 97% homology to the protein sequences as set forth in SEQ ID NO:8. Some embodiments relate to immunogenic proteins that have 98% homology to the protein sequences as set forth in SEQ ID NO:8. Some embodiments relate to immunogenic proteins that have 99% homology to the protein sequences as set forth in SEQ ID NO:8.

Some embodiments relate to proteins that are identical to SEQ ID NO:8. Some embodiments relate to immunogenic proteins that have an amino acid sequence that is 80% identical to the full length amino acid sequences as set forth in SEQ ID NO:8. Some embodiments relate to immunogenic proteins that have an amino acid sequence that is 85% identical to the full length amino acid sequences as set forth in SEQ ID NO:8. Some embodiments relate to immunogenic proteins that have an amino acid sequence that is 90% identical to the full length amino acid sequences as set forth in SEQ ID NO:8. Some embodiments relate to immunogenic proteins that have an amino acid sequence that is 91% identical to the full length amino acid sequences as set forth in SEQ ID NO:8. Some embodiments relate to immunogenic proteins that have an amino acid sequence that is 92% identical to the full length amino acid sequences as set forth in SEQ ID NO:8. Some embodiments relate to immunogenic proteins that have an amino acid sequence that is 93% identical to the full length amino acid sequences as set forth in SEQ ID NO:8. Some embodiments relate to immunogenic proteins that have an amino acid sequence that is 94% identical to the full length amino acid sequences as set forth in SEQ ID NO:8. Some embodiments relate to immunogenic proteins that have an amino acid sequence that is 95% identical to the full length amino acid sequences as set forth in SEQ ID NO:8. Some embodiments relate to immunogenic proteins that have an amino acid sequence that is 96% identical to the full length amino acid sequences as set forth in SEQ ID NO:8. Some embodiments relate to immunogenic proteins that have an amino acid sequence that is 97% identical to the full length amino acid sequences as set forth in SEQ ID NO:8. Some embodiments relate to immunogenic proteins that have an amino acid sequence that is 98% identical to the full length amino acid sequences as set forth in SEQ ID NO:8. Some embodiments relate to immunogenic proteins that have an amino acid sequence that is 99% identical to the full length amino acid sequences as set forth in SEQ ID NO:8.

In some embodiments, the protein is free of a leader sequence. In some embodiments, the protein is free of the IgE leader. Fragments of BoNT-F proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-F protein. Immunogenic fragments of SEQ ID NO:8 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:8. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein, which is encoded by the start codon of the nucleic acid sequence that encodes the protein without a signal peptide coding sequence(s).

(2) Consensus BoNT-F

The BoNT-F antigen can include a consensus protein derived from the amino acids sequences of the heavy chains of neurotoxin from multiple *Clostridium botulinum* F serotypes. Some embodiments relate to nucleic acid sequences encoding proteins homologous to the BoNT-F consensus protein, immunogenic fragment of the BoNT-F consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% homology to a consensus sequence can be provided. Likewise, nucleic acid sequences encoding the immunogenic fragments set forth herein and the immunogenic fragments of proteins homologous to the proteins set forth herein are also provided.

Some embodiments relate to nucleic acid sequences encoding proteins with a particular percent identity to the full length BoNT-F consensus protein, immunogenic fragment of the BoNT-F consensus protein, and immunogenic fragments of proteins having identity to the BoNT-F consensus protein. Such nucleic acid molecules that encode immunogenic proteins that have up to 80% identity to a full length BoNT-F consensus sequence, up to 85% identity to a full length BoNT-F consensus sequence, up to 90% identity to a full length BoNT-F consensus sequence, up to 91% identity to a full length BoNT-F consensus sequence, up to 92% identity to a full length BoNT-F consensus sequence, up to 93% identity to a full length BoNT-F consensus sequence, up to 94% identity to a full length BoNT-F consensus sequence, up to 95% identity to a full length BoNT-F consensus sequence, up to 96% identity to a full length BoNT-F consensus sequence, up to 97% identity to a full length BoNT-F consensus sequence, up to 98% identity to a full length BoNT-F consensus sequence, and up to 99% identity to a full length BoNT-F consensus sequence can be provided. Likewise, nucleic acid sequences encoding the immunogenic fragments set forth herein and the immunogenic fragments of proteins with similar percent identities as indicated above to the BoNT-F proteins set forth herein are also provided.

In some embodiments, the nucleic acid sequence is free of coding sequence that encodes a leader sequence. In some embodiments, the nucleic acid sequence is free of coding sequence that encodes the IgE leader.

In some embodiments, the BoNT-F consensus protein is free of a leader sequence. In some embodiments, the BoNT-F consensus protein is free of the IgE leader. In other embodiments, the BoNT-F consensus protein can include a leader sequence, for example, but not limited to, an IgE leader sequence. Proteins having at least about 80%, 81%, 82%, 83%, 84%, 85%, 86%, 87%, 88%, 89%, 90%, 91%, 92%, 93%, 94%, 95%, 96%, 97%, 98%, or 99% identity to the BoNT-F consensus protein are also provided.

Fragments of BoNT-F consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a BoNT-F consensus protein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Some embodiments relate to immunogenic fragments that have 96% identity to the immunogenic fragments of consensus protein sequences herein. Some embodiments relate to immunogenic fragments that have 97% identity to the immunogenic fragments of consensus protein sequences herein. Some embodiments relate to immunogenic fragments that have 98% identity to the immunogenic fragments of consensus protein sequences herein. Some embodiments relate to immunogenic fragments that have 99% identity to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

3. Vaccine Combinations of BoNT Antigens

The vaccine can comprise a combination of one or more of the BoNT antigens described above. In some embodiments, the combination can be a combination of one or more of the BoNT-A, BoNT-B, BoNT-$C_1$, BoNT-$C_2$, Bo-NTD, BoNT-E, BoNT-F, and BoNT-G antigens described above. The combinations of BoNT antigens are capable of eliciting an immune response in a mammal against one or more *Clostridium botulinum* serotypes, and in some embodiments, against one or more of serotypes A, B, E, and/or F. The vaccine can be designed or tailored to have a particular combination of BoNT antigens, which in turn, provides the ability to control the level or strength of an immune response in the mammal. The designed or tailored vaccine can also provide the user with the ability to control the reactivity (i.e., reactive against neurotoxin from one or more serotypes of *Clostridium botulinum*) of the neutralizing antibodies that are induced by the vaccine.

In some embodiments, the combinations can comprise two nucleic acids encoding in any order may include (1) BoNT-A and BoNT-B, (2) BoNT-A and BoNT-$C_1$, (3) BoNT-A and BoNT-$C_2$, (4) BoNT-A and BoNT-D, (5) BoNT-A and BoNT-E, (6) BoNT-A and BoNT-F, (7) BoNT-A and BoNT-G, (8) BoNT-B and BoNT-$C_1$, (9) BoNT-B and BoNT-$C_2$, (10) BoNT-B and BoNT-D, (11) BoNT-B and BoNT-E, (12) BoNT-B and BoNT-F, (13) BoNT-B and BoNT-G, (14) BoNT-$C_1$ and BoNT-$C_2$, (15) BoNT-$C_1$ and BoNT-D, (16) BoNT-$C_1$ and BoNT-E, (17) BoNT-$C_1$ and BoNT-F, and (18) BoNT-$C_1$ and BoNT-G, (19) BoNT-$C_2$ and BoNT-D, (20), BoNT-$C_2$ and BoNT-E, (21) BoNT-$C_2$ and BoNT-F, (22) BoNT-$C_2$ and BoNT-G, (23) BoNT-D and BoNT-E, (24) BoNT-E and BoNT-F, (25) BoNT-D and BoNT-G, (26) BoNT-E and BoNT-F, (27) BoNT-E and BoNT-G, and (28) BoNT-F and BoNT-G.

An exemplary embodiment relates to a vaccine including one or more nucleic acids encoding one or more of BoNT-A, BoNT-B, BoNT-$C_1$, BoNT-$C_2$, Bo-NTD, BoNT-E, BoNT-F, and BoNT-G in any order. Yet another exemplary embodiment relates to a vaccine including one or more nucleic acids encoding one or more BoNT-A, BoNT-B, BoNT-$C_1$, BoNT-$C_2$, Bo-NTD, BoNT-E, BoNT-F, and BoNT-G in any order, and adjuvant such as IL-12. Other possible adjuvants are described in more detail below.

The combinational vaccine also comprises one or more BoNT-A, BoNT-B, BoNT-$C_1$, BoNT-$C_2$, Bo-NTD, BoNT-E, BoNT-F, and BoNT-G protein, one or more consensus BoNT-A, BoNT-B, BoNT-$C_1$, BoNT-$C_2$, Bo-NTD, BoNT-E, BoNT-F, and BoNT-G protein, one or more killed viral particles comprising one or more BoNT-A, BoNT-B, BoNT-$C_1$, BoNT-$C_2$, Bo-NTD, BoNT-E, BoNT-F, and BoNT-G, one or more killed viral particles comprising one or more consensus BoNT-A, BoNT-B, BoNT-$C_1$, BoNT-$C_2$, Bo-NTD, BoNT-E, BoNT-F, and BoNT-G, one or more attenuated viral particles comprising one or more BoNT-A, BoNT-B, BoNT-$C_1$, BoNT-$C_2$, Bo-NTD, BoNT-E, BoNT-F, and BoNT-G, or one or more attenuated viral particles comprising one or more consensus BoNT-A, BoNT-B, BoNT-$C_1$, BoNT-$C_2$, Bo-NTD, BoNT-E, BoNT-F, and BoNT-G. The attenuated vaccine can be attenuated live vaccines, killed vaccines, and vaccines that use recombinant vectors to deliver foreign genes that encode one or more BoNT-A, BoNT-B, BoNT-$C_1$, BoNT-$C_2$, Bo-NTD, BoNT-E, BoNT-F, and BoNT-G protein, or one or more consensus BoNT-A, BoNT-B, BoNT-$C_1$, BoNT-$C_2$, Bo-NTD, BoNT-E, BoNT-F, and BoNT-G protein, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

a. Combination of BoNT-A, BoNT-B, BoNT-$C_1$, BoNT-$C_2$, BoNT-D, BoNT-E, BoNT-F, and/or BoNT-G, or Combinations Thereof The combinational vaccine can include one or more nucleic acids encoding BoNT-A, BoNT-B, BoNT-$C_1$, BoNT-$C_2$, BoNT-D, BoNT-E, BoNT-F, and/or BoNT-G. The one or more nucleic acids can be or include optimized nucleic acid sequences. The one or more nucleic acids can be or include heterologous nucleic acid sequences. The one or more nucleic acids can be a single expression vector or plasmid encoding BoNT-A, BoNT-B, BoNT-$C_1$, BoNT-$C_2$, BoNT-D, BoNT-E, BoNT-F, and/or BoNT-G. In other embodiments, the one or more nucleic acids can be eight expression vectors or plasmids, in which a first encodes BoNT-A, a second encodes BoNT-B, a third encodes BoNT-$C_1$, a fourth encodes BoNT-$C_2$, a fifth encodes BoNT-D, a sixth encodes BoNT-E, a seventh encodes BoNT-F, and an eighth encodes BoNT-G. In still other embodiments, the one or more nucleic acids can be one or more expression vectors or plasmids (e.g., 1, 2, 3, 4, or more), in which the one or more expression vectors or plasmids together encode BoNT-A, BoNT-B, BoNT-$C_1$, BoNT-$C_2$, BoNT-D, BoNT-E, BoNT-F, and/or BoNT-G.

The one or more nucleic acids can include nucleotide sequences encoding BoNT-A, BoNT-B, BoNT-$C_1$, BoNT-$C_2$, BoNT-D, BoNT-E, BoNT-F, and/or BoNT-G such that upon transcription and translation the BoNT-A, BoNT-B, BoNT-$C_1$, BoNT-$C_2$, BoNT-D, BoNT-E, BoNT-F, and/or BoNT-G are contained within a single polypeptide or protein. In other embodiments, the one or more nucleic acids can include nucleotide sequences encoding BoNT-A, BoNT-B, BoNT-$C_1$, BoNT-$C_2$, BoNT-D, BoNT-E, BoNT-F, and/or BoNT-G such that upon transcription and translation the BoNT-A, BoNT-B, BoNT-$C_1$, BoNT-$C_2$, BoNT-D, BoNT-E, BoNT-F, and/or BoNT-G are each contained within a separate polypeptide or protein. The one or more nucleic acids can include nucleotide sequences encoding BoNT-A, BoNT-B, BoNT-$C_1$, BoNT-$C_2$, BoNT-D, BoNT-E, BoNT-F, and/or BoNT-G such that upon transcription and translation BoNT-A, BoNT-B, BoNT-$C_1$, BoNT-$C_2$, BoNT-D, BoNT-E, BoNT- F, and/or BoNT-G are together contained (in any combination) within one or more separate polypeptides (e.g., 1, 2, 3, 4, or more).

The one or more nucleic acids can encode one or more IgE leader sequences such that an IgE leader sequence is linked to BoNT-A, BoNT-B, BoNT-C$_1$, BoNT-C$_2$, BoNT-D, BoNT-E, BoNT-F, and/or BoNT-G, or each of BoNT-A, BoNT-B, BoNT-C$_1$, BoNT-C$_2$, BoNT-D, BoNT-E, BoNT-F, and/or BoNT-G, or any combination thereof. In other embodiments, the one or more nucleic acids do not contain or are free of a nucleotide sequence encoding the IgE leader sequence.

In still other embodiments, the one or more nucleic acids can include a nucleotide sequence encoding a furin cleavage site such that the furin cleavage site is located or positioned between the respective nucleotide sequences encoding BoNT-A, BoNT-B, BoNT-C$_1$, BoNT-C$_2$, BoNT-D, BoNT-E, BoNT-F, and/or BoNT-G or any combination thereof. In other embodiments, the one or more nucleic acids do not contain or are free of the nucleotide sequence encoding the furin cleavage site.

In some embodiments, the one or more nucleic acids encoding BoNT-A, BoNT-B, BoNT-C$_1$, BoNT-C$_2$, BoNT-D, BoNT-E, BoNT-F, and/or BoNT-G can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the corresponding nucleic acid sequence encoding BoNT-A, BoNT-B, BoNT-C$_1$, BoNT-C$_2$, BoNT-D, BoNT-E, BoNT-F, and/or BoNT-G. In other embodiments, the one or more nucleic acids encoding BoNT-A, BoNT-B, BoNT-C$_1$, BoNT-C$_2$, BoNT-D, BoNT-E, BoNT-F, and/or BoNT-G can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in the corresponding amino acid sequence containing BoNT-A, BoNT-B, BoNT-C$_1$, BoNT-C$_2$, BoNT-D, BoNT-E, BoNT-F, and/or BoNT-G.

b. Combination of BoNT-A and BoNT-B

The combinational vaccine can include one or more nucleic acids encoding BoNT-A and BoNT-B. The one or more nucleic acids can be or include optimized nucleic acid sequences. The one or more nucleic acids can be or include heterologous nucleic acid sequences. The one or more nucleic acids can be a single expression vector or plasmid encoding BoNT-A and BoNT-B. In other embodiments, the one or more nucleic acids can be two expression vectors or plasmids, in which one encodes BoNT-A and the other encodes BoNT-B. The one or more nucleic acids can include nucleotide sequences encoding BoNT-A and BoNT-B such that upon transcription and translation the BoNT-A and BoNT-B are contained within a single polypeptide or protein. In other embodiments, the one or more nucleic acids can include nucleotides sequences encoding BoNT-A and BoNT-B such that upon transcription and translation the BoNT-A and BoNT-B are each contained within a separate polypeptide or protein.

The one or more nucleic acids can encode one or more IgE leader sequences such that an IgE leader sequence is linked to BoNT-A, BoNT-B, or both of BoNT-A and BoNT-B. In other embodiments, the one or more nucleic acids do not contain or are free of a nucleotide sequence encoding the IgE leader sequence. In still other embodiments, the one or more nucleic acids can include a nucleotide sequence encoding a furin cleavage site, such that the furin cleavage site is located or positioned between the respective nucleotide sequences encoding BoNT-A and BoNT-B. In other embodiments, the one or more nucleic acids do not contain or are free of the nucleotide sequence encoding the furin cleavage site.

The combination of BoNT-A and BoNT-B can be encoded by the optimized nucleic acid sequence encoding the amino acid sequence set forth in SEQ ID NO:9. The amino acid sequence set forth in SEQ ID NO:9 can include the amino acid sequence of BoNT-A linked to the amino acid sequence of BoNT-B, in which a furin cleavage site separates the respective amino acid sequences of BoNT-A and BoNT-B. Upon cleavage by furin, the amino acids sequences of BoNT-A and BoNT-B are contained within separate polypeptides or proteins.

In some embodiments, the nucleic acid encoding BoNT-A and BoNT-B can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence encoding the amino acid sequence set forth in SEQ ID NO:9. In other embodiments, the nucleic acid encoding the combination of BoNT-A and BoNT-B can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in the SEQ ID NO:9. In still other embodiments, the combination of the BoNT-A and BoNT-B antigens can be the amino acid sequence having at least about 805, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:9.

Some embodiments relate to fragments of the nucleic acid sequence encoding the amino acid sequence set forth in SEQ ID NO:9 that can be provided. Fragments can comprise at least 60%, at least 65%, at least 70%, at least 75%, at least 80%, at least 85%, at least 90%, at least 95%, at least 96%, at least 97%, at least 98%, or at least 99% of the nucleic acid sequence encoding the amino acid sequence set forth in SEQ ID NO:9. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of the nucleic acid sequence encoding the amino acid sequence set forth in SEQ ID NO:9 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to the nucleic acid sequence encoding the amino acid sequence set forth in SEQ ID NO:9. Some embodiments relate to fragments that have 96% or greater identity to the fragments of nucleic acid sequences encoding the combination of BoNT-A and BoNT-B herein. Some embodiments relate to fragments that have 97% or greater identity to the fragments of nucleic acid sequences encoding the combination of BoNT-A and BoNT-B herein. Some embodiments relate to fragments that have 98% or greater identity to the fragments of nucleic acid sequences encoding the combination of BoNT-A and BoNT-B herein. Some embodiments relate to fragments that have 99% or greater identity to the fragments of nucleic acid sequences encoding the combination of BoNT-A and BoNT-B herein. In some embodiments, fragments include sequences that encode a leader sequence, for example, an immunoglobulin leader sequence, such as the IgE leader sequence. In some embodiments, fragments are free of coding sequences that encode a leader sequence.

Fragments of SEQ ID NO:9 can be provided. Fragments can comprise at least 60%, at least 65%, at least 70%, at least 75%, at least 80%, at least 85%, at least 90%, at least 95%, at least 96%, at least 97%, at least 98%, or at least 90% of SEQ ID NO:9. In some embodiments, fragments include a leader sequence, for example, an immunoglobulin leader sequence, such as the IgE leader sequence. In some embodiments, fragments are free of a leader sequence.

Fragments of proteins with amino acid sequences having identity to fragments of SEQ ID NO:9 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:9. Some embodiments relate to fragments having 96% or greater identity to the fragments of protein sequences including the combination of BoNT-A and BoNT-B herein. Some embodiments relate to fragments having 97% or greater identity to the fragments of protein sequences including the combination of BoNT-A and BoNT-B herein. Some embodiments relate to fragments having 98% or greater identity to the fragments of protein sequences including the combination of BoNT-A and BoNT-B herein. Some embodiments relate to fragments having 99% or greater identity to the fragments of protein sequences including the combination of BoNT-A and BoNT-B herein. In some embodiments, fragments include a leader sequence, for example, an immunoglobulin leader sequence such as the IgE leader sequence. In some embodiments, the fragments are free of a leader sequence.

c. Combination of BoNT-E and BoNT-F

The combinational vaccine can include one or more nucleic acids encoding BoNT-E and BoNT-F. The one or more nucleic acids can be or include optimized nucleic acid sequences. The one or more nucleic acids can be or include heterologous nucleic acid sequences. The one or more nucleic acids can be a single expression vector or plasmid encoding BoNT-E and BoNT-F. In other embodiments, the one or more nucleic acids can be two expression vectors or plasmids, in which one encodes BoNT-E and the other encodes BoNT-F. The one or more nucleic acids can include nucleotide sequences encoding BoNT-E and BoNT-F such that upon transcription and translation the BoNT-E and BoNT-F are contained within a single polypeptide or protein. In other embodiments, the one or more nucleic acids can include nucleotides sequences encoding BoNT-E and BoNT-F such that upon transcription and translation the BoNT-E and BoNT-F are each contained within a separate polypeptide or protein.

The one or more nucleic acids can encode one or more IgE leader sequences such that an IgE leader sequence is linked to BoNT-E, BoNT-F, or both of BoNT-E and BoNT-F. In other embodiments, the one or more nucleic acids do not contain or are free of a nucleotide sequence encoding the IgE leader sequence. In still other embodiments, the one or more nucleic acids can include a nucleotide sequence encoding a furin cleavage site, such that the furin cleavage site is located or positioned between the respective nucleotide sequences encoding BoNT-E and BoNT-F. In other embodiments, the one or more nucleic acids do not contain or are free of the nucleotide sequence encoding the furin cleavage site.

The combination of BoNT-E and BoNT-F can be encoded by the optimized nucleic acid sequence encoding the amino acid sequence set forth in SEQ ID NO:10. The amino acid sequence set forth in SEQ ID NO:10 can include the amino acid sequence of BoNT-E linked to the amino acid sequence of BoNT-F, in which a furin cleavage site separates the respective amino acid sequences of BoNT-E and BoNT-F. Upon cleavage by furin, the amino acids sequences of BoNT-E and BoNT-F are contained within separate polypeptides or proteins.

In some embodiments, the nucleic acid encoding BoNT-E and BoNT-F can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence encoding the amino acid sequence set forth in SEQ ID NO:10. In other embodiments, the nucleic acid encoding the combination of BoNT-E and BoNT-F can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in the SEQ ID NO:10. In still other embodiments, the combination of the BoNT-E and BoNT-F antigens can be the amino acid sequence having at least about 805, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

Some embodiments relate to fragments of the nucleic acid sequence encoding the amino acid sequence set forth in SEQ ID NO:10 that can be provided. Fragments can comprise at least 60%, at least 65%, at least 70%, at least 75%, at least 80%, at least 85%, at least 90%, at least 95%, at least 96%, at least 97%, at least 98%, or at least 99% of the nucleic acid sequence encoding the amino acid sequence set forth in SEQ ID NO:10. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of the nucleic acid sequence encoding the amino acid sequence set forth in SEQ ID NO:10 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to the nucleic acid sequence encoding the amino acid sequence set forth in SEQ ID NO:10. Some embodiments relate to fragments that have 96% or greater identity to the fragments of nucleic acid sequences encoding the combination of BoNT-E and BoNT-F herein. Some embodiments relate to fragments that have 97% or greater identity to the fragments of nucleic acid sequences encoding the combination of BoNT-E and BoNT-F herein. Some embodiments relate to fragments that have 98% or greater identity to the fragments of nucleic acid sequences encoding the combination of BoNT-E and BoNT-F herein. Some embodiments relate to fragments that have 99% or greater identity to the fragments of nucleic acid sequences encoding the combination of BoNT-E and BoNT-F herein. In some embodiments, fragments include sequences that encode a leader sequence, for example, an immunoglobulin leader sequence, such as the IgE leader sequence. In some embodiments, fragments are free of coding sequences that encode a leader sequence.

Fragments of SEQ ID NO:10 can be provided. Fragments can comprise at least 60%, at least 65%, at least 70%, at least 75%, at least 80%, at least 85%, at least 90%, at least 95%, at least 96%, at least 97%, at least 98%, or at least 90% of SEQ ID NO:10. In some embodiments, fragments include a leader sequence, for example, an immunoglobulin leader sequence, such as the IgE leader sequence. In some embodiments, fragments are free of a leader sequence.

Fragments of proteins with amino acid sequences having identity to fragments of SEQ ID NO:10 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:10. Some embodiments relate to fragments having 96% or greater identity to the fragments of protein sequences including the combination of BoNT-E and BoNT-F herein. Some embodiments relate to fragments having 97% or greater identity to the fragments of protein sequences including the combination of BoNT-E and BoNT-F herein. Some embodiments relate to fragments having 98% or greater identity to the fragments of protein sequences including the combination of BoNT-E and BoNT-F herein. Some embodiments relate to fragments having 99% or greater identity to the fragments of protein sequences including the combination of BoNT-E and BoNT-F herein. In some embodiments, fragments include a leader sequence, for example, an immunoglobulin leader sequence such as the IgE leader sequence. In some embodiments, the fragments are free of a leader sequence.

d. Combination of BoNT-A, BoNT-B, and BoNT-E

The combinational vaccine can include one or more nucleic acids encoding BoNT-A, BoNT-B, and BoNT-E. The one or more nucleic acids can be or include optimized nucleic acid sequences. The one or more nucleic acids can be or include heterologous nucleic acid sequences. The one or more nucleic acids can be a single expression vector or plasmid encoding BoNT-A, BoNT-B, and BoNT-E. In other embodiments, the one or more nucleic acids can be three expression vectors or plasmids, in which one encodes BoNT-A, a second encodes BoNT-B, and a third encodes BoNT-E. In other embodiments, the one or more nucleic acids can be two expression vectors or plasmids, in which one encodes two of BoNT-A, BoNT-B, and BoNT-E and the other encodes the remaining BoNT (e.g., BoNT-A and BoNT-B encoded by one vector or plasmid and BoNT-E encoded by the second vector or plasmid, and so forth).

The one or more nucleic acids can include nucleotide sequences encoding BoNT-A, BoNT-B, and BoNT-E such that upon transcription and translation the BoNT-A, BoNT-B, and BoNT-E are contained within a single polypeptide or protein. In other embodiments, the one or more nucleic acids can include nucleotides sequences encoding BoNT-A, BoNT-B, and BoNT-E such that upon transcription and translation the BoNT-A, BoNT-B, and BoNT-E are each contained within a separate polypeptide or protein. The one or more nucleic acids can include nucleotide sequences encoding BoNT-A, BoNT-B, and BoNT-E such that upon transcription and translation, BoNT-A and BoNT-B are contained within a first polypeptide or protein and BoNT-E is contained within a second polypeptide or protein. The one or more nucleic acids can include nucleotide sequences encoding BoNT-A, BoNT-B, and BoNT-E such that upon transcription and translation, BoNT-A and BoNT-E are contained within a first polypeptide or protein and BoNT-B is contained within a second polypeptide or protein. The one or more nucleic acids can include nucleotide sequences encoding BoNT-A, BoNT-B, and BoNT-E such that upon transcription and translation, BoNT-E and BoNT-B are contained within a first polypeptide or protein and BoNT-A is contained within a second polypeptide or protein.

The one or more nucleic acids can encode one or more IgE leader sequences such that an IgE leader sequence is linked to BoNT-A, BoNT-B, BoNT-E, or each of BoNT-A, BoNT-B, and BoNT-E. In other embodiments, the one or more nucleic acids do not contain or are free of a nucleotide sequence encoding the IgE leader sequence. In still other embodiments, the one or more nucleic acids can include a nucleotide sequence encoding a furin cleavage site, such that the furin cleavage site is located or positioned between the respective nucleotide sequences encoding BoNT-A and BoNT-B, the respective nucleotide sequences encoding BoNT-A and BoNT-E, the respective nucleotide sequences encoding BoNT-B and BoNT-E, or combinations thereof. In other embodiments, the one or more nucleic acids do not contain or are free of the nucleotide sequence encoding the furin cleavage site.

e. Combination of BoNT-A, BoNT-B, BoNT-E, and BoNT-F

The combinational vaccine can include one or more nucleic acids encoding BoNT-A, BoNT-B, BoNT-E, and BoNT-F. The one or more nucleic acids can be or include optimized nucleic acid sequences. The one or more nucleic acids can be or include heterologous nucleic acid sequences. The one or more nucleic acids can be a single expression vector or plasmid encoding BoNT-A, BoNT-B, BoNT-E, and BoNT-F. In other embodiments, the one or more nucleic acids can be encoded by four expression vectors or plasmids, in which one encodes BoNT-A, a second encodes BoNT-B, a third encodes BoNT-E, and a fourth encodes BoNT-F. In other embodiments, the one or more nucleic acids can be two or three expression vectors or plasmids, in which the two or three expression vectors or plasmids together encode BoNT-A, BoNT-B, BoNT-E, and BoNT-F.

The one or more nucleic acids can include nucleotide sequences encoding BoNT-A, BoNT-B, BoNT-E, and BoNT-F such that upon transcription and translation the BoNT-A, BoNT-B, BoNT-E, and BoNT-F are contained within a single polypeptide or protein. In other embodiments, the one or more nucleic acids can include nucleotides sequences encoding BoNT-A, BoNT-B, BoNT-E, and BoNT-F such that upon transcription and translation the BoNT-A, BoNT-B, BoNT-E, and BoNT-F are each contained within a separate polypeptide or protein. The one or more nucleic acids can include nucleotide sequences encoding BoNT-A, BoNT-B, BoNT-E, and BoNT-F such that upon transcription and translation, BoNT-A, BoNT-B, BoNT-E, and BoNT-F are together contained (in any combination) within three separate polypeptides. The one or more nucleic acids can include nucleotide sequences encoding BoNT-A, BoNT-B, BoNT-E, and BoNT-F such that upon transcription and translation, BoNT-A, BoNT-B, BoNT-E, and BoNT-F are together contained (in any combination) within two separate polypeptides.

The one or more nucleic acids can encode one or more IgE leader sequences such that an IgE leader sequence is linked to BoNT-A, BoNT-B, BoNT-E, BoNT-F, or each of BoNT-A, BoNT-B, BoNT-E, and BoNT-F, or any combinations thereof. In other embodiments, the one or more nucleic acids do not contain or are free of a nucleotide sequence encoding the IgE leader sequence. In still other embodiments, the one or more nucleic acids can include a nucleotide sequence encoding a furin cleavage site, such that the furin cleavage site is located or positioned between the respective nucleotide sequences encoding BoNT-A and BoNT-B, the respective nucleotide sequences encoding BoNT-A and BoNT-E, the respective nucleotide sequences encoding BoNT-A and BoNT-F, the respective nucleotide sequences encoding BoNT-B and BoNT-E, the respective nucleotide sequences encoding BoNT-B and BoNT-F, the respective nucleotide sequences encoding BoNT-E and BoNT-F, or combinations thereof. In other embodiments, the one or more nucleic acids do not contain or are free of the nucleotide sequence encoding the furin cleavage site.

The combination of BoNT-A, BoNT-B, BoNT-E, and BoNT-F can be encoded by the optimized nucleic acid sequence encoding the amino acid sequence set forth in SEQ ID NO:11. The amino acid sequence set forth in SEQ ID NO:11 can include the respective amino acid sequences of BoNT-A, BoNT-B, BoNT-E, and BoNT-F linked to one another, in which a furin cleavage site separates each of the respective amino acid sequences. Upon cleavage by furin, the amino acid sequences of BoNT-A, BoNT-B, BoNT-E, and BoNT-F are contained within separate polypeptides or proteins.

In some embodiments, the nucleic acid encoding BoNT-A, BoNT-B, BoNT-E, and BoNT-F can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence encoding the amino acid sequence set forth in SEQ ID NO:11. In other embodiments, the nucleic acid encoding the combination of BoNT-A, BoNT-B, BoNT-E, and BoNT-F can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in the SEQ ID NO:11. In still other embodiments, the combination of the BoNT-A, BoNT-B, BoNT-E, and BoNT-F antigens can be the amino acid sequence having at least about 805, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:11.

Some embodiments relate to fragments of the nucleic acid sequence encoding the amino acid sequence set forth in SEQ ID NO:11 that can be provided. Fragments can comprise at least 60%, at least 65%, at least 70%, at least 75%, at least 80%, at least 85%, at least 90%, at least 95%, at least 96%, at least 97%, at least 98%, or at least 99% of the nucleic acid sequence encoding the amino acid sequence set forth in SEQ ID NO:11. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of the nucleic acid sequence encoding the amino acid sequence set forth in SEQ ID NO:11 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to the nucleic acid sequence encoding the amino acid sequence set forth in SEQ ID NO:11. Some embodiments relate to fragments that have 96% or greater identity to the fragments of nucleic acid sequences encoding the combination of BoNT-A, BoNT-B, BoNT-E, and BoNT-F herein. Some embodiments relate to fragments that have 97% or greater identity to the fragments of nucleic acid sequences encoding the combination of BoNT-A, BoNT-B, BoNT-E, and BoNT-F herein. Some embodiments relate to fragments that have 98% or greater identity to the fragments of nucleic acid sequences encoding the combination of BoNT-A, BoNT-B, BoNT-E, and BoNT-F herein. Some embodiments relate to fragments that have 99% or greater identity to the fragments of nucleic acid sequences encoding the combination of BoNT-A, BoNT-B, BoNT-E, and BoNT-F herein. In some embodiments, fragments include sequences that encode a leader sequence, for example, an immunoglobulin leader sequence, such as the IgE leader sequence. In some embodiments, fragments are free of coding sequences that encode a leader sequence.

Fragments of SEQ ID NO:11 can be provided. Fragments can comprise at least 60%, at least 65%, at least 70%, at least 75%, at least 80%, at least 85%, at least 90%, at least 95%, at least 96%, at least 97%, at least 98%, or at least 90% of SEQ ID NO:11. In some embodiments, fragments include a leader sequence, for example, an immunoglobulin leader sequence, such as the IgE leader sequence. In some embodiments, fragments are free of a leader sequence.

Fragments of proteins with amino acid sequences having identity to fragments of SEQ ID NO:11 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:11. Some embodiments relate to fragments having 96% or greater identity to the fragments of protein sequences including the combination of BoNT-A, BoNT-B, BoNT-E, and BoNT-F herein. Some embodiments relate to fragments having 97% or greater identity to the fragments of protein sequences including the combination of BoNT-A, BoNT-B, BoNT-E, and BoNT-F herein. Some embodiments relate to fragments having 98% or greater identity to the fragments of protein sequences including the combination of BoNT-A, BoNT-B, BoNT-E, and BoNT-F herein. Some embodiments relate to fragments having 99% or greater identity to the fragments of protein sequences including the combination of BoNT-A, BoNT-B, BoNT-E, and BoNT-F herein. In some embodiments, fragments include a leader sequence, for example, an immunoglobulin leader sequence such as the IgE leader sequence. In some embodiments, the fragments are free of a leader sequence.

4. Vaccine Constructs and Plasmids

The vaccine can comprise nucleic acid constructs or plasmids that encode the BoNT antigens described above. Provided herein are genetic constructs that can comprise a nucleic acid sequence that encodes the BoNT antigens disclosed herein including protein sequences, consensus protein sequences, sequences homologous to protein or consensus protein sequences, fragments of protein or consensus protein sequences, and sequences homologous to fragments of protein or consensus protein sequences. The genetic construct can be present in the cell as a functioning extrachromosomal molecule. The genetic construct can be a linear minichromosome including centromere, telomeres or plasmids or cosmids. The genetic construct can include one or more heterologous nucleotide sequences.

In some embodiments, the genetic constructs can be in the form of monovalent plasmids expressing the BoNT antigens. In other embodiments, the genetic constructs can be in the form of multivalent plasmids expressing multiple BoNT antigens, for example, but not limited, bivalent plasmids, trivalent plasmids, quadravalent or tetravalent plasmids, and pentavalent plasmids. In still other embodiments, the genetics constructs can be in the form of a combination of monovalent plasmids and/or multivalent plasmids, and thus, the genetic constructs can be a single plasmid or multiple plasmids that encode for 1, 2, 3, 4, or more of the BoNT antigens described herein.

In some embodiments, the genetic constructs can be in the form of monovalent plasmids expressing BoNT-A, BoNT-B, BoNT-$C_1$, BoNT-$C_2$, BoNT-D, BoNT-E, BoNT-F, or BoNT-G antigens. The genetic constructs can be in the form of a bivalent plasmid expressing any two BoNT antigens combinations of BoNT-A, BoNT-B, BoNT-$C_1$, BoNT-$C_2$, BoNT-D, BoNT-E, BoNT-F, and BoNT-G. One embodiment may include (1) BoNT-A and BoNT-B, (2) BoNT-A and BoNT-E, (3) BoNT-A and BoNT-F, (4) BoNT-B and BoNT-E, (5) BoNT-B and BoNT-F, and (6) BoNT-E and BoNT-F in any order.

The genetic construct can be in the form of a trivalent plasmid expressing any three BoNT antigen combinations of BoNT-A, BoNT-B, BoNT-$C_1$, BoNT-$C_2$, BoNT-D, BoNT-E, BoNT-F, and BoNT-G. One embodiment may include (1) BoNT-A, BoNT-B and BoNT-E, (2) BoNT-A, BoNT-B, and BoNT-F, (3) BoNT-B, BoNT-E, and BoNT-F, and (4) BoNT-A, BoNT-E, and BoNT-F in any order.

The genetic construct can be in the form of a quadravalent plasmid expressing any four BoNT antigen combinations of BoNT-A, BoNT-B, BoNT-$C_1$, BoNT-$C_2$, BoNT-D, BoNT-E, BoNT-F, and/or BoNT-G. One embodiment may include encoding BoNT-A, BoNT-B, BoNT-E, and BoNT-F in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer, an initiation codon, a stop codon, or a polyadenylation signal.

The nucleic acid sequences can make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding the BoNT antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the BoNT antigen and can further comprise an initiation codon, which can be upstream of the antigen coding sequence, and a stop codon, which can be downstream of the antigen coding sequence. The initiation and termination codon can be in frame with the BoNT antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the antigen coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the BoNT antigen sequences. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>-2876 backbone, downstream of the Kanamycin gene

C>T 3277 in pUC origin of replication (Ori) high copy number mutation (see Nucleic Acid Research 1985)

G>C 3753 in very end of pUC On upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be psE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

Figure 1:
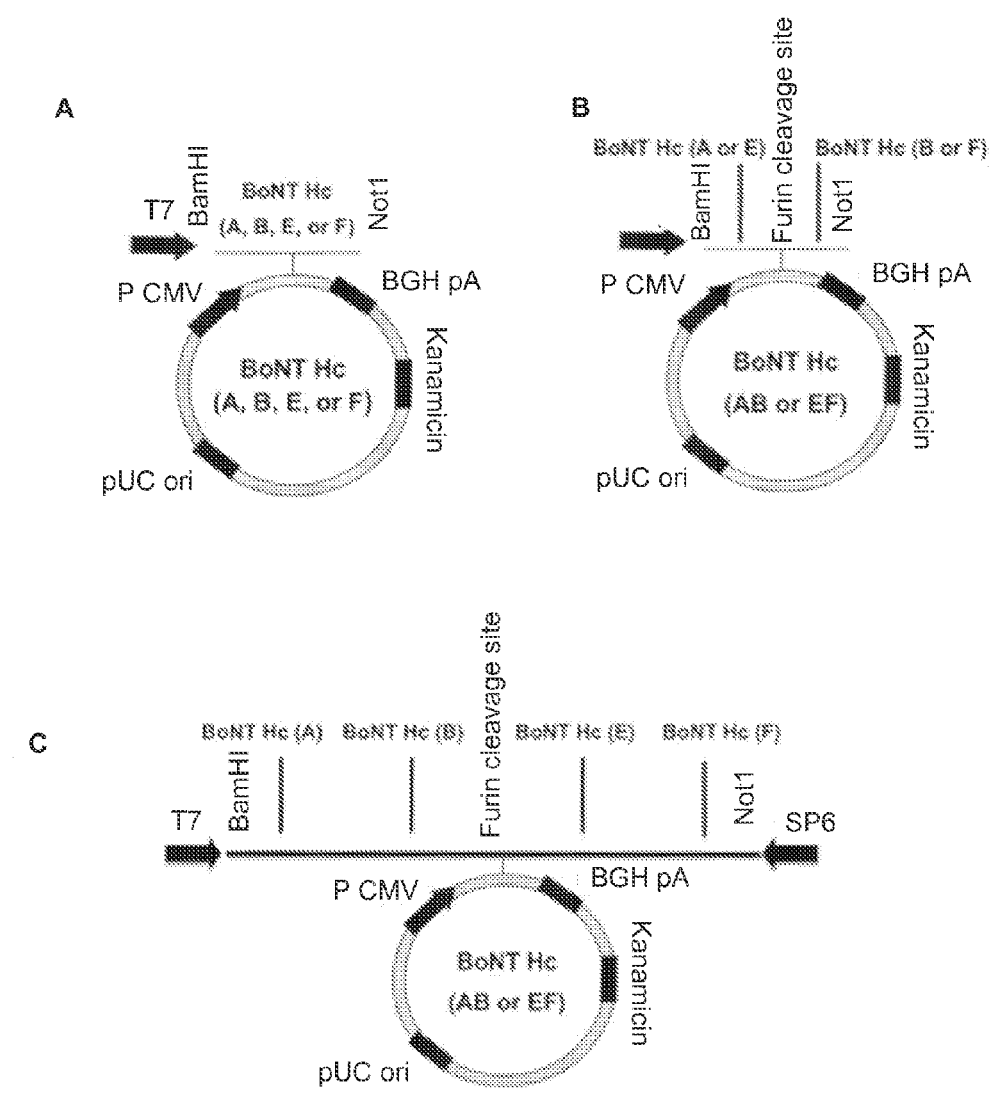

In some embodiments the vector can comprise one or more of the nucleic acid sequence of SEQ ID NO:1, SEQ ID NO:3, SEQ ID NO:5, SEQ ID NO:7, the nucleic acid encoding the amino acid sequence set forth in SEQ ID NO:9, the nucleic acid encoding the amino acid sequence set forth in SEQ ID NO:10, and/or the nucleic acid encoding the amino acid sequence set forth in SEQ ID NO:11. Exemplary vectors are shown in FIG. 1.

5. Pharmaceutical Compositions of the Vaccine

The vaccine can be in the form of a pharmaceutical composition. The pharmaceutical composition can comprise the vaccine.

The pharmaceutical compositions can comprise about 5 nanograms to about 10 mg of the DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vaso-constriction agent is added to the formulation.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80,CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof 6. Methods of Vaccine Administration Provided herein is a method for administering the pharmaceutical formulations for providing genetic constructs and proteins of the BoNT including the BoNT antigens BoNT-A, BoNT-B, BoNT-$C_1$, BoNT-$C_2$, BoNT-D, BoNT-E, BoNT-F and/or BoNT-G or any combination thereof, which comprise epitopes that make them particularly effective immunogens against which an immune response to neurotoxin from *Clostridium botulinum* serotypes BoNT-A, BoNT-B, BoNT-$C_1$, BoNT-$C_2$, BoNT-D, BoNT-E, BoNT-F and/or BoNT-G or any combination thereof can be induced. In some embodiments, the method of administering can include providing genetic constructs and proteins of the BoNT including the BoNT antigens BoNT-A, BoNT-B, BoNT-E, and/or BoNT-F, which comprise epitopes that make them particularly effective immunogens against which an immune response to neurotoxin from *Clostridium botulinum* serotypes A, B, E, and F can be induced.

The method of administering the vaccine, or vaccination, can be provided to induce a therapeutic and/or prophylactic immune response. The vaccination process can generate in the mammal an immune response against a plurality of *Clostridium botulinum* serotypes, including serotypes A, B, $C_1$, $C_2$, D, E, F, and/or G or any combination thereof, and in some embodiments, an immune response against serotypes A, B, E, and/or F.

The vaccine can be administered to an individual to modulate the activity of the mammal's immune system and enhance the immune response. The administeration of the vaccine can be the transfection of the BoNT as a nucleic acid molecule that is expressed in the cell and administered to the surface of the cell upon which the immune system recognizes and induces a cellular, humoral, or cellular and humoral response. The administration of the vaccine can be used to induce or elicit an immune response in mammals against a plurality of BoNT, including BoNT-A, BoNT-B, BoNT-C1, BoNT-C2, BoNT-D, BoNT-E, BoNT-F and/or BoNT-G or any combination thereof, and in some embodiments, against BoNT-A, BoNT-B, BoNT-E, and/or BoNT-F, by administering to the mammals the vaccine as discussed herein. The administration of the vaccine can be used to induce or elicit neutralizing antibodies against a plurality of BoNT, including BoNT-A, BoNT-B, BoNT-C1, BoNT-C2, BoNT-D, BoNT-E, BoNT-F and/or BoNT-G or any combination thereof, and in some embodiments, against BoNT-A, BoNT-B, BoNT-E, and/or BoNT-F, by administering to the mammals the vaccine as discussed herein.

Upon administration of the vaccine to the mammal, and thereupon the vector into the cells of the mammal, the transfected cells will express and secrete BoNT antigen(s), including BoNT-A, BoNT-B, BoNT-C1, BoNT-C2, BoNT-D, BoNT-E, BoNT-F and/or BoNT-G or any combination thereof, and in some embodiments, BoNT-A, BoNT-B, BoNT-E, and/or BoNT-F. In other embodiments, upon administration of the vaccine to the mammal, and thereupon the vector into the cells of the mammal, the transfected cells will express and secrete consensus BoNT antigen(s), including BoNT-A, BoNT-B, BoNT-C1, BoNT-C2, BoNT-D, BoNT-E, BoNT-F and/or BoNT-G or any combination thereof, and in some embodiments, BoNT-A, BoNT-B, BoNT-E, and/or BoNT-F. These secreted proteins, or synthetic antigens, will be recognized as foreign by the immune system, which will mount an immune response that can include: antibodies made against the antigens, and T-cell response specifically against the antigen.

In some examples, a mammal vaccinated with the vaccines discussed herein will have a primed immune system and when challenged with BoNT antigen(s), including BoNT-A, BoNT-B, BoNT-C1, BoNT-C2, BoNT-D, BoNT-E, BoNT-F and/or BoNT-G or any combination thereof, the primed immune system will allow for rapid clearing of subsequent BoNT, including BoNT-A, BoNT-B, BoNT-C1, BoNT-C2, BoNT-D, BoNT-E, BoNT-F and/or BoNT-G or any combination thereof, whether through the humoral (e.g., neutralizing antibodies), cellular, or both. In some embodiments, a mammal vaccinated with the vaccines discussed herein will have a primed immune system and when challenged with BoNT antigen(s), including BoNT-A, BoNT-B, BoNT-E, and/or BoNT-F, the primed immune system will allow for rapid clearing of subsequent BoNT, including BoNT-A, BoNT-B, BoNT-E, and/or BoNT-F, whether through the humoral (e.g., neutralizing antibodies), cellular, or both. The vaccine can be administered to an individual to modulate the activity of the individual's immune system thereby enhancing the immune response.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The vaccine dose can be between 1 µg to 10 mg component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

a. Method of Generating an Immune Response with the Vaccine

The vaccine can be used to generate an immune response in a mammal, including therapeutic or prophylactic immune response. The immune response can generate antibodies (e.g., neutralizing antibodies) and/or killer T cells, which are directed to the BoNT antigen BoNT-A, BoNT-B, BoNT-C1, BoNT-C2, BoNT-D, BoNT-E, BoNT-F and/or BoNT-G or any combination thereof. Such antibodies and T cells can be isolated. The immune response can generate neutralizing antibodies that are reactive to BoNT-A, BoNT-B, BoNT-C1, BoNT-C2, BoNT-D, BoNT-E, BoNT-F and/or BoNT-G or any combination thereof Some embodiments provide methods of generating immune responses against the BoNT antigen BoNT-A, BoNT-B, BoNT-C1, BoNT-C2, BoNT-D, BoNT-E, BoNT-F and/or BoNT-G or any combination thereof, which comprise administering to an individual the vaccine. Some embodiments provide methods of prophylactically vaccinating an individual against infection with *Clostridium botulinum* serotypes A, B, $C_1$, $C_2$, D, E, F, and/or G, or a combination thereof, which comprise administering the vaccine. Some embodiments provide methods of prophylactically vaccinating an individual against neurotoxin from one or more neurotoxins from serotypes A, B, $C_1$, $C_2$, D, E, F, and/or G, or a combination thereof of *Clostridium botulinum*, which comprise administering the vaccine. Some embodiments provide methods of therapeutically vaccinating an individual that has been infected with serotypes A, B, $C_1$, $C_2$, D, E, F, and/or G, or a combination thereof of *Clostridium botulinum*, which comprise administering the vaccine. Some embodiments provide methods of therapeutically vaccinating an individual that has been exposed to neurotoxin from serotypes A, B, $C_1$, $C_2$, D, E, F, and/or G, or a combination thereof of *Clostridium botulinum*, which comprise administering the vaccine. Diagnosis of infection with *Clostridium botulinum* serotypes A, B, $C_1$, $C_2$, D, E, F, and/or G, or a combination thereof or exposure to neurotoxin from serotypes A, B, $C_1$, $C_2$, D, E, F, and/or G, or a combination thereof, prior to administration of the vaccine can be done routinely.

The vaccine induces humoral immunogenicity and provides protection against lethal challenge with *Clostridium botulinum* neurotoxin providing 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% protection against lethal challenge after vaccination with monovalent, bivalent, trivalent, or tetravalent BoNT vaccine constructs as described above. The induced humoral immunogenicity can include neutralizing antibodies that facilitate protection against lethal challenge with *Clostridium botulinum* neurotoxin.

b. Method of Treatment with the Vaccine

The vaccine can be used to generate an immune response in a mammal that is protective against neurotoxicity and flaccid paralysis. The vaccine can also be used to generate an immune response in a mammal that is protective against disease (i.e., intoxication), including the symptoms of respiratory distress, flaccid paralysis, respiratory failure, and impaired motor function. The immune response can generate an antigen-specific CTL response that does not cause damage to or inflammation of brain or neurological system. In some embodiments, the vaccine can be delivered to the periphery to establish an antigen-specific immune response targeting the neurological system to clear or eliminate *Clostridim botulinum* serotypes A, B, $C_1$, $C_2$, D, E, F, and/or G, or a combination thereof without damaging or causing neurotoxicity and flaccid paralysis or other symptoms of intoxication. In other embodiments, the vaccine can be delivered to the periphery to establish neutralizing antibodies that are reactive to the neurotoxin from serotypes of *Clostridium botulinum* A, B, $C_1$, $C_2$, D, E, F, and/or G, or a combination thereof without damaging or causing neurotoxicity and flaccid paralysis or other symptoms of intoxication.

In some embodiments, treatment can include delivery of a vaccine comprising an BoNT-A, BoNT-B, BoNT-$C_1$, BoNT-$C_2$, BoNT-E, BoNT-F, and/or BoNT-G antigen or a combination thereof to the periphery to establish an antigen-specific immune response targeting the neurological system to clear or eliminate *Clostridim botulinum* serotype A, B, $C_1$, $C_2$, D, E, F, and/or G, or a combination thereof without damaging or causing neurotoxicity and flaccid paralysis. In some embodiments, treatment can include delivery of a vaccine comprising an BoNT-A, BoNT-B, BoNT-$C_1$, BoNT-$C_2$, BoNT-E, BoNT-F, and/or BoNT-G antigen or a combination thereof to the periphery to establish an antigen-specific immune response targeting the neurological system to clear or eliminate neurotoxin from *Clostridim botulinum* serotype A, B, $C_1$, $C_2$, D, E, F, and/or G, or a combination thereof without damaging or causing neurotoxicity and flaccid paralysis. In other embodiments, treatment can include delivery of a vaccine comprising BoNT-A, BoNT-B, BoNT-$C_1$, BoNT-$C_2$, BoNT-E, BoNT-F, and/or BoNT-G antigen or a combination thereof to the periphery to establish neutralizing antibodies that are reactive to the neurotoxin from *Clostridium botulinum* serotypes A, B, $C_1$, $C_2$, D, E, F, and/or G, or a combination thereof without damaging or causing neurotoxicity and flaccid paralysis or other symptoms of intoxication.

In other embodiments, treatment can include delivery of a vaccine comprising an BoNT-A, BoNT-B, BoNT-$C_1$, BoNT-$C_2$, BoNT-E, BoNT-F, and/or BoNT-G consensus antigen or a combination thereof to the periphery to establish an antigen-specific immune response targeting the neurological system to clear or eliminate *Clostridim botulinum* serotype A, B, $C_1$, $C_2$, D, E, F, and/or G, or a combination thereof without damaging or causing neurotoxicity and flaccid paralysis. In other embodiments, treatment can include delivery of a vaccine comprising an BoNT-A, BoNT-B, BoNT-$C_1$, BoNT-$C_2$, BoNT-E, BoNT-F, and/or BoNT-G consensus antigen or a combination thereof to the periphery to establish an antigen-specific immune response targeting the neurological system to clear or eliminate neurotoxin from *Clostridim botulinum* serotype A, B, $C_1$, $C_2$, D, E, F, and/or G, or a combination thereof without damaging or causing neurotoxicity and flaccid paralysis. In other embodiments, treatment can include delivery of a vaccine comprising an BoNT-A, BoNT-B, BoNT-$C_1$, BoNT-$C_2$, BoNT-E, BoNT-F, and/or BoNT-G consensus antigen or a combination thereof to the periphery to establish neutralizing antibodies that are reactive to the neurotoxin from *Clostridium botulinum* serotypes A, B, $C_1$, $C_2$, D, E, F, and/or G, or a combination thereof without damaging or causing neurotoxicity and flaccid paralysis or other symptoms of intoxication.

7. Routes of Administration

The vaccine or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The antigen can be delivered via DNA injection and along with in vivo electroporation.

a. Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

8. Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

9. Examples

The foregoing may be better understood by reference to the following examples, which are intended for illustrative purposes and are not intended to limit the scope of the invention.

Example 1

Expression Vectors

A, B, E, and F are botulinum neurotoxins (BoNTs) from four respective serotypes of *Clostridium botulinum*. The nucleic acid sequences encoding the non-toxic heavy chains (Hc) of each of neurotoxins A, B, E, and F were codon and RNA optimized, and synthesized to also encode for an IgE leader sequence, which increases secretion of the BoNT heavy chain.

SEQ ID NO:1 corresponds to the optimized nucleic acid sequence encoding the non-toxic heavy chain of neurotoxin A and the IgE leader sequence. SEQ ID NO:3 corresponds to the optimized nucleic acid sequence encoding the non-toxic heavy chain of neurotoxin B and the IgE leader sequence. SEQ ID NO:5 corresponds to the optimized nucleic acid sequence encoding the non-toxic heavy chain of neurotoxin E and the IgE leader sequence. SEQ ID NO:7 corresponds to the optimized nucleic acid sequence encoding the non-toxic heavy chain of neurotoxin F and the IgE leader sequence.

The optimized nucleic acid sequences were inserted into a pUC57 vector, thereby adding a poly A tail to end translation. The inserts were then cloned or moved into the pVax1 expression vector between the BamHI and Not1 sites (FIG. 1A). The CMV promoter, BGH poly A signal, kanamycin resistance gene, and pUC origin of the pVax1 expression vector are also shown in FIG. 1. The resulting vectors are monovalent expression vectors, namely driving expression of one of the following proteins: (1) heavy chain of neurotoxin A with the IgE leader sequence (SEQ ID NO:2); (2) heavy chain of neurotoxin B with the IgE leader sequence (SEQ ID NO:4); (3) heavy chain of neurotoxin E with the IgE leader sequence (SEQ ID NO:6); or (4) heavy chain of neurotoxin F with the IgE leader sequence (SEQ ID NO:8).

Additionally, bivalent expression vectors were generated in which optimized nucleic acid sequences encoding two of BoNT heavy chains A, B, E, or F (e.g., SEQ ID NOS:1, 3, 5, and 7) were inserted into the pVax1 expression vector between the BamHI and Not1 sites (FIG. 1B). The two BoNT heavy chains were separated by a furin cleavage site to allow for the secretion of each individual BoNT heavy chain.

Figure 13:
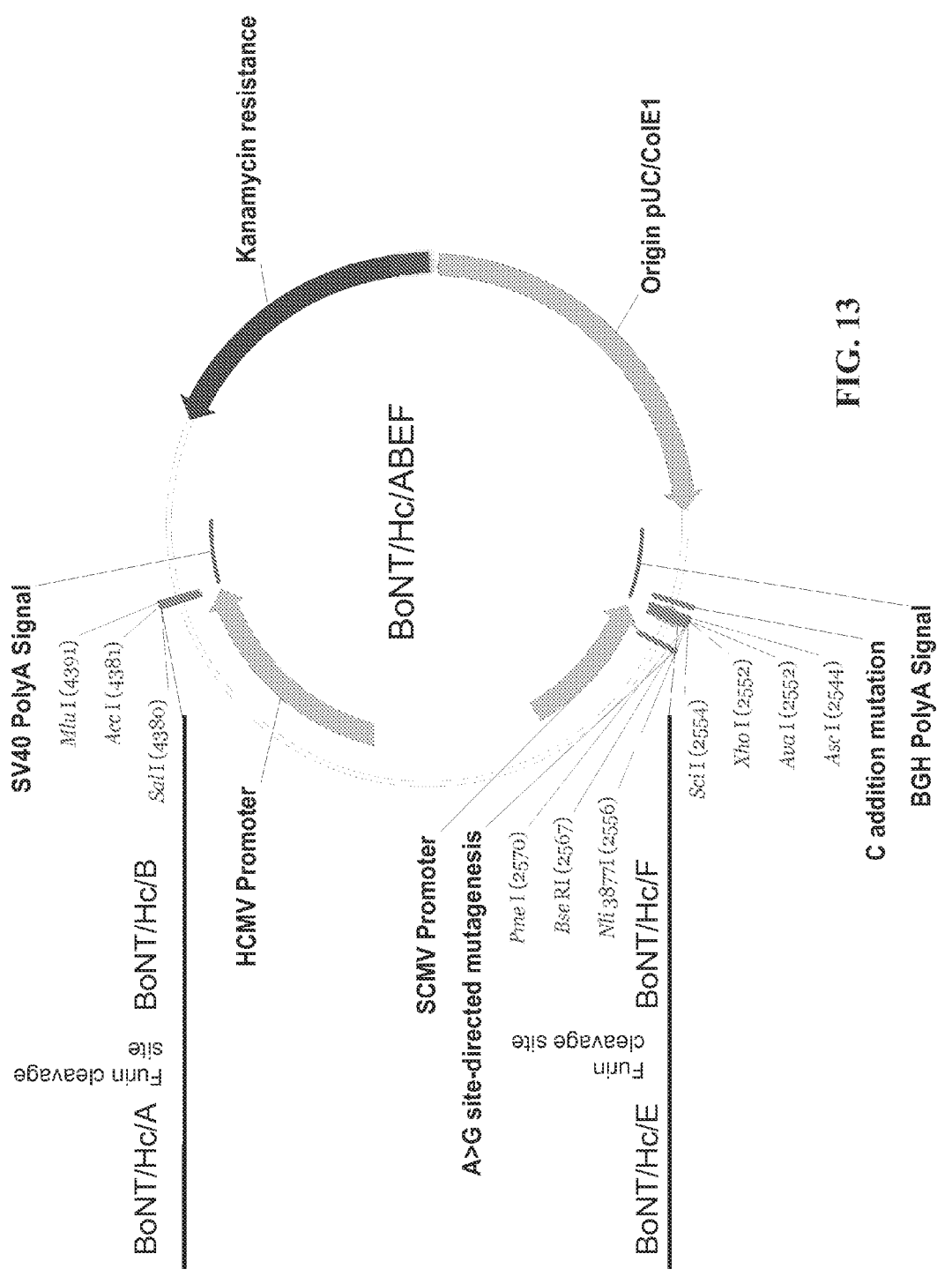

A quadravalent expression vector was generated by placing optimized nucleic acid sequences encoding the heavy chains of neurotoxins A, B, E, and F (e.g., SEQ ID NOS:1, 3, 5, and 7) between the BamHI and Not1 sites of the pVax1 expression vector as shown in FIG. 1C. The quadravalent expression vector had dual promoters for driving expression of the four heavy chains. The quadravalent expression vector was also constructed as shown in FIG. 13.

Example 2

In Vitro Expression from MonoValent Expression Vectors

Figure 2:
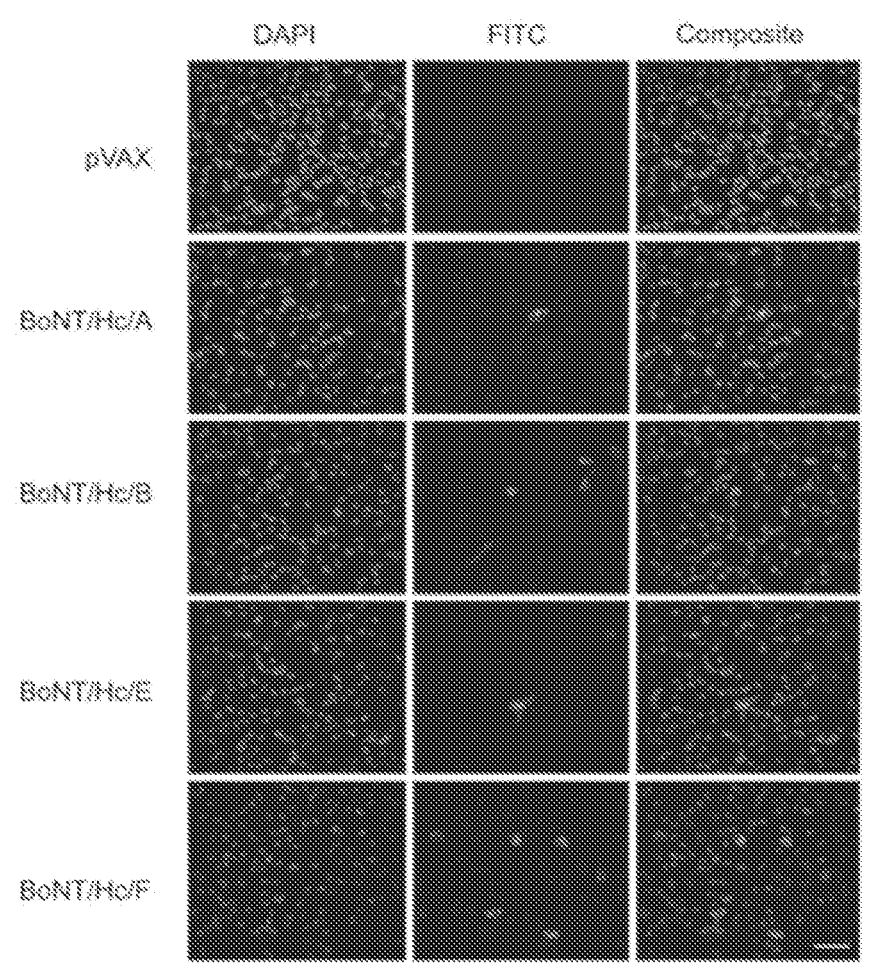

Expression of the heavy chains of neurotoxins A, B, E, and F was confirmed by transfecting human rhabdomyosarcoma (RD) cells with the monovalent BoNT/Hc constructs described above in Example 1 and shown in FIG. 1A. Each monovalent BoNT/Hc construct also included a hemagglutinin (HA) sequence linked to the respective heavy chain thereby allowing for detection of the heavy chains. Immunofloresence analysis of the transfected cells is in shown in FIG. 2 and confirmed in vitro expression of the heavy chains of neurotoxins A, B, E, and F. The bar in FIG. 2 equals 160 µm. Specifically, DAPI was used to stain nuclei and FITC staining was used to detect the respective heavy chain. The composite panel showed an overlay of the respective DAPI and FITC stainings.

Example 3

Humoral Immune Response to BoNT Hc Vaccines

The constructs described above in Example 1 and illustrated in FIG. 1 were analyzed to evaluate whether such constructs would be effective vaccines. Specifically, the humoral immune response was examined in Balb/c mice by immunizing Balb/c mice with either a monovalent BoNT/Hc construct (i.e., vaccine), or a bivalent BoNT/Hc vaccine.

Three groups of Balb/c mice were immunized as detailed below. The magnitude of the humoral response induced by the BoNT/Hc vaccines was detected using an enzyme linked immunosorbent assay (ELISA). The ELISA detected antibodies specific to the respective BoNT heavy chains.

Figure 3:
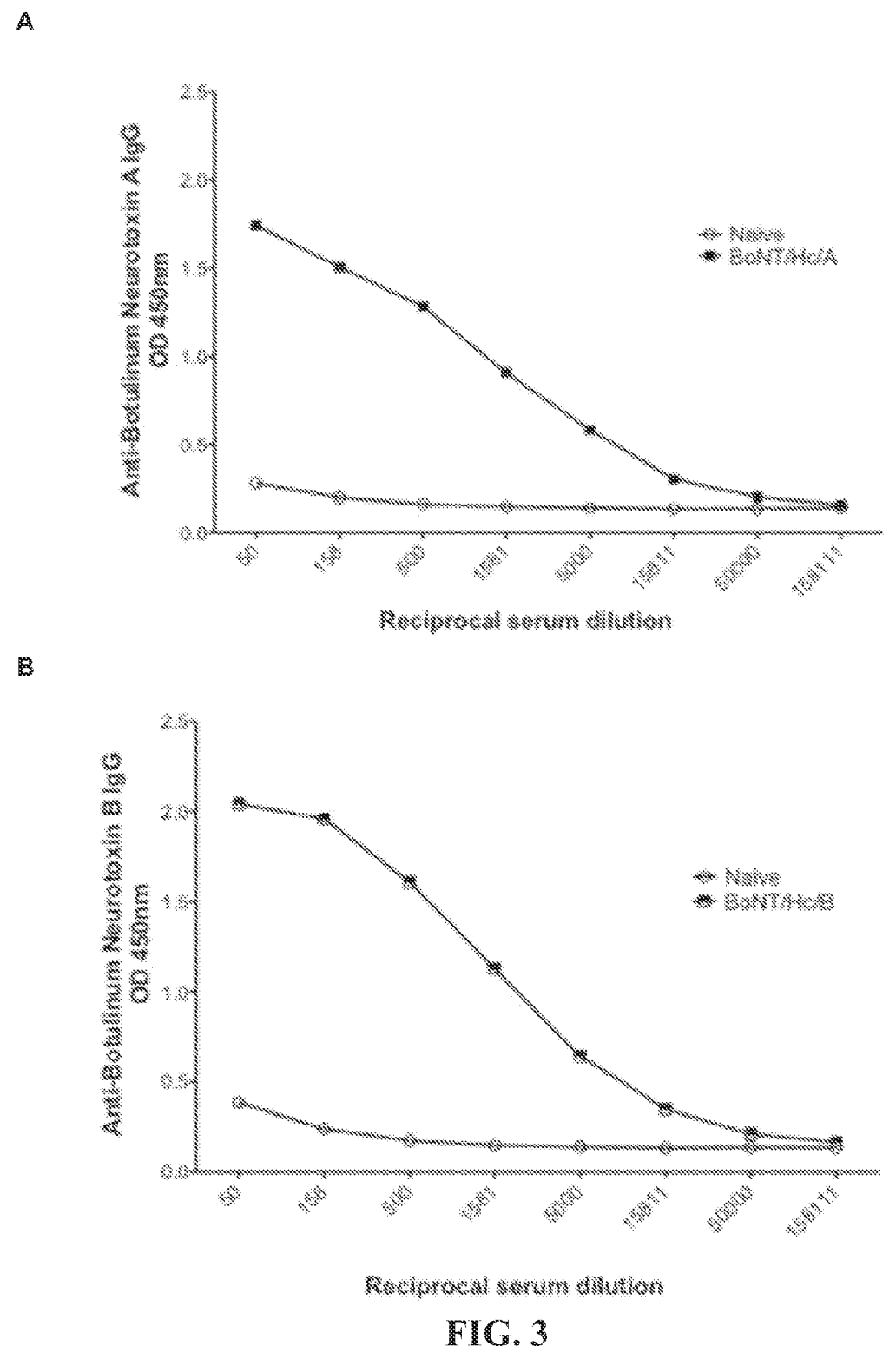
Figure 3:
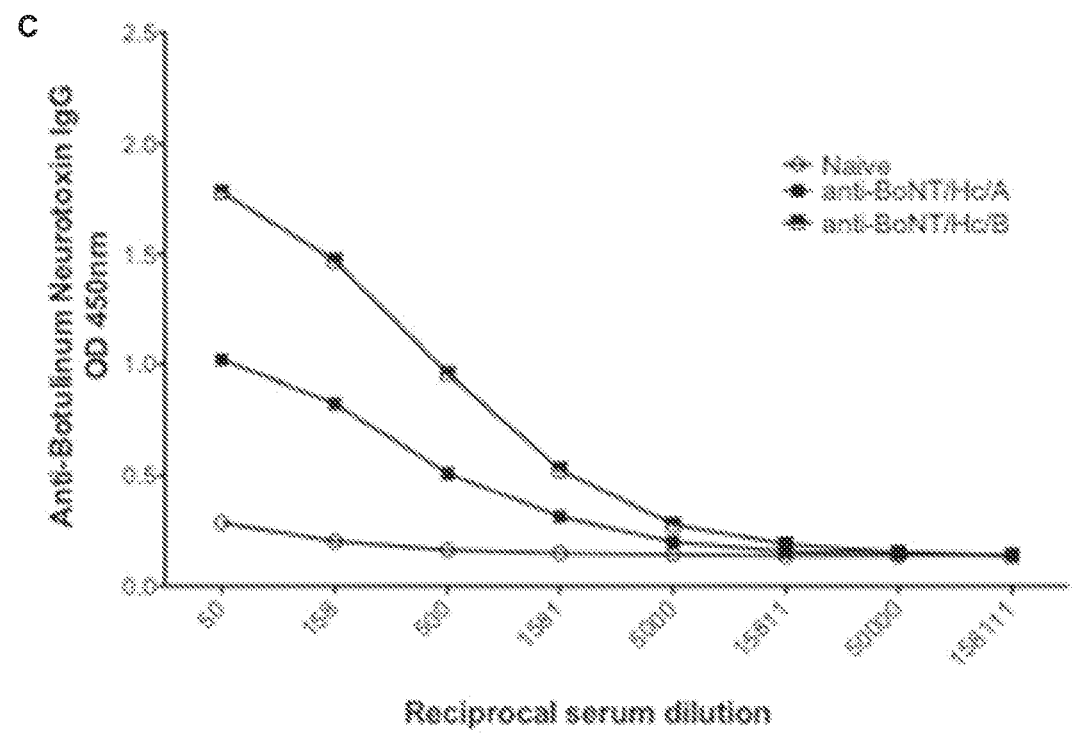

Group 1 included 5 mice immunized with the BoNT/Hc/A monovalent vaccine and 5 control mice (i.e., naïve). Anti-botulinum neurotoxin A IgG responses in serum are shown in FIG. 3A. Clear circle represented naïve mice and shaded square represented BoNT/Hc/A-immunized mice.

Group 2 included 5 mice immunized with BoNT/Hc/B monovalent vaccine and 5 control mice (i.e., naïve). Anti-botulinum neurotoxin B IgG responses in serum are shown in FIG. 3B. Clear circle represented naïve mice and half-shaded square represented BoNT/Hc/B-immunized mice.

Group 3 included 5 mice immunized with BoNT/Hc/AB bivalent vaccine and 5 control mice (i.e., naïve). Anti-botulinum neurotoxin A and B IgG responses in serum are shown in FIG. 3C. Clear circle represented naïve mice. Mice immunized with the BoNT/Hc/AB bivalent vaccine produced antibodies against the heavy chains of neurotoxins A (i.e., shaded square) and B (i.e., half-shaded square).

The above data showed that the BoNT/Hc/A monovalent vaccine and the BoNT/Hc/B monovalent vaccine produced specific antibodies against the heavy chains of neurotoxins A and B, respectively. The above data also showed that the BoNT/Hc/AB bivalent vaccine produced specific antibodies against the heavy chains of neurotoxins A and B. Accordingly, the monovalent and bivalent vaccines were able to induce a specific humoral response against the botulinum neurotoxins.

Example 4

Lethal Challenge with *Clostridium botulinum* Neurotoxin

The constructs described above in Example 1 and illustrated in FIG. 1 were further analyzed to evaluate whether such constructs would be effective vaccines. Specifically, Balb/c mice immunized with either a monovalent BoNT/Hc construct (i.e., vaccine) or a bivalent BoNT/Hc vaccine were challenged with a lethal dose of the respective botulinum neurotoxin to assess whether the vaccines prevented disease (i.e., death) in the immunized Balb/c mice.

Three groups of mice were immunized as detailed below. After completion of the immunization schedule, each group of mice was administered or challenged intraperitoneal (i.p.) with $10^2$ LD50 of the respective serotype(s) of *C. botulinum*. The protective ability of the BoNT/Hc vaccines was measured as a percentage of the mice surviving the challenge.

Group 1 included three types of mice: (a) mice immunized with an optimal dosage of BoNT/Hc/A monovalent vaccine before challenge with neurotoxin A (i.e., filled triangle in FIG. 4A); (b) unimmunized mice (i.e., naïve) challenged with neurotoxin A (i.e., open circle in FIG. 4A); and (c) unchallenged mice receiving a neurotoxin diluent (i.e., Gel-NaH$_2$PO$_4$) as a negative control (i.e., open square in FIG. 4A). As shown in FIG. 4A, 100% of immunized mice survived the challenge of a lethal dose of neurotoxin A while the challenged naïve mice were dead by 6 hours.

Group 2 included three types of mice: (a) mice immunized with an optimal dosage of BoNT/Hc/B monovalent vaccine before challenge with neurotoxin B (i.e., filled triangle in FIG. 4B); (b) unimmunized mice (i.e., naïve) challenged with neurotoxin B (i.e., open circle in FIG. 4B); and (c) unchallenged mice receiving a neurotoxin diluent (i.e., Gel-NaH$_2$PO$_4$) as a negative control (i.e., open square in FIG. 4B). As shown in FIG. 4B, 100% of immunized mice survived the challenge of a lethal dose of neurotoxin B while the challenged naïve mice were dead by 24 hours.

Group 3 included four types of mice: (a) mice immunized with an optimal dosage of BoNT/Hc/AB bivalent vaccine before challenge with neurotoxins A and B (i.e., filled triangle in FIG. 4C); (b) unimmunized mice (i.e., naïve) challenged with neurotoxin A (i.e., circle with half horizontal fill in FIG. 4C); (c) unimmunized mice (i.e., naïve) challenged with neurotoxin B (i.e., circle with half vertical fill in FIG. 4C); and (d) unchallenged mice receiving a neurotoxin diluent (i.e., Gel-NaH$^2$PO$^4$) as a negative control (i.e., open square in FIG. 4C). As shown in FIG. 4C, about 75% of immunized mice survived the challenge of a lethal dose of neurotoxins A and B. The naïve mice challenged with neurotoxin A were dead by 6 hours, and the naïve mice challenged with neurotoxin B were dead by 24 hours.

The above data showed that the BoNT/Hc/A monovalent vaccine and the BoNT/Hc/B monovalent vaccine protected Balb/c mice from death via a lethal dose of neurotoxin A and neurotoxin B, respectively. Particularly, the monovalent vaccines afforded 100% protection (i.e., no death) to the respective neurotoxin in the immunized mice. The above data also showed that the BoNT/Hc/AB bivalent vaccine significantly protected Balb/c mice from death via a lethal dose of neurotoxins A and B. Accordingly, the monovalent and bivalent vaccines were able to protect immunized mice from disease.

Example 5

Methods for the Immunogenicity and Challenge Studies of Examples 6-9

The constructs described above in Example 1 and illustrated in FIG. 1A were further analyzed to evaluate the induced immune responses and protection to neurotoxin challenge following immunization with these constructs. Specifically, the constructs were studied in monovalent vaccines and a trivalent vaccine using the scheme illustrated in FIG. 5 and described below.

Monovalent Vaccines. Six groups of Balb/c mice were included in this study. Each group contained five mice. The six groups were used in immunogenicity studies. Another six groups of mice were used in studies that challenged the mice with neurotoxin from *Clostridium botulinum*.

Group 1 mice were not vaccinated (i.e., naïve or control mice) while Group 2 mice were vaccinated twice with the BoNT/Hc/A monovalent vaccine. Each vaccination administered 10 μg of the BoNT/Hc/A construct intramuscularly and three weeks separated the vaccinations.

Group 3 mice were not vaccinated (i.e., naïve or control mice) while Group 4 mice were vaccinated twice with the BoNT/Hc/B monovalent vaccine. Each vaccination administered 10 μg of the BoNT/Hc/B construct intramuscularly and three weeks separated the vaccinations.

Group 5 mice were not vaccinated (i.e., naïve or control mice) while Group 6 mice were vaccinated twice with the BoNT/Hc/E monovalent vaccine. Each vaccination administered 10 μg of the BoNT/Hc/E construct intramuscularly and three weeks separated the vaccinations.

For each group, sera were collected from each mouse prior to each vaccination (i.e., week 0 and week 3 in FIG. 5). At the endpoint of the immunogenicity studies, sera were again collected along with tissues from each sacrificed mice (i.e., week 6 (3 weeks post-final immunization) in FIG. 5).

In the neurotoxin challenge studies, animals were challenged with the respective neurotoxin four weeks post-final immunization (i.e., week 7 in FIG. 5). The neurotoxin was administered intraperitoneally (i.p.). After challenge, the mice were monitored for symptoms of intoxication, namely reduced physical activity, impaired motor function, respiratory distress, flaccid paralysis, and respiratory failure and assigned a clinical score of 1 to 5 with 5 being the highest score for each symptom.

Specifically, animals in Groups 1 and 2 were each challenged with $10^2$ $LD_{50}$ of neurotoxin from serotype A. Animals in Groups 3 and 4 were each challenged with $10^2$ $LD_{50}$ of neurotoxin from serotype B. Animals in Groups 5 and 6 were each challenged with $10^2$ $LD_{50}$ of neurotoxin from serotype E. At the endpoint of the neurotoxin challenge studies (i.e., week 8 (1 week after challenge) in FIG. 5), animals were sacrificed.

Trivalent Vaccine.

Figure 10:
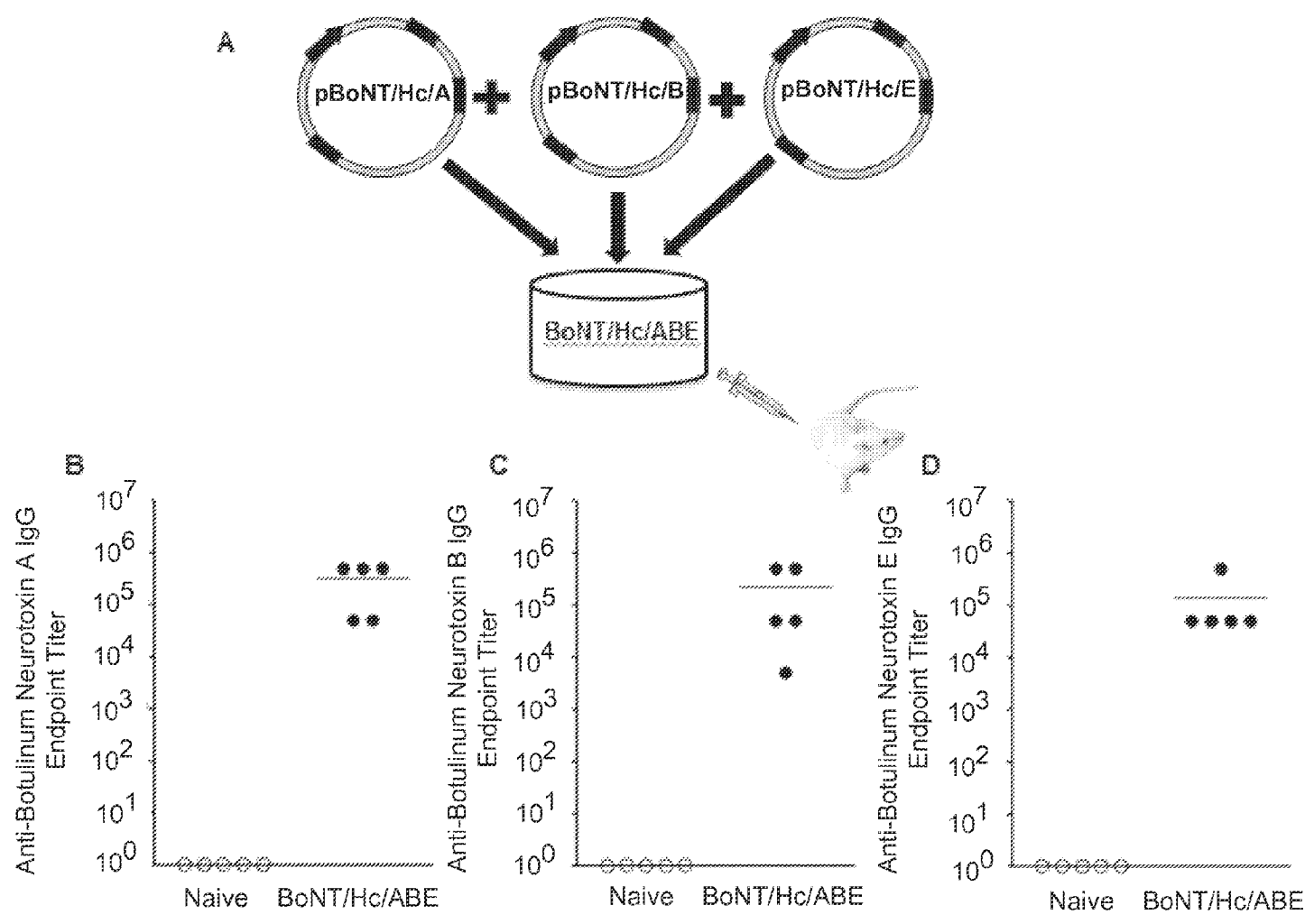

The trivalent vaccine was a mixture of the BoNT/Hc/A, BoNT/Hc/B, and BoNT/Hc/E constructs (FIG. 10A). Six groups of Balb/c mice were included in this study. Each group contained five mice. The six groups were used in immunogenicity studies. Another six groups of mice were used in studies that challenged the mice with neurotoxin from *Clostridium botulinum*.

Groups 1, 3, and 5 mice were not vaccinated (i.e., naïve or control mice) while Groups 2, 4, and 6 mice were vaccinated twice with the trivalent vaccine. Each vaccination administered 30 μg of the trivalent vaccine (i.e., 10 μg of the BoNT/Hc/A construct, 10 μg of the BoNT/Hc/B construct, and 10 μg of the BoNT/Hc/E construct) intramuscularly and three weeks separated the vaccinations.

For each group, sera were collected from each mouse prior to each vaccination (i.e., week 0 and week 3 in FIG. 5). At the endpoint of the immunogenicity studies, sera were again collected along with tissues from each sacrificed mice (i.e., week 6 (3 weeks post-final immunization) in FIG. 5).

In the neurotoxin challenge studies, animals in Groups 1 and 2 were each challenged with $10^2$ $LD_{50}$ of neurotoxin from serotype A. Animals in Groups 3 and 4 were each challenged with $10^2$ $LD_{50}$ of neurotoxin from serotype B. Animals in Groups 5 and 6 were each challenged with $10^2$ $LD_{50}$ of neurotoxin from serotype E. Specifically, animals were challenged with the respective neurotoxin four weeks post-final immunization (i.e., week 7 in FIG. 5). The neurotoxin was administered intraperitoneally (i.p.). After challenge, the mice were monitored for symptoms of intoxication, namely reduced physical activity, impaired motor function, respiratory distress, flaccid paralysis, and respiratory failure and assigned a clinical score of 1 to 5 with 5 being the highest score for each symptom. At the endpoint of the neurotoxin challenge studies (i.e., week 8 (1 week after challenge) in FIG. 5), animals were sacrificed.

Example 6

Humoral Immune Response Induced by Monovalent Vaccines

Immunogenicity studies were carried out using monovalent vaccines containing the BoNT/Hc/A, BoNT/Hc/B, or BoNT/Hc/E construct Immunization with the monovalent vaccines was performed as described above in Example 6 under monovalent vaccines and as illustrated in FIG. 5. The immunogenicity studies examined the titer of antibodies reactive to the *Clostridium botulinum* neurotoxin in the collected sera.

After immunization, the immunoglobulin G (IgG) titer in the sera collected at the endpoint of the study (i.e., 3 weeks post-final immunization) was measured by enzyme-linked immunosorbent assay (ELISA). Specifically, the titer of IgG antibodies that were reactive with the respective neurotoxin was measured by ELISA.

Figure 6:
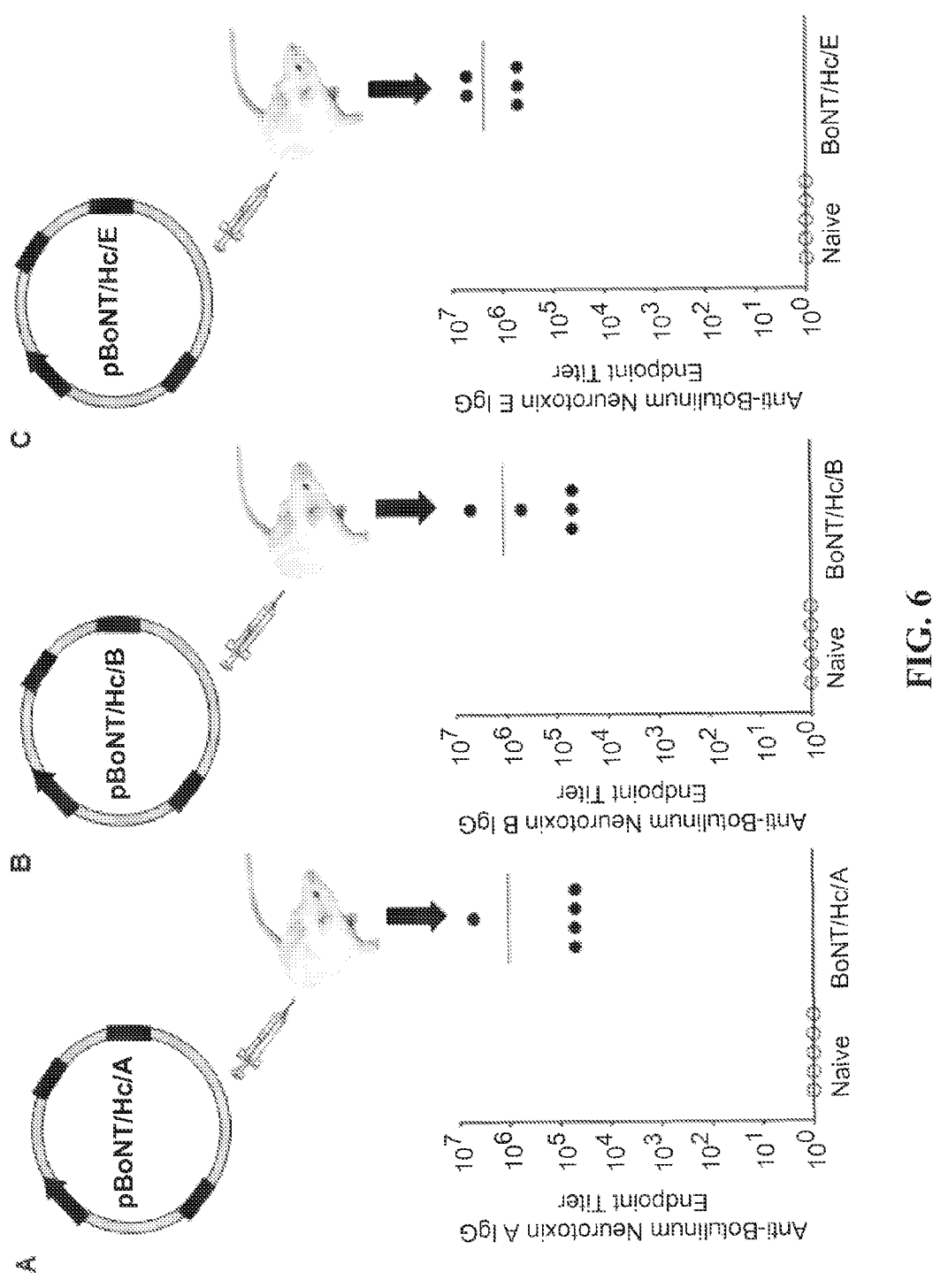

In each of FIGS. 6A, 6B, and 6C, the circles represented the titer measured in sera collected from each mouse while the horizontal line represented the mean titer for each group. As shown in FIG. 6A, mice vaccinated with the monovalent vaccine containing the BoNT/Hc/A construct had high titers of IgG antibody that was reactive to neurotoxin from serotype A as compared to the naïve mice. Mice vaccinated with the monovalent vaccine containing the BoNT/Hc/B construct had high titers of IgG antibody that was reactive to neurotoxin from serotype B as compared to naïve mice (FIG. 6B). Mice vaccinated with the monovalent vaccine containing the BoNT/Hc/E construct had high titers of IgG antibody that was reactive to neurotoxin from serotype E as compared to naïve mice (FIG. 6C). These data demonstrated that each monovalent vaccine induced a strong humoral immune response that was reactive to the respective neurotoxin serotype.

Example 7

The Monovalent Vaccines Protect Against Lethal Challenge with *Clostridium botulinum* Neurotoxin Studies were performed using the monovalent vaccines containing the BoNT/Hc/A, BoNT/Hc/B, or BoNT/Hc/E constructs to determine if the monovalent vaccines protected against lethal challenge with the *Clostridium botulinum* neurotoxin. Immunization with the monovalent vaccines was performed as described above in Example 6 under monovalent vaccines and as illustrated in FIG. 5. The challenge studies examined the percent survival to lethal challenge and scored clinical symptoms of intoxication, namely reduced physical activity, impaired motor function, respiratory distress, flaccid paralysis, and respiratory failure.

After immunization, groups 1 to 6 were administered a lethal dose of the respective neurotoxin as described above in Example 6 under monovalent vaccines. Additionally, Balb/c mice that were not challenged with neurotoxin were administered the diluent (i.e, Gel-NaH$_2$PO$_4$) for the neurotoxin as a control for any effects attributable to the diluent.

Figure 7:
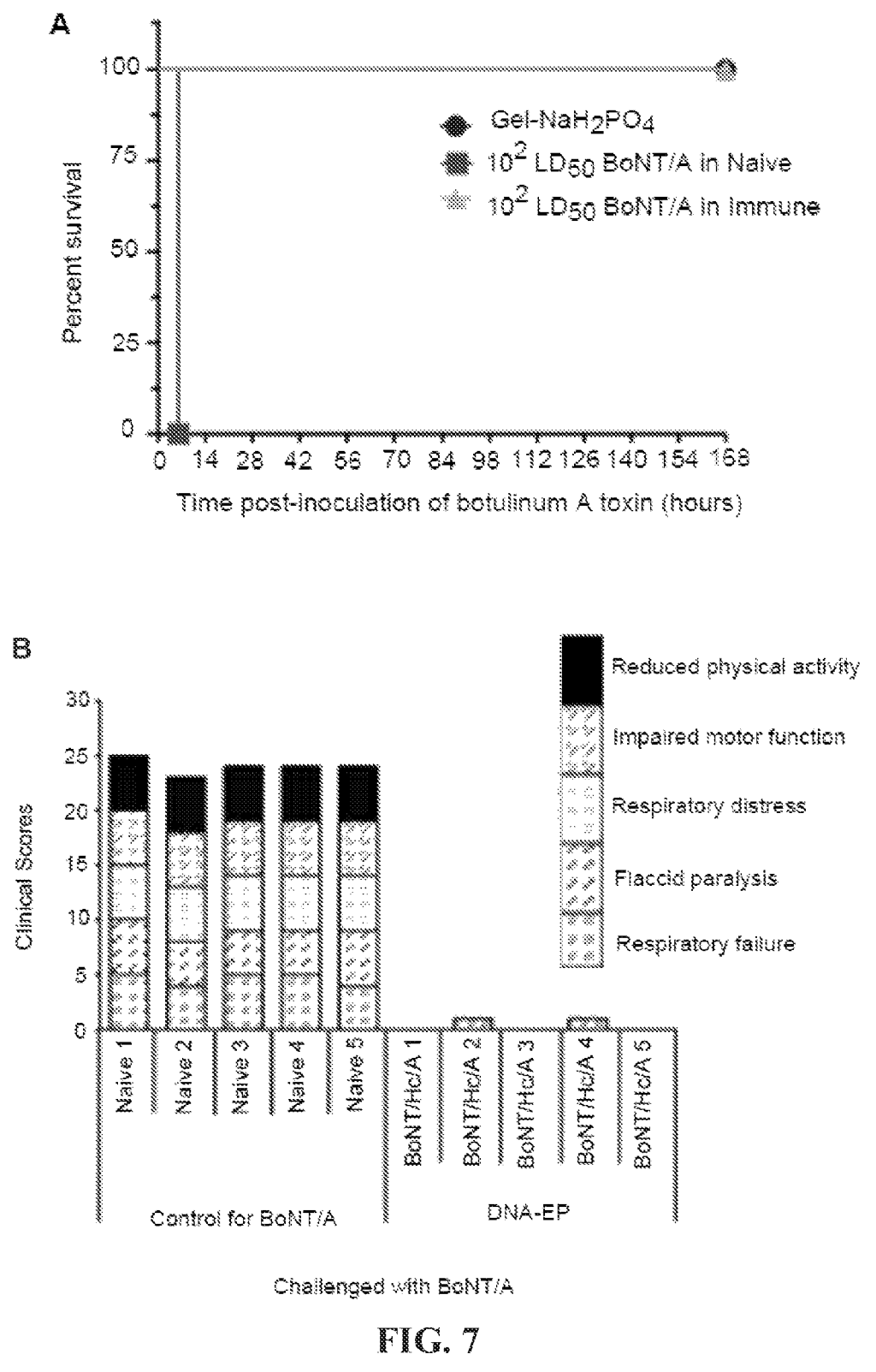
Figure 8:
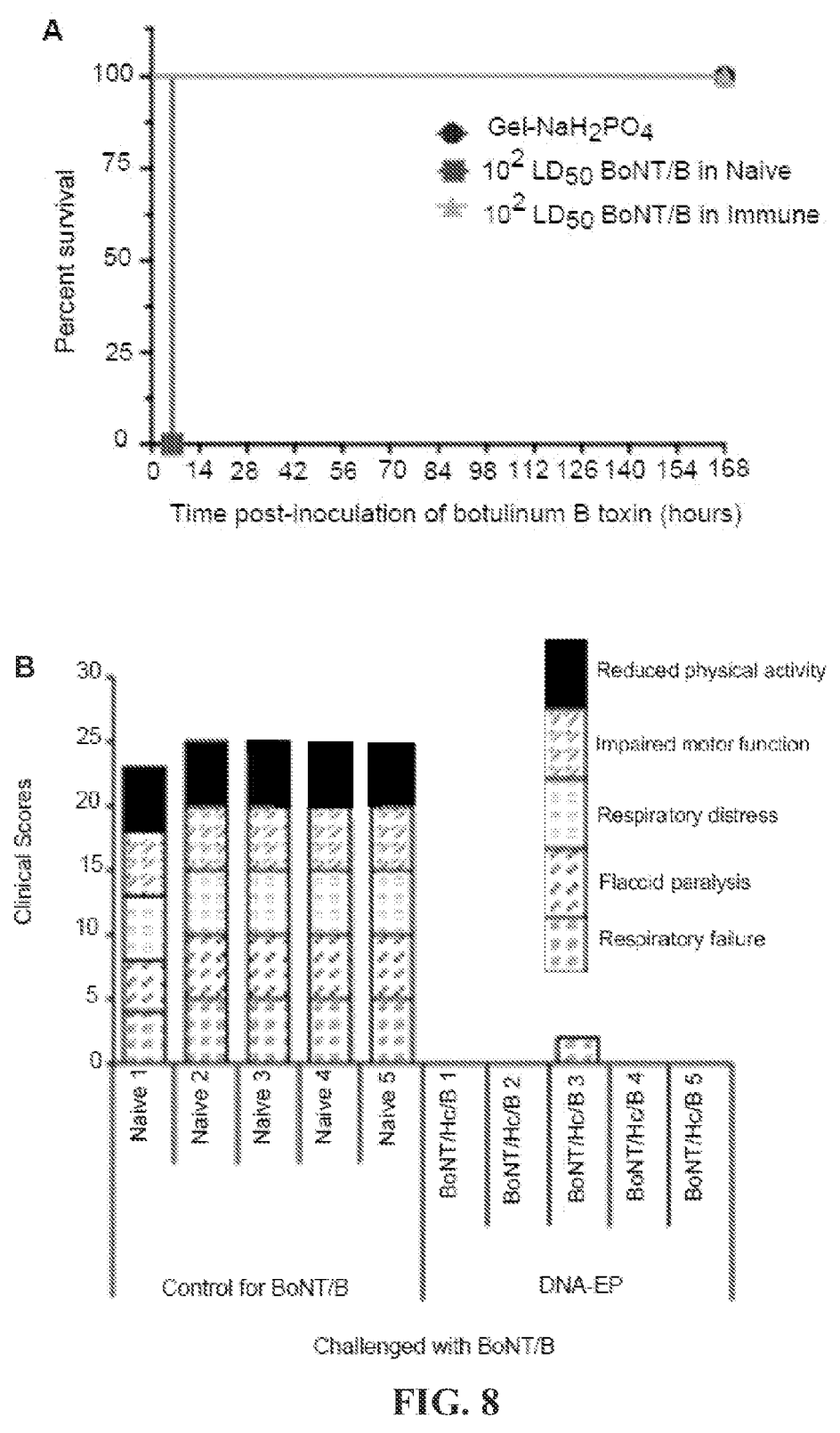
Figure 9:
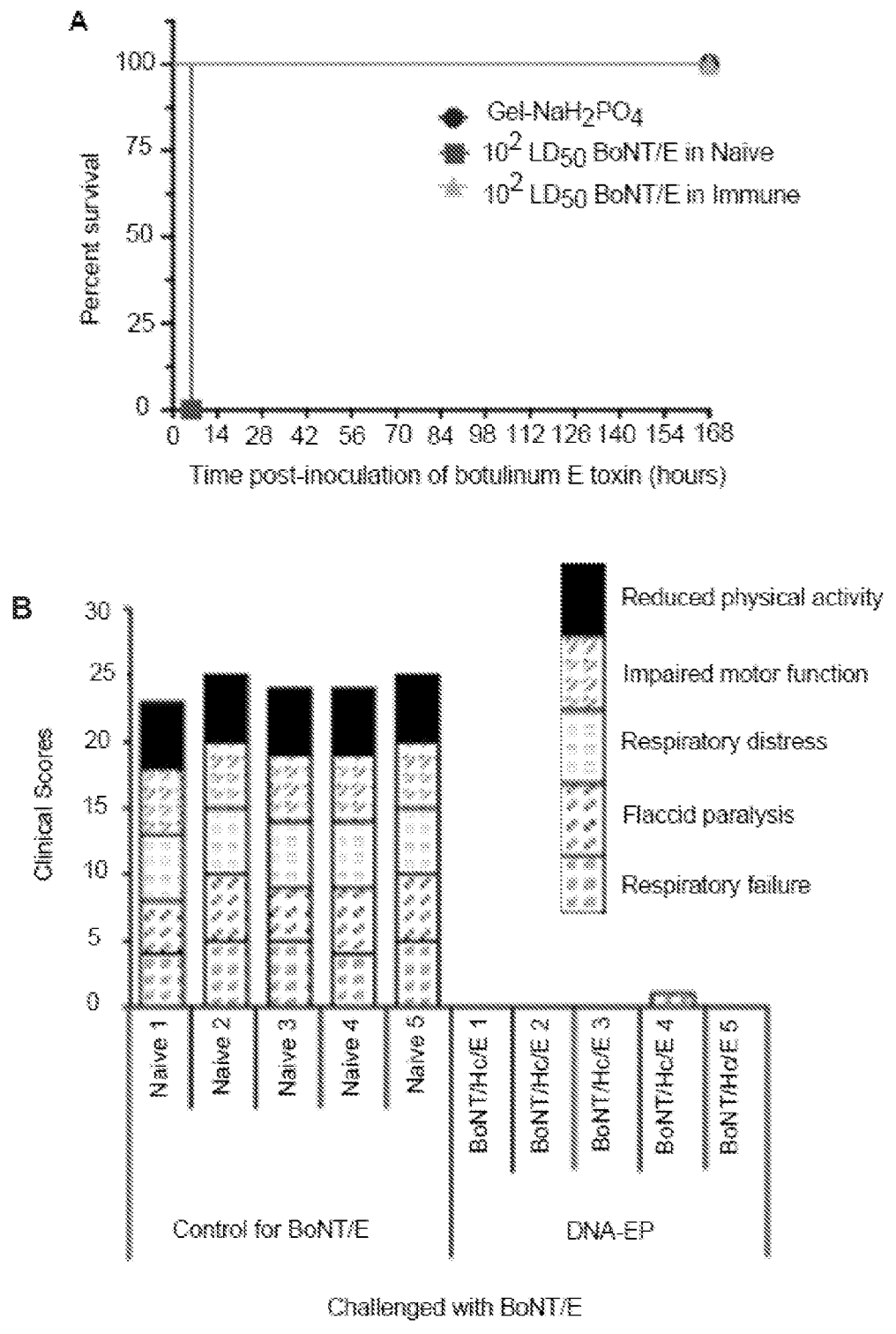

FIGS. 7A, 8A, and 9A show the survival results from the study using Kaplan-Meier survival curves. FIGS. 7B, 8B, and 9B show the results from the clinical scoring of the symptoms of intoxication for each animal in groups 1 to 6. The data shown in FIGS. 7A, 7B, 8A, 8B, 9A, and 9B are the average results of three independent experiments.

As shown in FIG. 7A, 100% of mice vaccinated with the BoNT/Hc/A construct (triangle) survived the challenge with a lethal dose of neurotoxin from serotype A while 100% of the naïve mice (square) died within 14 hours of receiving the lethal dose. 100% of mice receiving the diluent also survived the study, thereby indicating that the diluent had no effect on survival (circle in FIG. 7A). Additionally, the naïve mice scored highly for the symptoms of intoxication while the mice vaccinated with the BoNT/Hc/A construct exhibited few to no symptoms of intoxication (FIG. 7B). Accordingly, these data indicated that immunization with the monovalent vaccine containing the BoNT/Hc/A construct provided complete protection (i.e., 100% survival or no death) against the neurotoxin from *Clostridium botulinum* serotype A with few to no symptoms of intoxication.

As shown in FIG. 8A, 100% of mice vaccinated with the BoNT/Hc/B construct (triangle) survived the challenge with a lethal dose of neurotoxin from serotype B while 100% of the naïve mice (square) died within 14 hours of receiving the lethal dose. 100% of mice receiving the diluent also survived the study, thereby indicating that the diluent had no effect on survival (circle in FIG. 8A). Additionally, the naïve mice scored highly for symptoms of intoxication while the mice vaccinated with the BoNT/Hc/B construct exhibited few to no symptoms of intoxication (FIG. 8B). Accordingly, these data indicated that immunization with the monovalent vaccine containing the BoNT/Hc/B construct provided complete protection (i.e., 100% survival or no death) against the neurotoxin from *Clostridium botulinum* serotype B with few to no symptoms of intoxication.

As shown in FIG. 9A, 100% of mice vaccinated with the BoNT/Hc/E construct (triangle) survived the challenge with a lethal dose of neurotoxin from serotype C while 100% of the naïve mice (square) died within 14 hours of receiving the lethal dose. 100% of mice receiving the diluent also survived the study, thereby indicating that the diluent had no effect on survival (circle in FIG. 9A). Additionally, the naïve mice scored highly for symptoms of intoxication while the mice vaccinated with the BoNT/Hc/E construct exhibited few to no symptoms of intoxication (FIG. 9B). Accordingly, these data indicated that immunization with the monovalent vaccine containing the BoNT/Hc/E construct provided complete protection (i.e., 100% survival or no death) against the neurotoxin from *Clostridium botulinum* serotype E with few to no symptoms of intoxication.

In summary, the monovalent vaccine including the BoNT/Hc/A, BoNT/Hc/B, or BoNT/Hc/E construct provided 100% survival of exposure to a lethal amount of neurotoxin from *Clostridium botulinum* serotypes A, B, or E, respectively.

Example 8

Humoral Immune Response Induced by a Trivalent Vaccine

Immunogenicity studies were carried out using a trivalent vaccine containing the BoNT/Hc/A, BoNT/Hc/B, and BoNT/Hc/E constructs Immunization with the trivalent vaccine was performed as described above in Example 6 under trivalent vaccine and as illustrated in FIG. 5. The immunogenicity studies examined the titer of antibodies reactive to the *Clostridium botulinum* neurotoxin in the collected sera.

After immunization, the IgG titer in the sera collected at the endpoint of the study (i.e., 3 weeks post-final immunization) was measured by ELISA. Specifically, the titer of IgG antibodies that were reactive to neurotoxin from serotypes A, B, or E was measured by ELISA.

In each of FIGS. 10B, 10C, and 10D, the circles represented the titer measured in the sera collected from each mouse while the horizontal line represented the mean titer for each group. As shown in FIGS. 10B, 10C, and 10D, mice vaccinated with the trivalent vaccine containing the BoNT/Hc/A, BoNT/Hc/B, and BoNT/Hc/E constructs had high titers of IgG antibodies that were reactive to neurotoxin from serotypes A, B, and E. These demonstrated that the trivalent vaccine induced a strong humoral immune response that was reactive to neurotoxin subtypes A, B, and E. Accordingly, the trivalent vaccine induced an immune response that was reactive to neurotoxin from multiple serotypes of *Clostridium botulinum*, namely serotypes A, B, and E.

Example 9

The Trivalent Vaccine Protects Against Lethal Challenge with *Clostridium botulinum* Neurotoxin The trivalent vaccine containing the BoNT/Hc/A, BoNT/Hc/B, and BoNT/Hc/E constructs was further examined to determine if the trivalent vaccine protected against lethal challenge with the *Clostridium botulinum* neurotoxin Immunization with the trivalent vaccine was performed as described above in Example 6 under trivalent vaccine and as illustrated in FIG. 5. The challenge study examined the percent survival to lethal challenge and scored clinical symptoms of intoxication, namely reduced physical activity, impaired motor function, respiratory distress, flaccid paralysis, and respiratory failure.

After immunization, groups 1 to 6 were administered a lethal dose of the neurotoxin from *Clostridium botulinum* serotype A, B or E as described above in Example 6 under trivalent vaccine. Additionally, Balb/c mice that were not challenged with neurotoxin were administered the diluent (i.e., Gel-NaH$_2$PO$_4$) for the neurotoxin as a control for any effects attributable to the diluent.

Figure 11:
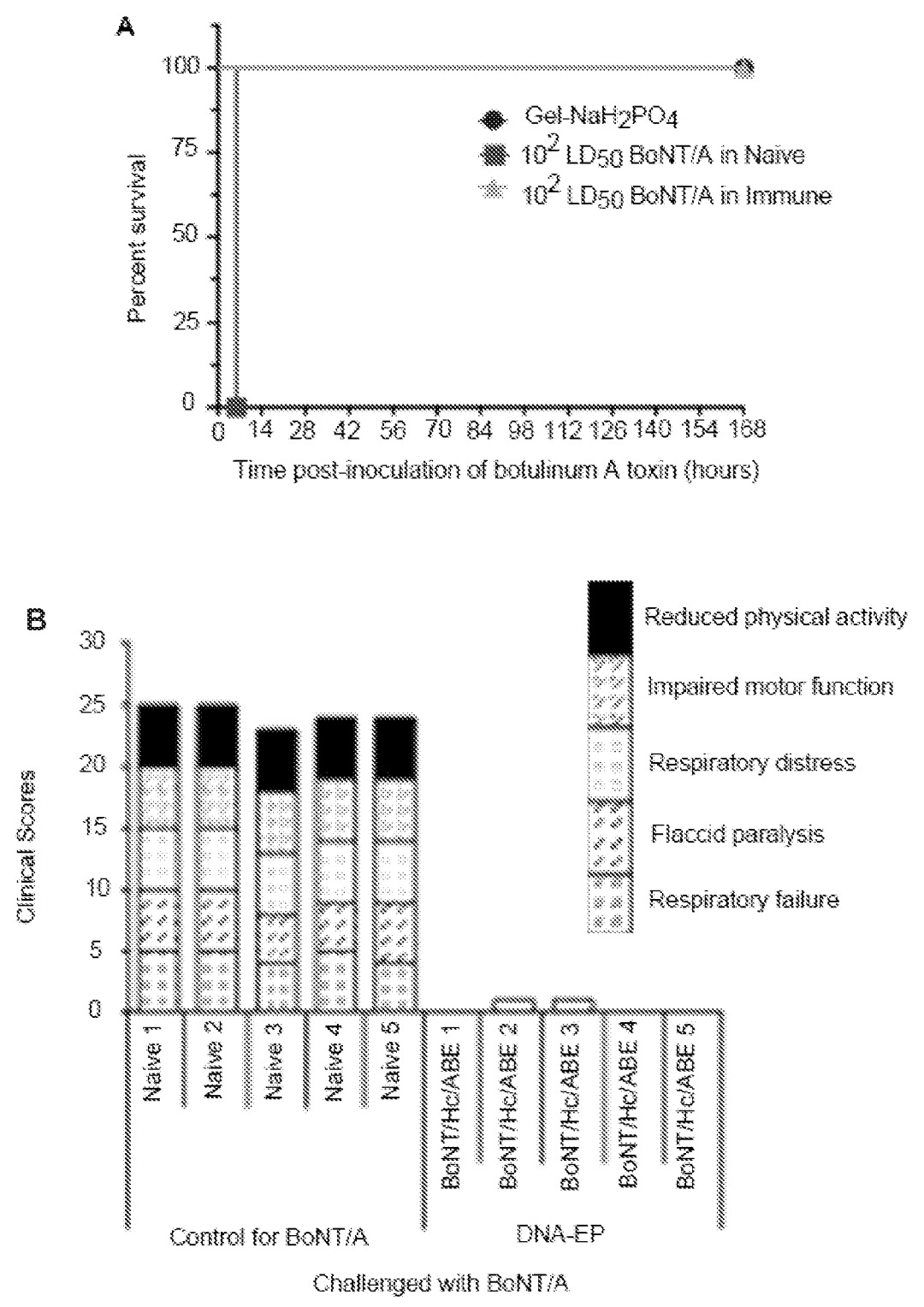
Figure 11:
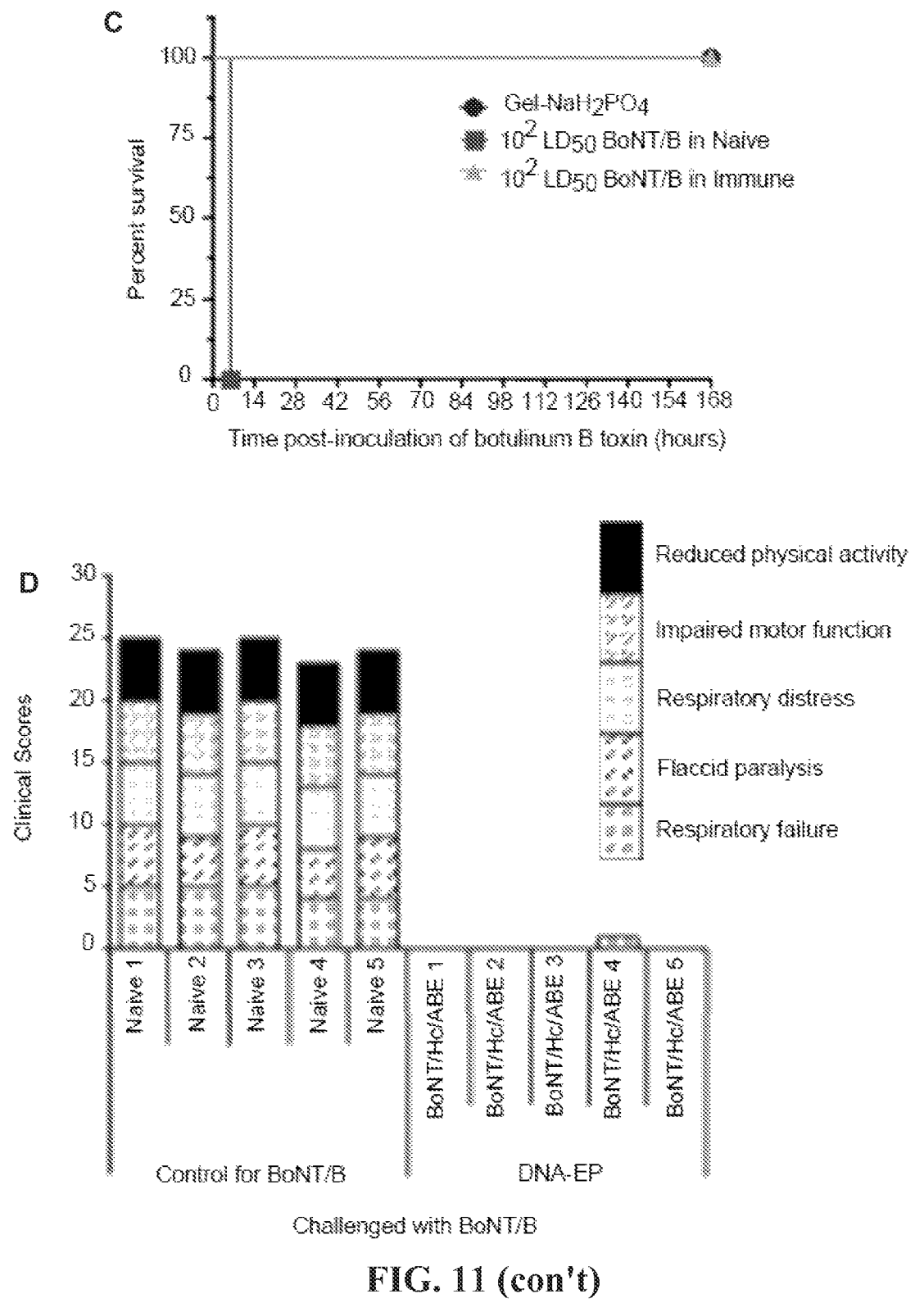
Figure 11:
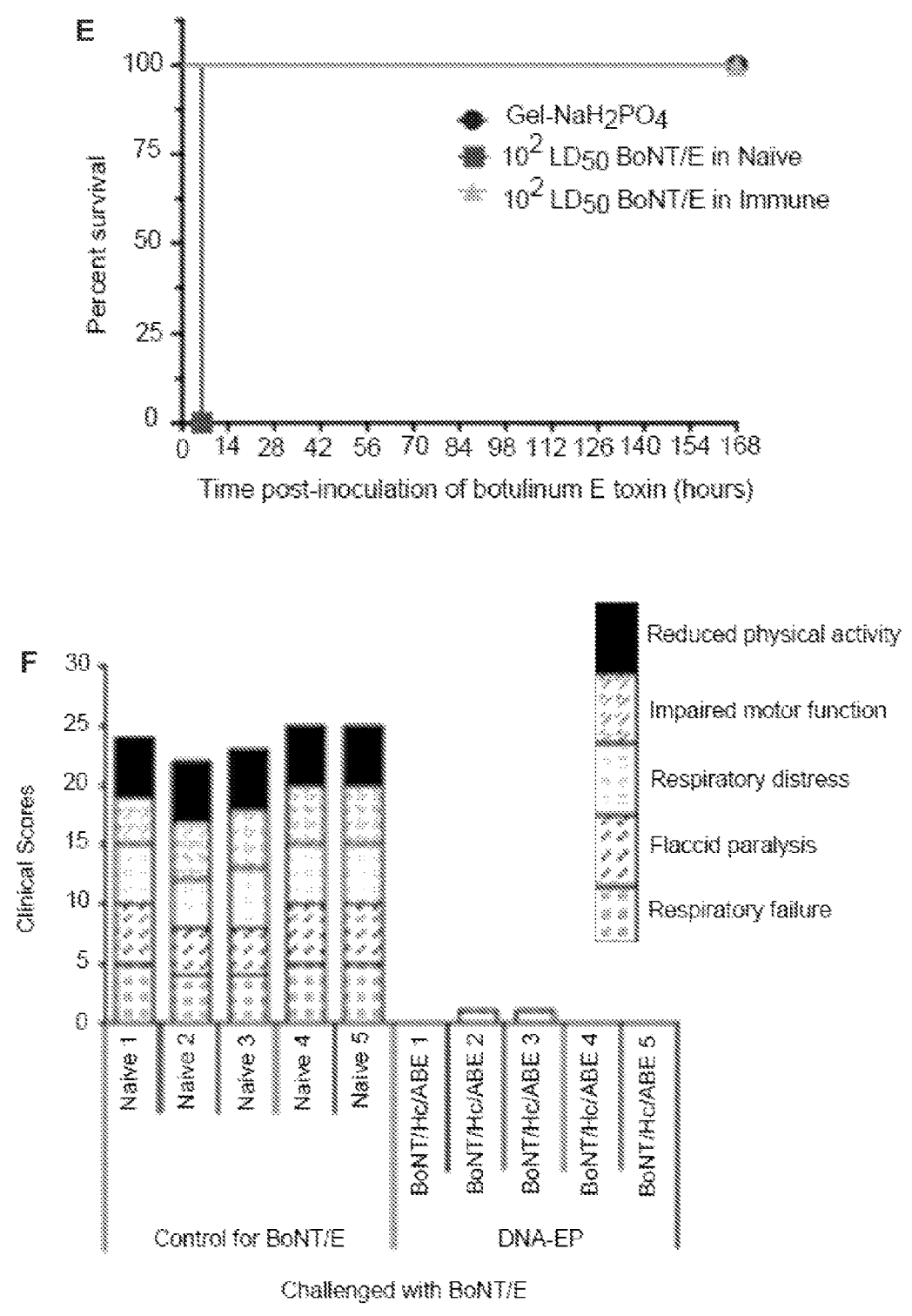

FIGS. 11A, 11C, and 11E show the survival results from the study using Kaplan-Meier survival curves. FIGS. 11B, 11D, and 11F show the results from the clinical scoring of the symptoms of intoxication for each animal in groups 1 to 6.

As shown in FIGS. 11A, 11C, and 11E, 100% of mice vaccinated with the trivalent vaccine (i.e., BoNT/Hc/ABE; triangle) survived challenge with a lethal dose of neurotoxin from serotypes A, B, and E, respectively, while 100% of the naïve mice (square) died within 14 hours of receiving the lethal dose. 100% of mice receiving the diluent also survived the study, thereby indicating that the diluent had no effect on survival (circle in FIGS. 11A, 11C, and 11E). Additionally, the naïve mice scored highly for the symptoms of intoxication while the mice vaccinated with the trivalent vaccine (i.e., BoNT/Hc/ABE) exhibited few to no symptoms of intoxication (FIGS. 11B, 11D, and 11F). Accordingly, these data indicated that immunization with the trivalent vaccine containing the BoNT/Hc/A, BoNT/Hc/B, and BoNT/Hc/E constructs provided complete protection (i.e., 100% survival or no death) against the neurotoxin from *Clostridium botulinum* serotypes A, B, and E with few to no symptoms of intoxication. Furthermore, the trivalent vaccine provided equally effective protection (i.e., 100% survival) against neurotoxin from serotypes A, B, and E.

Example 10

Figure 12:
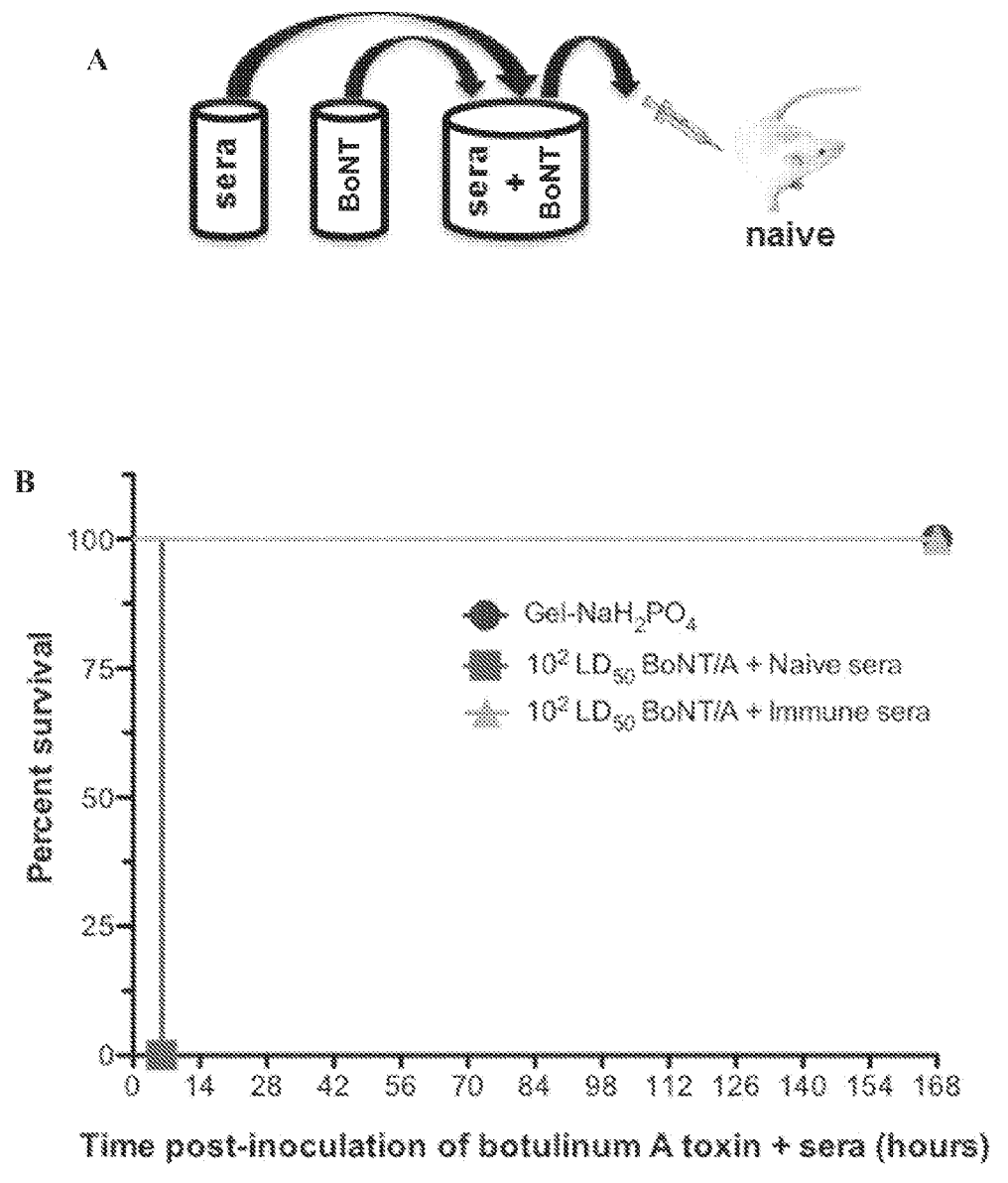
Figure 12:
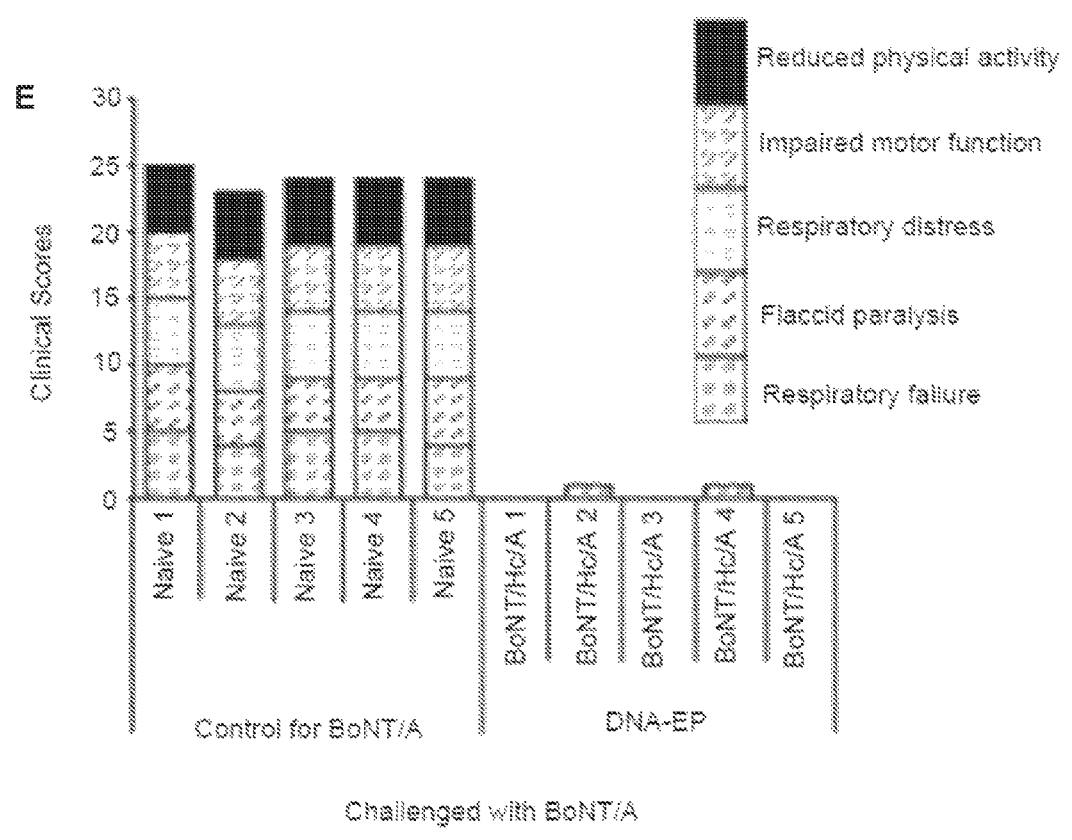
Figure 12:
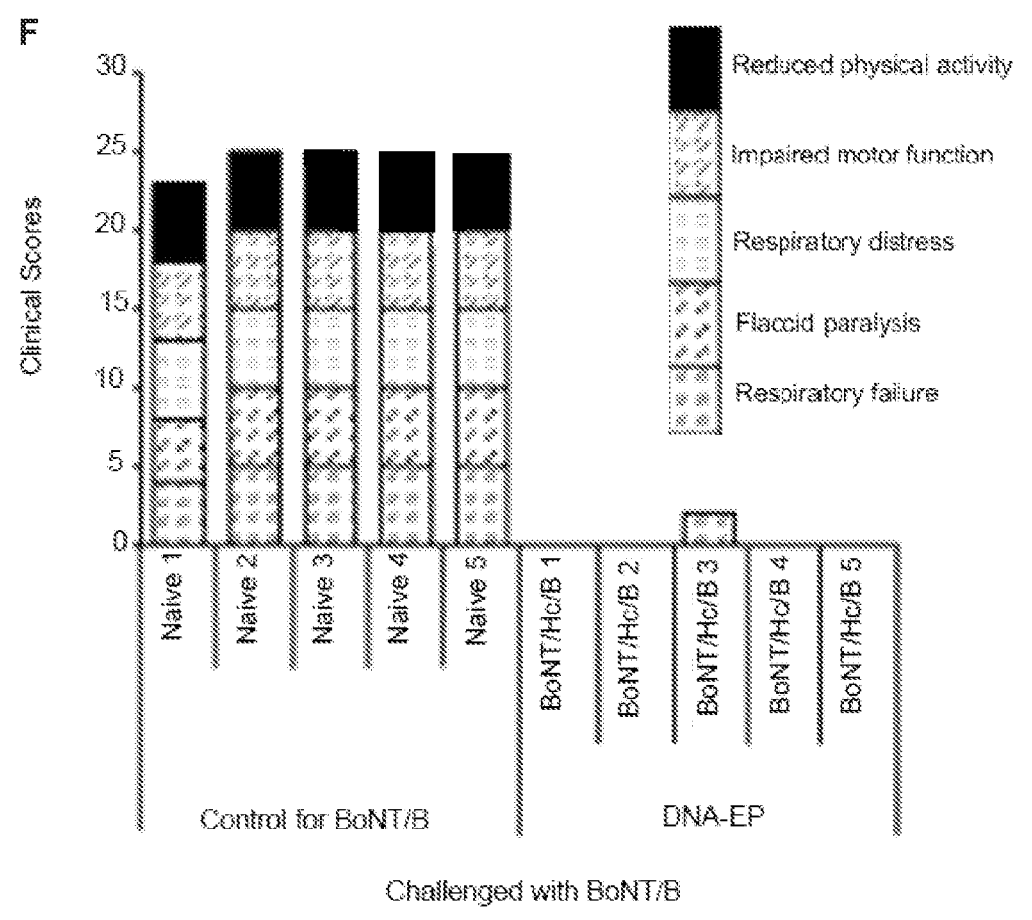
Figure 12:
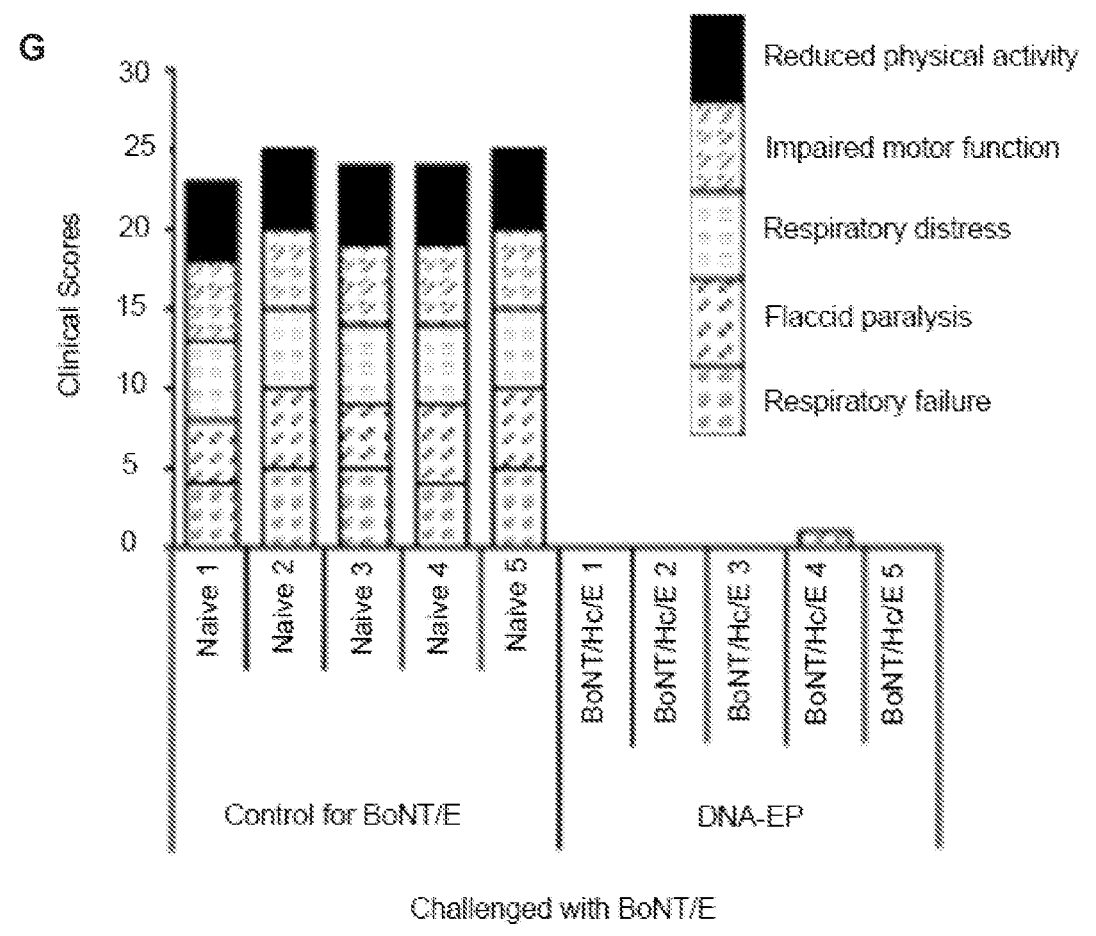

Antibodies Induced by the Monovalent Vaccines Protect Against Lethal Challenge with *Clostridium botulinum* Neurotoxin The constructs described above in Example 1 and illustrated in FIG. 1A were further examined to determine if neutralizing antibodies were induced by the monovalent vaccines. Balb/c mice were used in this study. Specifically, sera were collected from naïve mice (i.e., mice not vaccinated with a monovalent vaccine), mice immunized with the monovalent vaccine containing the BoNT/Hc/A construct, mice immunized with the monovalent vaccine containing the BoNT/Hc/B construct, and mice immunized with the monovalent vaccine containing the BoNT/Hc/E construct. The sera were then mixed with the respective neurotoxin, namely 600 µl of sera from BoNT/Hc/A, BoNT/Hc/B, and BoNT/Hc/E vaccinated mice was mixed 1:1 with $10^2$ LD$_{50}$ of neurotoxin from *Clostridium botulinum* serotypes A, B, and E, respectively (FIG. 12A). Sera from the naïve mice were independently mixed 1:1 with neurotoxin from serotypes A, B, and E. The sera:toxin mixtures were incubated at 37 degrees Celsius for 1 hour.

200 µl of each sera:toxin mixture was then administered intraperitoneal (i.p.) to a respective group of naïve mice (i.e., mice not immunized with the monovalent vaccine). Each group had five mice. The mice were monitored for seven days for survival and clinical symptoms of disease (i.e., intoxication), namely respiratory failure, flaccid paralysis, respiratory distress, impaired motor function, and reduced physical activity. In particular, each clinical symptom was assigned a score of one to five with five being the highest score. Additionally, another group of mice was included in the study that was administered the diluent (i.e., Gel-NaH$_2$PO$_4$) for the neurotoxin instead of the sera:toxin mixture as a control for any effects attributable to the diluent.

FIGS. 12B, 12C, and 12D show the percent survival results using Kaplan-Meier survival curves. FIGS. 12E, 12F, and 12G show the results of clinical scoring of the symptoms of disease for each mouse.

100% of mice receiving the mixture of neurotoxin from serotype A and sera from mice immunized with the monovalent vaccine containing the BoNT/Hc/A construct survived (triangle in FIG. 12B). These mice exhibited few to no symptoms of intoxication (FIG. 12E). In contrast, 100% of mice receiving the mixture of neurotoxin from serotype A and sera from naïve mice died within 6 hours of receiving the mixture (square in FIG. 12B). These mice also scored highly for the symptoms of intoxication (FIG. 12E). 100% of mice receiving the diluent also survived the study, thereby indicating that the diluent had no effect on survival (FIG. 12B). Accordingly, these data indicated that the antibodies present in the sera from mice immunized with BoNT/Hc/A construct neutralized the neurotoxin from serotype A, thereby allowing the animals to survive the challenge with the neurotoxin. The monovalent vaccine containing the BoNT/Hc/A construct thus induced high titers of antibodies (as described above in Example 6 and FIG. 6A) and these antibodies neutralized the neurotoxin from serotype A. This monovalent vaccine provided survival of lethal doses of neurotoxin from *Clostridium botulinum* serotype A via induction of a strong humoral immune response that included neutralizing antibodies reactive to the neurotoxin.

100% of mice receiving the mixture of neurotoxin from serotype B and sera from mice immunized with the monovalent vaccine containing the BoNT/Hc/B construct survived (triangle in FIG. 12C). These mice exhibited few to no symptoms of intoxication (FIG. 12F). In contrast, 100% of mice receiving the mixture of neurotoxin from serotype B and sera from naïve mice died within 6 hours of receiving the mixture (square in FIG. 12C). These mice also scored highly for the symptoms of intoxication (FIG. 12F). 100% of mice receiving the diluent also survived the study, thereby indicating that the diluent had no effect on survival (FIG. 12C). Accordingly, these data indicated that the antibodies present in the sera from mice immunized with BoNT/Hc/B construct neutralized the neurotoxin from serotype B, thereby allowing the animals to survive the challenge with the neurotoxin. The monovalent vaccine containing the BoNT/Hc/B construct thus induced high titers of antibodies (as described above in Example 6 and FIG. 6B) and these antibodies neutralized the neurotoxin from serotype B. This monovalent vaccine provided survival of lethal doses of neurotoxin from *Clostridium botulinum* serotype B via induction of a strong humoral immune response that included neutralizing antibodies reactive to the neurotoxin.

100% of mice receiving the mixture of neurotoxin from serotype E and sera from mice immunized with the monovalent vaccine containing the BoNT/Hc/E construct survived (triangle in FIG. 12D). These mice exhibited few to no symptoms of intoxication (FIG. 12G). In contrast, 100% of mice receiving the mixture of neurotoxin from serotype A and sera from naïve mice died within 6 hours of receiving the mixture (square in FIG. 12D). These mice also scored highly for the symptoms of intoxication (FIG. 12G). 100% of mice receiving the diluent also survived the study, thereby indicating that the diluent had no effect on survival (FIG. 12D). Accordingly, these data indicated that the antibodies present in the sera from mice immunized with BoNT/Hc/E construct neutralized the neurotoxin from serotype E, thereby allowing the animals to survive the challenge with the neurotoxin. The monovalent vaccine containing the BoNT/Hc/E construct thus induced high titers of antibodies (as described above in Example 6 and FIG. 6C) and these antibodies neutralized the neurotoxin from serotype E. This monovalent vaccine provided survival of lethal doses of neurotoxin from *Clostridium botulinum* serotype E via induction of a strong humoral immune response that included neutralizing antibodies reactive to the neurotoxin.

In summary, the data in the above Examples demonstrated that the vaccines induced high titers of antibodies that were reactive to the neurotoxin from *Clostridium botulinum* and that these antibodies neutralized the neurotoxin, thereby providing significant protection against (i.e., 75% to 100% survival of) lethal doses of the neurotoxin with few to no symptoms of intoxication. Additionally, the bivalent and trivalent vaccines also provided significant protection against (i.e., 75% and 100%, respectively, survival of) neurotoxin from different serotypes of *Clostridium botulinum*.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A vaccine comprising a nucleic acid molecule encoding one or more antigens that induce an immune response against Botulinum toxin, wherein the one or more antigens comprise an amino acid sequence(s) selected from the group consisting of:

(a) heavy chain amino acid sequence of Botulinum A serotype neurotoxin (SEQ ID NO: 2);

(b) heavy chain amino acid sequence of Botulinum B serotype neurotoxin (SEQ ID NO: 4);

(c) heavy chain amino acid sequence of Botulinum E serotype neurotoxin (SEQ ID NO: 6);

(d) heavy chain amino acid sequence of Botulinum F serotype neurotoxin (SEQ ID NO: 8);

(e) an amino acid sequence that is 96% identical or greater to the heavy chain amino acid sequence of Botulinum A serotype neurotoxin (SEQ ID NO: 2);

(f) an amino acid sequence that is 96% identical or greater to the heavy chain amino acid sequence of Botulinum B serotype neurotoxin (SEQ ID NO: 4);

(g) an amino acid sequence that is 96% identical or greater to the heavy chain amino acid sequence of Botulinum E serotype neurotoxin (SEQ ID NO: 6); and (h) an amino acid sequence that is 96% identical or greater to the heavy chain amino acid sequence of Botulinum F serotype neurotoxin (SEQ ID NO: 8).

2. The vaccine of claim 1, wherein the nucleic acid molecule comprises one or more nucleotide sequences selected from the group consisting of: SEQ ID NO:1, SEQ ID NO:3, SEQ ID NO:5, and SEQ ID NO:7.

3. The vaccine of claim 1, wherein the nucleic acid molecule is one or more plasmids.

4. The vaccine of claim 1, further comprising an adjuvant molecule.

5. The vaccine of claim 4, wherein the adjuvant is IL-12, IL-15, IL-28, or regulated upon activation, normal T-cell expressed and secreted (RANTES).

6. A method of inducing an immune response against a Botulinum neurotoxin comprising administering a vaccine of claim 1 to a subject.

7. A method of protecting a subject from Botulinum poisoning comprising administering a vaccine of claim 1 to the subject.

8. The method of claim 6, wherein administration includes electroporation.

9. A vaccine comprising one or more nucleic acid molecules encoding two antigens that induce an immune response against Botulinum toxin, wherein the two antigens comprise two amino acid sequences selected from the group consisting of:
   (a) heavy chain amino acid sequence of Botulinum A serotype neurotoxin (SEQ ID NO: 2);
   (b) heavy chain amino acid sequence of Botulinum B serotype neurotoxin (SEQ ID NO: 4);
   (c) heavy chain amino acid sequence of Botulinum E serotype neurotoxin (SEQ ID NO: 6);
   (d) heavy chain amino acid sequence of Botulinum F serotype neurotoxin (SEQ ID NO: 8);
   (e) an amino acid sequence that is 96% identical or greater to the heavy chain amino acid sequence of Botulinum A serotype neurotoxin (SEQ ID NO: 2);
   (f) an amino acid sequence that is 96% identical or greater to the heavy chain amino acid sequence of Botulinum B serotype neurotoxin (SEQ ID NO: 4);
   (g) an amino acid sequence that is 96% identical or greater to the heavy chain amino acid sequence of Botulinum E serotype neurotoxin (SEQ ID NO: 6); and
   (h) an amino acid sequence that is 96% identical or greater to the heavy chain amino acid sequence of Botulinum F serotype neurotoxin (SEQ ID NO: 8).

10. The vaccine of claim 9, wherein the nucleic acid molecule encodes the heavy chain amino acid sequence of Botulinum A serotype neurotoxin and the heavy chain amino acid sequence of Botulinum B serotype neurotoxin.

11. The vaccine of claim 10, wherein the heavy chain amino acid sequences of Botulinum A serotype neurotoxin and Botulinum B serotype neurotoxin are contained within a single amino acid sequence (SEQ ID NO:9).

12. The vaccine of claim 9, wherein the nucleic acid molecule encodes the heavy chain amino acid sequence of Botulinum E serotype neurotoxin and the heavy chain amino acid sequence of Botulinum F serotype neurotoxin.

13. The vaccine of claim 12, wherein the heavy chain amino acid sequences of Botulinum E serotype neurotoxin and Botulinum F serotype neurotoxin are contained within a single amino acid sequence (SEQ ID NO:10).

14. A vaccine comprising one or more nucleic acid molecules encoding three antigens that induce an immune response against Botulinum toxin, wherein the three antigens comprise three amino acid sequences selected from the group consisting of:
   (a) heavy chain amino acid sequence of Botulinum A serotype neurotoxin (SEQ ID NO: 2);
   (b) heavy chain amino acid sequence of Botulinum B serotype neurotoxin (SEQ ID NO: 4);
   (c) heavy chain amino acid sequence of Botulinum E serotype neurotoxin (SEQ ID NO: 6);
   (d) heavy chain amino acid sequence of Botulinum F serotype neurotoxin (SEQ ID NO: 8);
   (e) an amino acid sequence that is 96% identical or greater to the heavy chain amino acid sequence of Botulinum A serotype neurotoxin (SEQ ID NO: 2);
   (f) an amino acid sequence that is 96% identical or greater to the heavy chain amino acid sequence of Botulinum B serotype neurotoxin (SEQ ID NO: 4);
   (g) an amino acid sequence that is 96% identical or greater to the heavy chain amino acid sequence of Botulinum E serotype neurotoxin (SEQ ID NO: 6); and
   (h) an amino acid sequence that is 96% identical or greater to the heavy chain amino acid sequence of Botulinum F serotype neurotoxin (SEQ ID NO: 8).

15. A vaccine comprising one or more nucleic acid molecules encoding four antigens that induce an immune response against Botulinum toxin, wherein the four antigens comprise four amino acid sequences selected from the group consisting of:
   (a) heavy chain amino acid sequence of Botulinum A serotype neurotoxin (SEQ ID NO: 2);
   (b) heavy chain amino acid sequence of Botulinum B serotype neurotoxin (SEQ ID NO: 4);
   (c) heavy chain amino acid sequence of Botulinum E serotype neurotoxin (SEQ ID NO: 6);
   (d) heavy chain amino acid sequence of Botulinum F serotype neurotoxin (SEQ ID NO: 8);
   (e) an amino acid sequence that is 96% identical or greater to the heavy chain amino acid sequence of Botulinum A serotype neurotoxin (SEQ ID NO: 2);
   (f) an amino acid sequence that is 96% identical or greater to the heavy chain amino acid sequence of Botulinum B serotype neurotoxin (SEQ ID NO: 4);
   (g) an amino acid sequence that is 96% identical or greater to the heavy chain amino acid sequence of Botulinum E serotype neurotoxin (SEQ ID NO: 6); and
   (h) an amino acid sequence that is 96% identical or greater to the heavy chain amino acid sequence of Botulinum F serotype neurotoxin (SEQ ID NO: 8).

16. The vaccine of claim 15, wherein the nucleic acid molecule encodes the heavy chain amino acid sequence of Botulinum A serotype neurotoxin, the heavy chain amino acid sequence of Botulinum B serotype neurotoxin, the heavy chain amino acid sequence of Botulinum E serotype neurotoxin, and the heavy chain amino acid sequence of Botulinum F serotype neurotoxin.

17. The vaccine of claim 16, wherein the heavy chain amino acid sequences of Botulinum A serotype neurotoxin, Botulinum B serotype neurotoxin, Botulinum E serotype neurotoxin, and Botulinum F serotype neurotoxin are contained in a single amino acid sequence.

18. The vaccine of claim 9, wherein the nucleic acid molecule comprises one or more nucleotide sequences selected from the group consisting of: SEQ ID NO:1, SEQ ID NO:3, SEQ ID NO:5, and SEQ ID NO:7.

19. The vaccine of claim 9, wherein the nucleic acid molecule is one or more plasmids.

20. The vaccine of claim 9, further comprising an adjuvant molecule.

21. The vaccine of claim 20, wherein the adjuvant is IL-12, IL-15, IL-28, or regulated upon activation, normal T-cell expressed and secreted (RANTES).

22. A method of inducing an immune response against a Botulinum neurotoxin comprising administering a vaccine of claim 9 to a subject.

23. A method of protecting a subject from botulinum poisoning comprising administering a vaccine of claim 9 to the subject.

24. The method of claims 22 or 23, wherein administration includes electroporation.

25. A nucleic acid molecule comprising one or more nucleotide sequences that encode one or more antigens that induce an immune response against Botulinum toxin, wherein the one or more nucleotide sequences are selected from the group consisting of: SEQ ID NO:1, SEQ ID NO:3, SEQ ID NO:5, SEQ ID NO:7, a nucleotide sequence that is 95% identical or greater to SEQ ID NO:1, a nucleotide sequence that is 95% identical or greater to SEQ ID NO:3, a nucleotide sequence that is 95% identical or greater to SEQ ID NO:5, a nucleotide sequence that is 95% identical or greater to SEQ ID NO:7, and a combination thereof.

26. The nucleic acid molecule of claim 25, wherein the nucleotide sequence is a plasmid.

27. The nucleic acid molecule of claim 25, wherein the one or more nucleotide sequences are one or more plasmids.

28. A nucleic acid molecule of claim 25, wherein the one or more nucleotide sequences encode for one or more amino acid sequences selected from the group consisting of: SEQ ID NO:2, SEQ ID NO:4, SEQ ID NO:6, SEQ ID NO:8, SEQ ID NO:9, SEQ ID NO:10, SEQ ID NO:11, an amino acid sequence 95% identical or greater to SEQ ID NO:2, an amino acid sequence 95% identical or greater to SEQ ID NO:4, an amino acid sequence 95% identical or greater to SEQ ID NO:6, an amino acid sequence 95% identical or greater to SEQ ID NO:8, an amino acid sequence 95% identical or greater to SEQ ID NO:9, an amino acid sequence 95% identical or greater to SEQ ID NO:10, an amino acid sequence 95% identical or greater to SEQ ID NO:11, and a combination thereof.

29. The vaccine of claim 1, wherein the vaccine comprises a construct selected from the group consisting of: a monovalent construct, a multivalent construct, and a combination thereof, and wherein the nucleic acid is 1, 2, 3, 4, or more plasmids.

30. The vaccine claim 1, wherein the vaccine comprises a construct selected from the group consisting of: a monovalent construct, a bivalent construct, a trivalent construct, a quadravalent construct, and a combination thereof, and wherein the nucleic acid is 1, 2, 3, 4, or more plasmids.

* * * * *